US012765576B2

(12) United States Patent
Levenberg et al.

(10) Patent No.: US 12,765,576 B2
(45) Date of Patent: Oct. 20, 2026

(54) 3D-PRINTABLE PROTEIN-ENRICHED SCAFFOLDS

(71) Applicant: ALEPH FARMS LTD., Rehovot (IL)

(72) Inventors: Shulamit Levenberg, Moreshet (IL); Iris Ianovici, Haifa (IL); Yedidya Zagury, Nahariya (IL); Neta Lavon, Ness Ziona (IL); Shlomit David, Jerusalem (IL)

(73) Assignee: ALEPH FARMS LTD., Rehovot (IL)

( * ) Notice: Subject to any disclaimer, the term of this patent is extended or adjusted under 35 U.S.C. 154(b) by 529 days.

(21) Appl. No.: 18/263,334

(22) PCT Filed: Jan. 27, 2022

(86) PCT No.: PCT/IL2022/050117
§ 371 (c)(1),
(2) Date: Jul. 27, 2023

(87) PCT Pub. No.: WO2022/162662
PCT Pub. Date: Aug. 4, 2022

(65) Prior Publication Data
US 2024/0074456 A1 Mar. 7, 2024

Related U.S. Application Data

(60) Provisional application No. 63/142,511, filed on Jan. 28, 2021.

(51) Int. Cl.
*A23J 3/26* (2006.01)
*A23J 3/14* (2006.01)
(Continued)

(52) U.S. Cl.
CPC . *A23J 3/26* (2013.01); *A23J 3/14* (2013.01); *A23J 3/16* (2013.01); *A23J 3/227* (2013.01);
(Continued)

(58) Field of Classification Search
None
See application file for complete search history.

(56) References Cited

U.S. PATENT DOCUMENTS 10,150,258 B2 12/2018 Feinberg
2012/0190078 A1* 7/2012 Gatenholm ............ A61L 27/38 435/395
(Continued)

FOREIGN PATENT DOCUMENTS

CN 109251492 A 1/2019
WO 2015017421 A2 2/2015
(Continued)

OTHER PUBLICATIONS

ThermoFisher, Useful Numbers for Cell Culture, Online Publication, 2006-2025 (Year: 2025).*
(Continued)

*Primary Examiner* — Tracy Vivlemore
*Assistant Examiner* — Hanna Marie Thueson
(74) *Attorney, Agent, or Firm* — Fuller IP Law LLC; Rodney J. Fuller

(57) ABSTRACT

The present invention provides 3D edible scaffolds and methods for the production thereof. The invention further discloses edible inks for use in tissue engineering (TE) applications, such as growing and/or supporting 3D engineered tissues, particularly 3D nutritious engineered edible tissues intended for cultured meat applications.

21 Claims, 41 Drawing Sheets

(51) Int. Cl.

| | |
|---|---|
| *A23J 3/16* | (2006.01) |
| *A23J 3/22* | (2006.01) |
| *A23L 13/00* | (2016.01) |
| *A23L 29/256* | (2016.01) |
| *B33Y 10/00* | (2015.01) |
| *B33Y 70/00* | (2020.01) |
| *B33Y 80/00* | (2015.01) |
| *C12N 5/077* | (2010.01) |

(52) U.S. Cl.

CPC ............ *A23L 13/00* (2016.08); *A23L 29/256* (2016.08); *B33Y 10/00* (2014.12); *B33Y 70/00* (2014.12); *B33Y 80/00* (2014.12); *C12N 5/0659* (2013.01); *C12N 2513/00* (2013.01); *C12N 2533/50* (2013.01); *C12N 2533/74* (2013.01); *C12N 2537/10* (2013.01)

(56) References Cited

U.S. PATENT DOCUMENTS

| | | | |
|---|---|---|---|
| 2014/0113373 | A1 | 4/2014 | Chien |
| 2016/0106142 | A1 | 4/2016 | Contractor |
| 2017/0035076 | A1 | 2/2017 | Geistlinger |
| 2017/0164650 | A1 | 6/2017 | Diaz |
| 2017/0251713 | A1 | 9/2017 | Warner |
| 2018/0192686 | A1 | 7/2018 | Shoseyov |
| 2018/0199614 | A1 | 7/2018 | Zhang |
| 2020/0101198 | A1 | 4/2020 | Dvir |

FOREIGN PATENT DOCUMENTS

| | | | | |
|---|---|---|---|---|
| WO | 2016007879 A1 | | 1/2016 | |
| WO | 2016150960 A1 | | 9/2016 | |
| WO | 2018227016 A1 | | 12/2018 | |
| WO | 2019016795 A1 | | 1/2019 | |
| WO | 2019018737 A1 | | 1/2019 | |
| WO | 2019135237 A1 | | 7/2019 | |
| WO | 2019234738 A1 | | 12/2019 | |
| WO | 2020030628 A1 | | 2/2020 | |
| WO | 2020123876 A1 | | 6/2020 | |
| WO | WO-2020152689 A1 | * | 7/2020 | ................ A23J 3/16 |
| WO | 2020219755 A1 | | 10/2020 | |
| WO | 2021007359 A1 | | 1/2021 | |

OTHER PUBLICATIONS

Zhang et al., Fabrication and characterization of porous polycaprolactone scaffold via extrusion-based cryogenic 3D printing for tissue engineering, 2019, Elsevier, Materials and Design, Online publication, p. 1-10 (Year: 2019).*

McCormack et al., 3D Printing in Suspension Baths: Keeping the Promises of Bioprinting Afloat, 3030, Trends in Biotechnology, vol. 38, No. 6, p. 584-593 (Year: 2020).*

Abbasi (2020) Soy Scaffoldings Poised to Make Cultured Meat More Affordable. JAMA 323(18): 1764.

Axpe and Oyen (2016) Applications of Alginate-Based Bioinks in 3D Bioprinting. Int J Mol Sci 17(12): 1976.

Ben-Arye and Levenberg (2019) Tissue engineering for clean meat production. Frontiers in Sustainable Food Systems 3: 46.

Ben-Arye et al., (2020) Textured soy protein scaffolds enable the generation of three-dimensional bovine skeletal muscle tissue for cell-based meat. Nature Food (1): 210-220.

Bodiou et al., (2020) Microcarriers for Upscaling Cultured Meat Production. Front Nutr 7: 10.

Chien et al., (2013) Three-dimensional printing of soy protein scaffolds for tissue regeneration. Tissue Eng Part C Methods 19(6): 417-426.

Feng et al., (2018) Materials Properties of Printable Edible Inks and Printing Parameters Optimization during 3D Printing: a review. Critical Reviews in Food Science and Nutrition, DOI: 10.1080/10408398.2018.1481823. Accepted author version posted online: Jun. 1, 2018. 26 pages.

Freeman and Kelly (2017) Tuning Alginate Bioink Stiffness and Composition for Controlled Growth Factor Delivery and to Spatially Direct MSC Fate within Bioprinted Tissues. Sci Rep 7(1): 17042.

Godfray et al., (2018) Meat consumption, health, and the environment. Science 361(6399): eaam5324.

Hinton et al., (2015) Three-dimensional printing of complex biological structures by freeform reversible embedding of suspended hydrogels. Sci Adv 1(9): e1500758.

Huebsch et al., (2015) Matrix elasticity of void-forming hydrogels controls transplanted-stem-cell-mediated bone formation. Nat Mater. Author manuscript; available in PMC May 18, 2016. Published in final edited form as: Nat Mater. Dec. 2015; 14(12): 1269-1277.

Hwang et al., (2010) Fabrication of three-dimensional porous cell-laden hydrogel for tissue engineering. Biofabrication 2(3): 035003.

Ianovici et al., (2022) 3D-printable plant protein-enriched scaffolds for cultivated meat development. Biomaterials 284: 121487.

Iravani and Varma (2019) Plants and plant-based polymers as scaffolds for tissue engineering. Green Chem 21: 4839-4867. 29 pages.

Jahangirian et al., (2019) Status of Plant Protein-Based Green Scaffolds for Regenerative Medicine Applications. Biomolecules 9(10): 619.

Jammalamadaka and Tappa (2018) Recent Advances in Biomaterials for 3D Printing and Tissue Engineering. J Funct Biomater 9(1): 22.

Jia et al., (2014) Engineering alginate as bioink for bioprinting. Acta Biomater 10(10): 4323-4331.

Kim et al., (2017) Classification of the printability of selected food for 3D printing: Development of an assessment method using hydrocolloids as reference material. Accepted Manuscript. Journal of Food Engineering, doi: 10.1016/j.jfoodeng.2017.07.017. 37 pages.

Kjar et al., (2020) Engineering of tissue constructs using coaxial bioprinting. Bioact Mater 6(2): 460-471.

Lee et al., (2019) 3D bioprinting of collagen to rebuild components of the human heart. Science 365(6452): 482-487.

Lipton et al., (2015) Additive manufacturing for the food industry.—A review. Accepted Manuscript. Trends in Food Science & Technology, doi: 10.1016/j.tifs.2015.02.004. 18 pages.

Liu et al., (2017) 3D printing: Printing precision and application in food sector. Accepted Manuscript. Trends in Food Science & Technology, doi: 10.1016/j.tifs.2017.08.018. 36 pages.

Mirdamadi et al., (2019) Agarose Slurry as a Support Medium for Bioprinting and Culturing Freestanding Cell-Laden Hydrogel Constructs. 3D Print Addit Manuf 6(3): 158-164.

Mohammadinejad et al., (2020) Recent Advances in Natural Gum-Based Biomaterials for Tissue Engineering and Regenerative Medicine: A Review. Polymers (Basel) 12(1): 176.

O'Brien (2011) Biomaterials & scaffolds for tissue engineering. Materials Today 14(3): 88-95.

Olami and Zilberman (2016) Microstructure and in vitro cellular response to novel soy protein-based porous structures for tissue regeneration applications. J Biomater Appl 30(7): 1004-1015.

Oyinloye and Yoon (2021) Stability of 3D printing using a mixture of pea protein and alginate: Precision and application of additive layer manufacturing simulation approach for stress distribution. Journal of Food Engineering 288 (2021): 110127.

Post et al., (2020) Scientific, sustainability and regulatory challenges of cultured meat. Nature Food 1: 403-415.

Severini et al., (2016) Variables affecting the printability of foods: Preliminary tests on cereal-based products. Innovative Food Science & Emerging Technologies 38(Part A): 281-291.

Tansaz et al., (2018) Soy Protein-Based Composite Hydrogels: Physico-Chemical Characterization and In Vitro Cytocompatibility. Polymers (Basel) 10(10): 1159.

Varankovich et al., (2015) Evaluation of pea protein-polysaccharide matrices for encapsulation of acid-sensitive bacteria. Food Research International 70: 118-124.

(56) References Cited

OTHER PUBLICATIONS

Werkmeister and Ramshaw (2012) Recombinant protein scaffolds for tissue engineering. Biomed Mater 7(1): 012002.
Yeo et al., (2016) Combining a micro/nano-hierarchical scaffold with cell-printing of myoblasts induces cell alignment and differentiation favorable to skeletal muscle tissue regeneration. Biofabrication 8(3): 035021.
Zagury et al., (2022) Engineered marble-like bovine fat tissue for cultured meat. Commun Biol 5(1): 927.
Zidarič et al., (2020) Cultured meat: meat industry hand in hand with biomedical production methods. Food Engineering Reviews 12: 498-519.
3D "meat" printer. Just another weblog. Posted on Oct. 29, 2015 by David van Nunen. Retrieved from: https://web.archive.org/web/20170421051849/https:/meat2015.weblog.tudelft.nl/. 16 pages.
Yissum will unveil new technology for 3D printed food. By (3DA)—Oct. 24, 2017. Retrieved from: https://3dadept.com/yissum-will-unveil-new-technology-for-3d-printed-food/, 2 pages.

* cited by examiner

Day 7

Day 14

Live /Dead

Within bath

Extracted

Phalloidin / DAPI

Desmin / DAPI

With voids Full (control)

Top-view (2.5x)

Cross-section (2.5x)

Cross-section (10x)

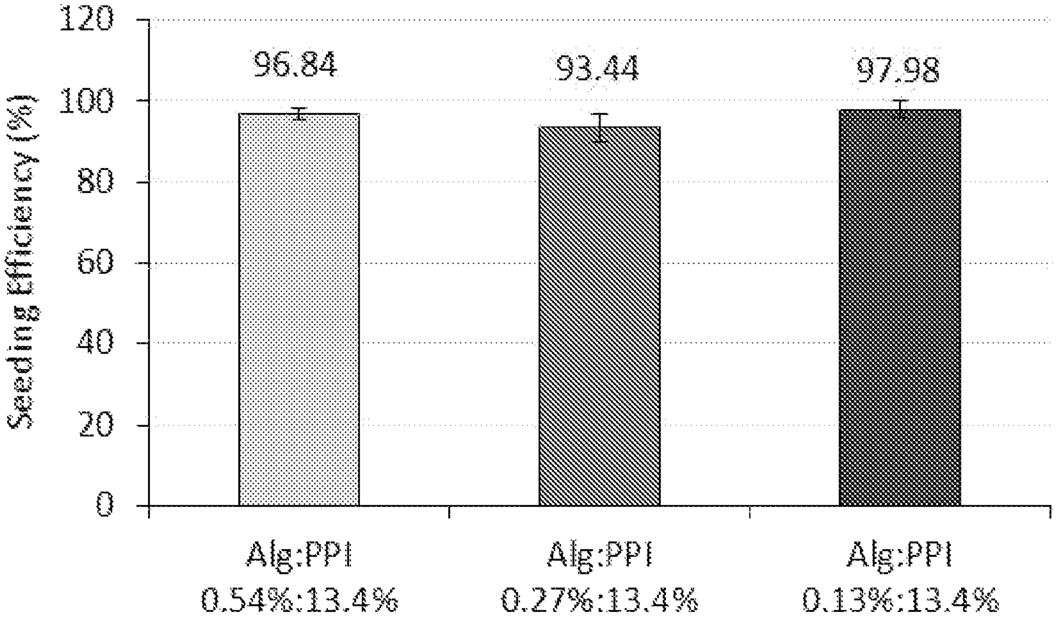
Figure 22E
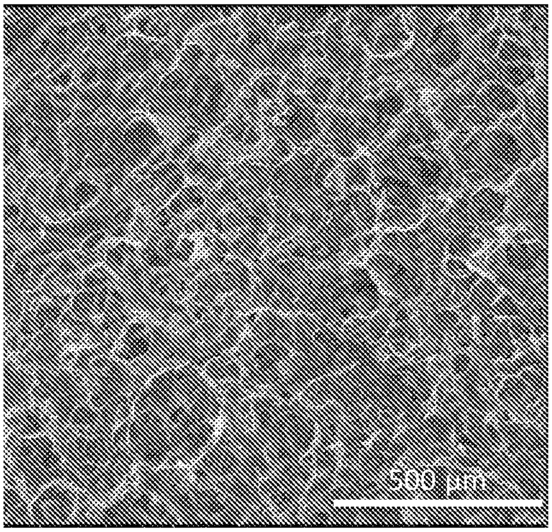
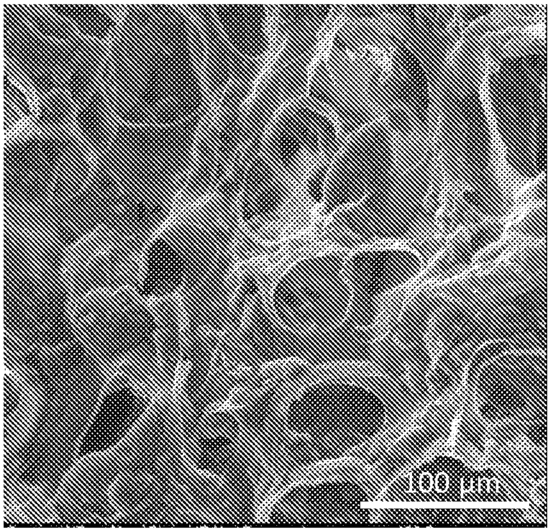
Figure 23A
Figure 23B

3D-PRINTABLE PROTEIN-ENRICHED SCAFFOLDS

CROSS-REFERENCE TO RELATED APPLICATIONS

This application is the U.S. National Stage of International Patent Application No. PCT/IL2022/050117, filed on Jan. 27, 2022, which claims the benefit of and priority to U.S. Provisional Patent Application No. 63/142,511, filed on Jan. 28, 2021, the contents of each of which are hereby incorporated by reference in their entireties.

FIELD OF THE INVENTION

Provided herein are 3D scaffolds and methods for the production thereof, utilizing compositions comprising at least one type of protein as biocompatible edible ink, for use in tissue engineering (TE) applications, such as growing and/or supporting 3D engineered tissues, particularly nutritious engineered edible tissues, optionally intended for cultured meat applications.

BACKGROUND OF THE INVENTION

Cultured meat makes a promising candidate to cope with environmental, health and ethical problems stemmed from the rising demand for meat products over the past decades (Godfray, H. C. J. et al. Meat consumption, health, and the environment. Science 361, 2018). By minimizing largescale animal use, cultured meat could become an agreeable solution once achieving the adequate tissue engineering (TE) technology to construct a three-dimensional (3D) edible muscle-containing tissue. This includes the use of appropriate cell types, scaffolding materials, and fabrication techniques, needed to mimic the complex natural tissue and support cell growth, differentiation and organization (Ben-Arye, T. et al. Textured soy protein scaffolds enable the generation of three-dimensional bovine skeletal muscle tissue for cell-based meat. Nat. Food 1, 210-220, 2020).

Scaffolds are used in TE as 3D cell growth platforms, possessing several key requirements for mimicking the natural cellular micro-environment (O'Brien, F. J. Biomaterials & scaffolds for tissue engineering. Mater. Today 14, 88-95, 2011). For cultured meat, it would be preferable if the fabrication process of the scaffolding materials is based on a repetitive, customizable technology, to enable scaled-up production. One promising method for such fabrication is 3D bio-printing, with printers suitable of precise 3D deposition of materials in highly customizable, complex structures.

Several engineered tissues were previously printed, including skeletal muscle cells, yet research regarding 3D printing for cultured meat purposes is still at an early stage, as it requires additional considerations of the scaffolding materials: preferably being non-animal derived, printable and potentially edible, as the scaffold could become an integral part of the final product (Bodiou, V., Moutsatsou, P. & Post, M. J. Microcarriers for Upscaling Cultured Meat Production. Front. Nutr. 7, 2020).

Plant, algae, or bacteria derived materials, or recombinant biologically active materials (collagen, gelatin, etc.) might be found suitable as alternatives to ones originated from animals (Iravani, S. & Varma, R. S. Plants and plant-based polymers as scaffolds for tissue engineering. Green Chem. 21, 4839-4867, 2019; Werkmeister, J. A. & Ramshaw, J. A. M. Recombinant protein scaffolds for tissue engineering. Biomed. Mater. 7, 2012). For extrusion based-printing, polymers are generally used, as this layer-by-layer fabrication includes a crucial transition from the liquid phase in which the material leaves the printer's nozzle, to its solid state afterwards, enabled by physical, chemical, or enzymatic mechanisms (Jammalamadaka, U. & Tappa, K. Recent advances in biomaterials for 3D printing and tissue engineering. J. Funct. Biomater. 9, 2018).

Jahangirian et al. describe the use of plant-derived proteins as biopolymer materials for several green regenerative medicine and tissue engineering applications including bioprinted scaffolds for cell seeding applications (Jahangirian, H. et al., Status of plant protein-based green scaffolds for regenerative medicine applications. Biomolecules vol. 9, 2019).

Varankovich et al. describe protein-polysaccharide capsules comprising pea protein isolate (PPI) and different polysaccharides for various biological uses, particularly for encapsulation of acid-sensitive bacteria (Varankovich, N. V. et al., Evaluation of pea protein-polysaccharide matrices for encapsulation of acid-sensitive bacteria. Food Research International vol. 70 118-124, 2015).

Chien et al. describe printing soy protein slurry using a 3D Bioplotter to form 3D natural protein scaffolds for cell seeding (Chien, K. B. at al., Three-Dimensional Printing of Soy Protein Scaffolds for Tissue Regeneration. Tissue Eng. Part C Methods 19(6), 417-426, 2012).

Oyinloye, T. M. et al. describe that alginate and pea protein solutions were used for additive-layer manufacturing (ALM) simulation to investigate optimum 3D printing conditions of complex geometries (Oyinloye, T. M., et al. Stability of 3D printing using a mixture of pea protein and alginate: Precision and application of additive layer manufacturing simulation approach for stress distribution. Journal of Food Engineering, 288, 110127, 2021).

Abbasi describes textured soy protein (TSP) for use in manufacturing scaffolds for cultured meat applications (Abbasi, J. Soy Scaffoldings Poised to Make Cultured Meat More Affordable. JAMA 323, 1764, 2020).

Tansaz et al. describe composite hydrogels based on the combination of alginate (Alg), soy protein isolate (SPI) and bioactive glass (BG) nanoparticles developed for soft tissue engineering applications (Tansaz, S. et al., Soy Protein-based composite hydrogels: Physico-chemical characterization and in vitro cytocompatibility. Polymers (Basel). 10, 2018).

Olami et al. describe soy protein-based porous blends comprising soy protein and other polymers (gelatin, pectin and alginate) for use in manufacturing scaffolds for various tissue engineering applications (Olami, H. at al., Microstructure and in vitro cellular response to novel soy protein-based porous structures for tissue regeneration applications. J. Biomater. Appl. 30, 1004-1015, 2016).

US Application Publication No. 2020/0101198 discloses compositions of matter comprising decellularized omentum, which may be scaffolds, hydrogels or hydrogel precursor compositions.

International (PCT) Application Publication No. WO 2020/030628 discloses a process for the manufacturing of an edible microextruded product comprising two or more layers of viscoelastic microextruded elements, wherein each extruded element comprises protein, an edible pseudoplastic polymer and an appropriate edible solvent.

International (PCT) Application Publication No. WO 2019/135237 discloses a composition comprising a porous scaffold that comprises a polymer; and a plurality of particles attached to said polymer, wherein the scaffold is having at least one region that is translucent to low-energy radiation, the particles are capable of generating heat upon interacting with the radiation, and the generated heat renders the polymer reactive to bonding with a tissue in a subject.

Chinese Patent Application Publication No. 109251492 discloses biocompatible ink for 3D printing comprising a mixture of synthetic degradable polymers and natural polymers.

In terms of the 3D-bioprinting technique, one of the current leading methods refers to a 3D bioprinting technique termed freeform reversible embedding of suspended hydrogels (FRESH) (Hinton, T. J. et al. Three-dimensional printing of complex biological structures by freeform reversible embedding of suspended hydrogels. Sci. Adv. 1, 2015). The bio-ink in this method is deposited into a temporary, removable micro-particles based (support) bath, that provides support during printing and polymerization.

U.S. Pat. No. 10,150,258 discloses a method comprising providing a support material within which a structure is fabricated, depositing, into the support material, a structure material to form the fabricated structure, and removing the support material to release the fabricated structure from the support material, wherein the fabricated structure can be a tissue scaffold.

International (PCT) Application Publication No. WO 2019/234738 discloses a support medium for 3D printing biomaterials based on biocompatible hydrogel particles.

International (PCT) Application Publication No. WO 2021/007359 discloses methods, systems and compositions for use in the bio printing of biostructures having predetermined two (2D)- and/or three-dimensional (3D) pattern of cells. Specifically, the disclosure relates to methods and compositions implementable in a computerized bio-printing systems for the fabrication of edible bio structures using drop-on-demand, having a predetermined three-dimensional structure that can be assembled from 2D patterns with cells and extracellular material (ECM) incorporated therein whether in the presence of biocompatible scaffolding or not, in a non-random two- and three-dimensional pattern.

However, the known methods cannot support and/or provide a delicate, cell-friendly 3D-printing process enabling the fabrication of biologically-complex scaffolds structures.

There remains an unmet need for a simple, cost-efficient, delicate, printing method for 3D-printing of protein-based inks, optionally comprising cells, enabling the fabrication of biologically-complex scaffolds structures which are cell-friendly, and preferably animal-component-free and edible, for various tissue engineering applications particularly for food-oriented applications including cultured meat production.

SUMMARY OF THE INVENTION

The present invention provides 3D-printed scaffolds and methods for the fabrication thereof, wherein the scaffolds are based on 3D-printed denatured protein-based bio-inks, including bio-ink comprising cells.

The present investors have discovered that 3D printing of aqueous compositions containing low concentrations of alginate:RGD-SPI (1%-1% w/v) and/or alginate:RGD-PPI (1%-1% w/v) into a support bath containing agar and calcium ions, unexpectedly enable a delicate, cell-friendly, and accurate 3D printing process, for the fabrication of a variety of 3D-printed hydrogel-based scaffolds having complex structures and/or patterns. The present inventors have further discovered that said 3D-printed hydrogel-based scaffolds can successfully support bovine-satellite cells (BSCs) attachment, and, furthermore, differentiation and maturation thereon, which can be used in growing a 3D engineered tissue. A somewhat higher concentration of protein (13-15% PPI) enabled using RGD-free alginate, without negatively affecting the cell-support characteristics of the scaffold. The compositions and methods of the present invention provide for 3D printed scaffolds combining soft and rigid areas, and enables the integration of living natural animal cells into the scaffold carrier material that envelops the cells to form the building blocks of a whole tissue, particularly muscle and/or fat tissues. In specific embodiments, the animal cells are non-human-animal cells, and the printed scaffold is comprised of edible components forming 3D nutritious engineered edible tissue. The 3D printed tissue is then incubated to acquire the texture and qualities mimicking slaughtered meat portion, particularly in a form of a marbled steak, as the cells continue to develop and interact under controlled conditions. The successful formation of a 3D nutritious engineered edible structure that functions like the vascular system using the compositions and methods of the invention has not only enabled a perfusion of nutrients across the thick tissue formed, but with its composition of fat and muscle, it also maintains a similar shape and structure of a native livestock tissue found in nature before and during cooking. The compositions and methods of the present invention provides for the formation of a cultivated thicker ribeye-like portion that incorporates muscle and fat similar to its slaughtered counterpart, and boasts the same organoleptic attributes of a delicious tender, juicy ribeye steak.

Thus, according to an aspect of the present invention, there is provided a method for producing an edible three-dimensional (3D) scaffold comprising at least one layer comprising at least one edible member, wherein the edible member comprises at least one type of protein and at least one type of polysaccharide, the method comprising the steps of: (a) providing at least one aqueous composition comprising at least one type of protein at a concentration range of about 0.1-15% w/v of the composition, and at least one type of polysaccharide; (b) providing a support medium compatible to scaffold fabrication; (c) depositing the at least one composition of step (a) into the support medium of step (b) in a predetermined pattern, thereby forming at least one edible member therein, wherein the deposition is performed under conditions enabling the transition of the at least one edible member to a solid or semisolid state, thereby forming a 3D scaffold having a predetermined structure comprising at least one layer comprising at least one edible member; and optionally, (d) separating or removing the support medium in order to release the 3D scaffold having the solid or semisolid 3D scaffold of step (c) therefrom.

According to some embodiments, the support medium is configured to mechanically support the deposition of the at least one edible member, in order to form the predetermined structure of the 3D scaffold. According to some embodiments, the support medium is configured as a mold.

According to some embodiments, the at least one type of protein is derived from at least one of a plant, a fungus, an alga, a single cell microorganism, a non-human-animal and any combination thereof.

According to some embodiments, the at least one type of protein is derived from a plant selected from the group consisting of pea, soy, rice, pumpkin, hemp, wheat, mungbean, corn, chickpeas, lentils, canola (seeds), sunflower (seeds), amaranth, lupin, rape-seeds, duckweed, carob, oat, peanut, and any combination thereof.

According to some embodiments, the protein is selected from the group consisting of a pea protein isolate (PPI), a soybean protein isolate (SPI), or a combination thereof. Each possibility represents a separate embodiment of the present invention.

According to some embodiments, the at least one type of protein is derived from a single cell microorganism selected from the group consisting of yeast, microalgae and bacteria. Each possibility represents a separate embodiment of the present invention. According to some embodiments, the microalgae are blue-green microalgae.

According to some embodiments, the protein is a non-human-animal protein selected from the group consisting of collagen, gelatin, elastin, fibronectin, osteopontin, silk fibroin, laminin, vitronectin and any combination thereof. The protein can be natural or recombinant.

According to some embodiments, the non-human-animal protein is whey protein.

According to some embodiments, the polysaccharide is selected from the group consisting of alginate, starch, bean, gum, gellan-gum, hyaluronic acid, cellulose, chitin, chitosan, xanthan gum, agar, agarose, pectin, dextran, carrageenan, modifications and/or variations thereof, and combinations thereof. Each possibility represents a separate embodiment of the present invention. According to certain embodiments, the polysaccharide is modified with arginine-glycine-aspartic (RGD) amino acid derivatives (RGD-modified polysaccharide). According to some embodiments, the polysaccharide is selected from the group consisting of alginate and RGD-modified alginate.

According to some embodiments, the composition of step (a) is in a form of an aqueous solution.

According to certain embodiments, the at least one protein and at least on polysaccharide are edible, thereby forming an edible scaffold. According to these embodiments, the supporting medium comprises food safe materials.

According to some embodiments, the composition of step (a) comprises at least one type of protein at a concentration range of about 0.1-10% w/v of the composition and at least one polysaccharide at a concentration range of about 0.1-10% w/v of the composition.

According to some embodiments, the ratio of the at least one type of protein to the polysaccharide in the composition of step (a) is from about 100:1 to 1:15.

According to some embodiments, the composition of step (a) comprises at least one type of protein selected from the group consisting of PPI, SPI, or a combination thereof, and a polysaccharide selected from the group consisting of alginate and RGD-modified alginate.

According to some embodiments, the composition of step (a) comprises PPI at a concentration range of about 0.1-5% w/v of the composition and/or SPI at a concentration range of about 0.1-5% w/v of the composition, and alginate or RGD-modified alginate at a concentration range of about 0.1-5% w/v of said composition.

According to some embodiments, the composition of step (a) is characterized by having a viscosity of up to $6\times10^7$ mPa.

According to certain exemplary embodiments, the composition of step (a) is characterized by having a viscosity in the range of from about 30 mPa to about $6\times10^7$ mPa.

According to some embodiments, the support medium is in the form of a removable support bath. According to some embodiments, during step (c), relative movement is initiated between the support bath and an apparatus configured to deposit the at least one composition of step (a) thereto, thereby forming the 3D scaffold having the predetermined structure therein.

According to some embodiments, the support medium from step (b) comprises a material selected from the group consisting of a hydrogel material, micronized particulates, a thermo-reversible material and any combination thereof. According to certain embodiments, the material comprised in the support medium is non-animal derived material. According to some embodiments, the non-animal derived material is food-safe.

According to some embodiments, the material contained or comprised within the support medium from step (b) is in the form of a hydrogel and comprises at least one material selected from agar, agarose, gelatin, gellan gum, xanthan gum, gum *arabica*, and any combination thereof. Each possibility represents a separate embodiment of the present invention.

According to some embodiments, the conditions enabling transition of the 3D scaffold comprising the at least one edible member to a solid or semisolid state in step (c) comprises exposing said at least one edible member to at least one crosslinking mechanism, thereby causing said at least one edible member to transition to a solid or semisolid state.

According to some embodiments, the crosslinking mechanism is selected from the group consisting of chemical crosslinking, thermal crosslinking, photopolymerization, enzymatic polymerization, and combinations thereof.

According to some embodiments, the chemical crosslinking comprises exposing the predetermined structure comprising the at least one edible member to at least one divalent ion selected from the group consisting of calcium ($Ca^{+2}$), magnesium ($Mg^{+2}$), iron ($Fe^{+2}$), and salts thereof. According to some embodiments, the chemical crosslinking agent is $CaCl_2$. According to some embodiments, the at least one divalent ion or the salt thereof is comprised within the support medium and/or within a solution added to the predetermined structure. According to some embodiments, the at least one divalent ion or the salt thereof is comprised within the support medium at a concentration range of from about 0.1 to about 200 mM. According to some embodiments, the at least one divalent ion or the salt thereof is comprised within the solution added to the predetermined structure at a concentration range of from about 50 to about 200 mM.

According to some embodiments, the concertation of the divalent ion or salt thereof is constant throughout the crosslinking process.

According to some embodiments, the concertation of the divalent ion or salt thereof is gradually elevated from the starting time point to the end time point of the crosslinking process.

Any method/apparatus as is known in the art for depositing the at least one composition of step (a) into the support medium can be used according to the teachings of the present invention.

According to certain embodiments, the deposition is performed using 3D printer. According to some embodiments, the 3D printer is a computer-aided device.

According to some embodiments, the deposition at step (c) of the at least one composition of step (a) into the support medium, is performed using an extruder.

According to some embodiments, the deposition at step (c) of the at least one composition of step (a) into the support medium is performed using a 3D printer comprising an extruder, wherein step (c) comprises at least partially inserting the extruder into the support medium and extruding the at least one edible member at least partially within the support material. According to further embodiments, step (c) comprises inserting the extruder into the support medium and extruding a plurality of edible members in a predetermined pattern within the support material, thereby forming a 3D scaffold therein having a predetermined structure, wherein the predetermined structure comprises at least one layer (or a plurality of layers) comprising the plurality of edible members, wherein the plurality of edible members intersect between themselves and/or are arranged in parallel to each other.

According to some embodiments, the deposition at step (c) is performed using a coaxial extrusion of a core hydrogel within a shell hydrogel, utilizing a coaxial extruder head optionally made from at least two coaxial nozzles, configured to ensure that the core exits at the geometric inner part of the shell in a coaxial configuration, thereby forming at least one extruded member having a core-shell structure. According to some embodiments, the core hydrogel comprises at least one material selected from the group consisting of: collagen, recombinant collagen, recombinant gelatin, hyaluronic acid, chitosan, pectin, carrageenan, guar gum, xanthan gum, Pluronic F-127, Polyvinyl alcohol (PVA), Butenediol vinyl alcohol (BVOH), alginate, PPI and/or SPI (each in a concentration selected from the range of 0.1-15% w/v), RGD-modified alginate and PPI and/or SPI (each in a concentration selected from the range of 0.1-15% w/v), at least one type of non-human animal cells at a concentration selected from the range of 1-500 Million cells/ml, and combinations thereof. According to some embodiments, the shell hydrogel comprises alginate and PPI and/or SPI, each in a concentration selected from the range of 0.1-10% w/v, and optionally at least one type of non-human animal cells at a concentration selected from the range of 1-500 Million cells/ml.

According to some embodiments, the method comprises providing at least two compositions at step (a) comprising a first composition and a second composition, wherein each of the first and the second compositions comprises at least one type of protein at a concentration range of about 0.1-15% w/v of the composition, and at least one type of polysaccharide. According to some embodiments, the first and the second compositions each comprises a different combination and/or concentration of the at least one type of protein and at least one type of polysaccharide, wherein at step (c) the first and second compositions are simultaneously extruded by a first and second extruders, respectively, at least partially into the support medium.

A significant advantage of the compositions and methods of the present invention is in that the scaffold formed, either when a freeze-drying step is employed or not, may have a pre-set pattern of void volume according to the intended use of the scaffold.

According to certain embodiments, the void volume pattern is determined by a pre-planned printing design including areas in which the composition of step (a) is not deposited. As described in details and exemplified hereinbelow, different patterns may be designed, including for example layered honeycomb structure, layered grid structure and the like.

According to certain embodiments, the pattern mimics a meat portion. According to certain exemplary embodiments, the pattern mimics a rib-eye steak.

Advantageously, employing the method of the present invention with at least two protein-based compositions enables the formation of a scaffold characterized by a variable texture in terms of composition and/or strength and/or rigidity.

According to some embodiments, the 3D scaffold is characterized by having a Young's modulus in the range of about 0.1 kPa to 1 MPa.

According to some embodiments, the 3D scaffold comprises a plurality of layers, vertically stacked one on top of the other.

According to some embodiments, the method further comprises step (e) of freeze drying the 3D scaffold, thereby forming a porous, 3D scaffold having a porosity in the range of about 50%-95% out of the total volume of said scaffold.

The protein based-compositions of the present invention may further contain at least one type of non-human-animal cells. Unexpectedly, the protein-based compositions of the invention enable depositing said compositions to form a predetermined cell-containing structure, including when the deposition is via extrusion, without negatively affecting the cell viability and growth, including cell proliferation and/or differentiation and/or maturation.

Thus, according to some embodiments, the composition of step (a) further comprises a plurality of at least one type of non-human-animal cells.

According to some embodiments, the concentration of the plurality of the at least one type of non-human-animal cells is in the range of about $5\times10^3$-$500\times10^6$ cells/ml of the composition.

According to certain embodiments, the composition of step (a) comprises a plurality of pluripotent stem cells (PSCs) derived from non-human animal. According to certain embodiments, the PSCs are embryonic stem cells. According to certain embodiments, the PSCs are induced pluripotent stem cells (iPSCs).

According to some embodiments, the plurality of non-human-animal cells comprises at least one type of cells selected from the group consisting of stromal cells, endothelial cells, fat cells, muscle cells, hepatocytes, cardiomyocytes, renal cells, lymphoid and epithelial cells, neural and neuronal cells, ciliated epithelial, stomach cells, progenitor cells thereof and any combination thereof. Each possibility represents a separate embodiment of the present invention.

According to some embodiments, the plurality of cells comprises at least one type of non-human-animal cells selected from the group consisting of muscle cells, extracellular matrix (ECM)-secreting cells, fat cells, endothelial cells, progenitors thereof and any combination thereof. Each possibility represents a separate embodiment of the present invention.

According to some embodiments, the plurality of non-human animal cells comprises muscle cells or progenitors thereof and at least one additional type of cells selected from the group consisting of ECM-secreting cells, fat cells, endothelial cells, progenitors thereof and any combination thereof. Each possibility represents a separate embodiment of the present invention.

According to some embodiments, the plurality of non-human animal cells comprises muscle cells or progenitors thereof, ECM-secreting cells or progenitors thereof, fat cells or progenitors thereof, and endothelial cells or progenitors thereof.

According to some embodiments, the composition of step (a) comprises at least one type of protein, at least one type of polysaccharide, and at least one type of cells.

According to certain embodiments, the non-human-animal is selected from the group consisting of ungulate, poultry, aquatic animals, invertebrate and reptiles. Each possibility represents a separate embodiment of the present invention.

According to certain embodiments, the ungulate is selected from the group consisting of a bovine, an ovine, an equine, a pig, a giraffe, a camel, a deer, a hippopotamus, or a rhinoceros. According to some embodiments the ungulate is a bovine. According to certain exemplary embodiments, the bovine is a cow.

According to certain exemplary embodiments, the bovine cells are selected from the group consisting of bovine satellite cells (BSCs), bovine mesenchymal stem cells (BMSCs), bovine mesenchymal cells (BMCs), bovine smooth muscle cells (BSMCs), bovine endothelial cells (BECs), progenitors thereof and any combination thereof. Each possibility represents a separate embodiment of the present invention.

According to some embodiments, the composition of step (a) comprises at least one type of protein selected from PPI and SPI at a concentration range of about 0.1-15% w/v of the composition; at least one type of polysaccharide selected from the group consisting of alginate and RGD-modified alginate at a concentration range of about 0.1-5% w/v of the composition, and at least one type of non-human-animal cells at a concentration range of about $5\times10^3$-$500\times10^6$ cell/ml of the composition. According to some embodiments, the composition of step (a) comprises at least one type of protein selected from PPI and SPI at a concentration range of about 11-15% w/v of the composition; alginate at a concentration range of about 0.1-5% w/v of the composition, and at least one type of non-human-animal cells at a concentration range of about $5\times10^3$-$500\times10^6$ cell/ml of the composition.

According to some embodiments, the scaffold void volume is in a form of pores. According to some embodiments, the pores are interconnected to form channels within the scaffold. When the scaffold is used for growing cells (either comprised with the deposited composition or seeded after formation of the scaffold), the porous structure is pre-set to obtain optimal nourishment of the cells by a cell culture medium.

According to some embodiments, following step (d), the method further comprises placing the 3D scaffold comprising a plurality of at least one type of non-human-animal animal cells under growth conditions enabling proliferation and/or differentiation and/or maturation of the plurality of at least one type of cells to form at least one type of tissue.

According to certain exemplary embodiments, the method results in producing cultured meat product.

According to some embodiments, the cultured meat product comprises fat cells and/or tissue and muscle cells and/or tissue. According to further embodiments, the cultured meat product comprises fat cells and/or tissue; muscle cells and/or tissue and endothelial cells. According to some embodiments, blood vessels may also be formed within the tissues forming the cultured meat.

According to some embodiments, the method results in the formation of a 3D scaffold for the production of cultured tissue.

According to some embodiments, the method results in the formation of a 3D nutritious scaffold for the production of cultured meat.

According to some embodiments, there is provided a freeze-dried 3D edible scaffold fabricated according to the method as disclosed herein above.

According to some embodiments, there is provided an edible 3D scaffold comprising a plurality of at least one type of non-human-animal cells fabricated by the method as disclosed herein above.

According to some embodiments, there is provided a cultured meat product produced by the method as disclosed herein above.

According to yet additional aspect, there is provided an edible 3D scaffold comprising at least one layer comprising at least one edible member, wherein the at least one member comprises at least one hydrogel composition comprising at least one edible protein at a concentration range of about 0.1-15% w/v of the composition and at least one edible polysaccharide. According to some embodiments, the hydrogel composition comprises at least one type of protein at a concentration range of about 0.1-15% w/v of the composition and/or at least one polysaccharide at a concentration range of about 0.1-5% w/v of the composition.

According to some embodiments, the edible 3D scaffold comprises a plurality of layers, wherein each layer comprises a plurality of edible members, wherein each member comprises at least one hydrogel composition comprising at least one protein at a concentration range of about 0.1-15% w/v of the composition and at least one polysaccharide at a concentration range of about 0.1-15% w/v of the composition. According to further embodiments, the hydrogel composition comprises at least one protein at a concentration range of about 0.1-15% w/v of the composition and at least one polysaccharide at a concentration range of about 0.1-5% w/v of the composition. According to further embodiments, the plurality of edible members is intersected between themselves and/or are arranged in parallel to each other within the same layer or in different layers, wherein consecutive layers are spaced from each other to form voids therebetween, and wherein edible members within the same layer are spaced from each other to form channels therebetween.

According to certain embodiments, the hydrogel composition comprises the at least one protein and at least one polysaccharide at a ratio of from about 100:1 (i.e., protein:polysaccharide=100:1) to 1:15 (i.e., protein:polysaccharide=1:15).

According to certain embodiment, the edible 3D scaffold further comprises a plurality of at least one type of non-human-animal cells.

The non-human-animal cells are as described hereinabove.

According to some embodiments, there is provided a 3D edible scaffold for use in growing a 3D nutritious engineered edible tissue, intended for cultured meat.

According to yet further aspect, there is provided an edible ink comprising a hydrogel composition comprising at least one type of edible protein at a concentration range of about 0.1-15% w/v % of the composition, and at least one type of edible polysaccharide, wherein the ink is suitable for 3D printing.

According to certain embodiments, the edible ink further comprises a plurality of at least one type of non-human-animal cells.

The proteins, polysaccharides and non-human-animal cells are as described hereinabove.

According to certain exemplary embodiments, the edible ink comprising a plurality of at least one type of non-human-animal cells is used for printing 3D cultured meat product.

According to yet further aspect, there is provided a method for producing an edible three-dimensional (3D) scaffold, the method comprising the steps of: (a) providing at least one aqueous composition comprising at least one type of edible protein at a concentration range of about 0.1-15% w/v of the composition, and at least one type of edible polysaccharide at a concentration range of about 0.1-5% w/v of the composition; (b) depositing the at least one aqueous composition of step (a) into a mold, wherein the deposition is performed under conditions enabling the transition of the at least one aqueous composition to a solid or semisolid state, thereby forming a 3D scaffold having a molded structure; and (c) freeze drying the 3D scaffold, thereby forming a porous, 3D scaffold having a porosity in the range of about 50%-95% out of the total volume of said scaffold. According to some embodiments, the molded structure of the 3D scaffold corresponds/matches to the shape of the mold. The term "molded structure" as used herein refers to a 3D structure which is formed by depositing an aqueous composition into a mold having a 3D shape, and crosslinking said aqueous composition, to form a 3D structure therein. The conditions enabling the transition of the at least one aqueous composition to a solid or semisolid state comprise crosslinking, as disclosed herein below in detail.

According to certain embodiments, the method further comprises seeding in/or the formed freeze-dried scaffold a plurality of at least one type of non-human-animal cell. According to some embodiment's, the scaffold comprising the plurality of cells is placed under conditions enabling the proliferation and/or differentiation and/or maturation of the seeded cells as to form an edible scaffold comprising at least one type of cells and/or tissue.

It is to be understood that any combination of each of the aspects and the embodiments disclosed herein is explicitly encompassed within the disclosure of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures:

FIG. 7A is representative images of BSCs on each scaffold type, after 1-week differentiation phase. Samples were stained with anti-Desmin (Red) and anti-Myogenin (White) antibodies, with the addition of DAPI (Blue), and observed with a Confocal microscope with 5× (scale bar=500 μm) & 20× (scale bar=50 μm) magnifications. FIGS. 7B-C represent qPCR results of MyoD (FIG. 7B) and Myogenin (FIG. 7C) expressions within BSCs on the three scaffold types, respectively. For both genes, extracted RNA was converted into c-DNA and used with suitable primers (Taqman) for PCR analysis. Measurements of each sample were normalized to the 18S house-keeping gene. For both, statistical Analysis was done using Prism's One-Way-Anova, N=3. All p-values >0.05.

FIGS. 8A-C show the attachment and spreading of DiI-stained BSCs on grid-patterned 3D printed and sterilized scaffolds, imaged 7-days post seeding, wherein the scale bars are: 2 mm (FIG. 8A); 500 μm (FIG. 8B); and 100 μm (FIG. 8C). FIG. 8D shows a regular image of freeze dried and sterilized square scaffolds with inner pattern of parallel strands, prepared prior to BSCs seeding. FIG. 8E shows a regular image of the seeded scaffold at the endpoint of differentiation experiments, before immunostaining. FIGS. 8F and 8G show confocal images of samples which were immunostained against Desmin, with the addition of DAPI for general nuclear staining.

FIG. 22E show seeding efficiency of bovine satellite cells in alginate:high PPI concentration scaffolds, wherein the alginate:pea protein concentrations are 0.54%:13.4%, 0.27%:13.4% and 0.13%:13.4%.

FIGS. 23A-F show SEM images of alginate:high PPI concentration scaffolds, having the following alginate:PPI w/v concentrations: 054%:13.4% (FIGS. 23A-B); 0.27%: 13.4% (FIGS. 23C-D), and 0.13%:13.4% (FIGS. 23E-F).

DETAILED DESCRIPTION OF THE INVENTION

The present invention provides compositions and methods for producing a three-dimensional (3D), preferably edible, scaffold. According to some embodiments, the scaffold comprises at least one layer comprising at least one edible member, wherein said member comprises at least one type of protein and at least one type of polysaccharide.

As used herein, the term "scaffold" refers to an edible three-dimensional (3D) structure comprising a material that provides a surface suitable for adherence/attachment and optionally, proliferation and/or differentiation and/or maturation of cells. A scaffold may further provide mechanical stability and support. A scaffold may be in a particular shape or form so as to influence or delimit a three-dimensional shape or form assumed by a population of adhered, proliferating or differentiating cells. According to some embodiments of the present invention, the scaffold is a three-dimensional construct comprising a plurality of members made from an edible material and arranged in a specific pattern. According to some embodiments, the 3D edible scaffold of the present invention is appropriate for supporting seeding, differentiation, growth and expansion of cells and/or tissues thereon.

As used herein, the term "edible" refers to a material that is safe to be orally consumed by an animal, particularly by mammals, more particularly human.

Figure 1A:
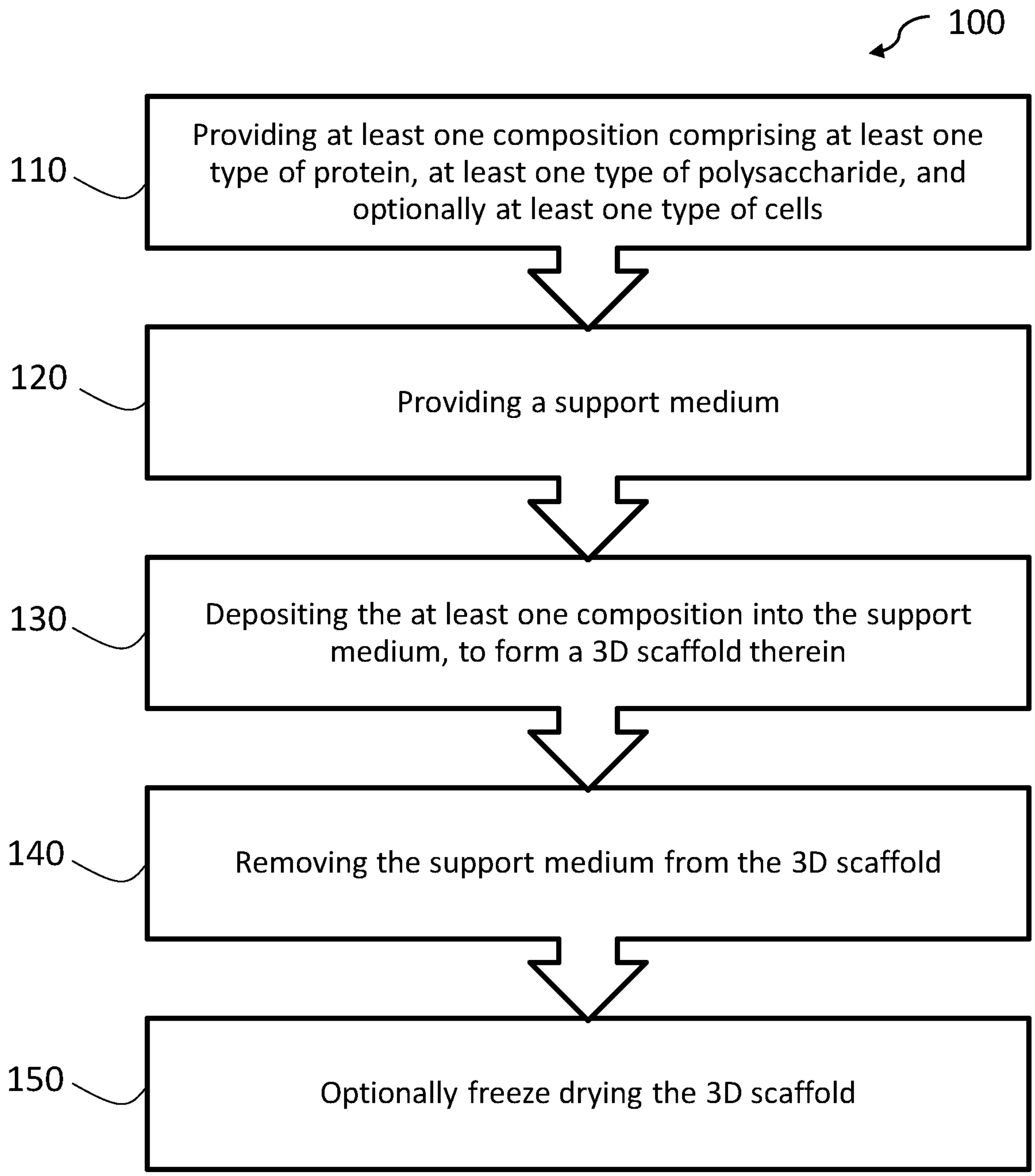
FIG. 1A show a flowchart for a method 100 for the fabrication of a 3D scaffold, according to some embodiments.

Reference is now made to FIG. 1A, illustrating a method 100 for the fabrication of a 3D scaffold, according to some embodiments.

According to a certain aspect, there is provided a method 100 for producing a 3D scaffold, wherein the method comprises step 110 of providing at least one aqueous composition comprising at least one type of protein at a concentration selected from the range of about 0.1-15% w/v of the composition, at least one type of polysaccharide, and optionally at least one type of non-human-animal cells. According to further such embodiments, step 110 comprises providing a plurality of aqueous compositions, wherein each composition comprises at least one type of protein at a concentration selected from the range of about 0.1-15% w/v of the composition, at least one type of polysaccharide, and optionally at least one type of non-human-animal cells.

According to some embodiments, the at least one type of protein of the at least one composition of step 110 is derived from at least one of a plant, a fungus, an alga, a single cell microorganism, a non-human animal and any combination thereof. Each possibility represents a separate embodiment of the present invention. According to certain exemplary embodiments, the at least one type of protein is a plant protein.

According to some embodiments, the at least one type of protein of the at least one composition of step 110 is derived from a single cell microorganism selected from the group consisting of yeast, microalgae and bacteria. According to some embodiments, the microalgae are blue-green algae, including *Spirulina*.

According to some embodiments, the at least one type of protein of the at least one composition of step 110 is a non-human animal protein selected from the group consisting of collagen, gelatin, elastin, fibronectin, osteopontin, silk fibroin, laminin, vitronectin and any combination thereof. Each possibility represents a separate embodiment of the present invention. The protein can be natural or recombinant.

According to some embodiments, the non-human animal protein is whey protein.

According to some embodiments, the at least one type of protein of the at least one composition of step 110 is derived from a plant selected from the group consisting of pea, soy, rice, pumpkin, hemp, wheat, mung-bean, corn, chickpeas, lentils, canola (seeds), sunflower (seeds), amaranth, lupin, rape-seeds, duckweed, carob, oat, peanut, and any combination thereof. Each possibility represents a separate embodiment of the present invention.

According to certain exemplary embodiments, the protein is a pea protein isolate (PPI). According to additional or alternative embodiments, the protein is soy protein isolate (SPI).

According to some embodiments, the at least one type of protein of the at least one composition of step 110 is selected from the group consisting of a pea protein isolate (PPI), a soybean protein isolate (SPI), or a combination thereof. Each possibility represents a separate embodiment of the present invention.

According to some embodiments, the polysaccharide of the at least one composition of step 110 is selected from the group consisting of alginate, starch, bean, gum, gellan-gum, hyaluronic acid, cellulose, chitin, chitosan, xanthan gum, agar, agarose, pectin, dextran, carrageenan, modifications and/or variations thereof, and combinations thereof. Each possibility represents a separate embodiment of the present invention. The polysaccharide modification can affect the polysaccharide melting point, viscosity, cell attachment capacity and more. According to some embodiments, the modification comprises attachment of a peptide or a protein to the polysaccharide backbone. According to some embodiments, the modification comprises polysaccharide oxidation. According to certain embodiments, the polysaccharide is selected from the group consisting of alginate, alginate modified with arginine-glycine-aspartic (RGD) amino acid derivatives (RGD-modified alginate) and oxidized variants thereof.

According to some embodiments, the composition of step 110 is in a form of an aqueous solution. In further embodiments, the composition of step 110 is in a liquid state.

According to some embodiments, the aqueous composition of step 110 comprises a solvent (e.g., water) content greater than about 60% w/v, greater than about 70% w/v, greater than about 80% w/v, greater than about 90% w/v, or greater than about 95% w/v of the aqueous composition. Each possibility represents a different embodiment.

According to some embodiments, the aqueous composition of step 110 comprises a solvent content in the range of about 70% to 98% w/v, optionally about 80% to 98% w/v, or alternatively about 90% to 98% w/v of the aqueous composition. Each possibility represents a different embodiment. According to further embodiments, the solvent is edible (e.g., water).

According to some embodiments, the composition of step 110 comprises at least one type of protein at a concentration range of about 0.1-15% w/v of the composition and/or at least one polysaccharide at a concentration range of about 0.1-15% w/v of the composition. According to further embodiments, the composition of step 110 comprises at least one type of protein at a concentration range of about 0.1-10% w/v of the composition and/or at least one polysaccharide at a concentration range of about 0.1-10% w/v of the composition. According to still further embodiments, the composition of step 110 comprises at least one type of protein at a concentration range of about 0.5-5% w/v of the composition and/or at least one polysaccharide at a concentration range of about 0.5-5% w/v of the composition. According to yet still further embodiments, the composition of step 110 comprises at least one type of protein at a concentration range of about 0.5-3% w/v of the composition and/or at least one polysaccharide at a concentration range of about 0.5-3% w/v of the composition. According to some embodiments, the composition of step 110 comprises at least one type of protein at a concentration range of about 0.1-15% w/v of the composition and/or at least one polysaccharide at a concentration range of about 0.1-5% w/v of the composition. According to some exemplary embodiments, the composition of step 110 comprises at least one type of protein at a concentration of about 1% w/v of the composition and/or at least one polysaccharide at a concentration of about 1% w/v of the composition.

According to some embodiments, the composition of step 110 comprises at least one type of protein at a concentration range of about 10-15% w/v of the composition and/or at least one polysaccharide at a concentration range of about 0.1-10% w/v of the composition. According to further embodiments, the composition of step 110 comprises at least one type of protein at a concentration range of about 11-14% w/v of the composition and/or at least one polysaccharide at a concentration range of about 0.2-5% w/v of the composition. According to a specific embodiment, the composition of step 110 comprises at least one type of protein (e.g., PPI) at a concentration of about 13.4% w/v of the composition and/or at least one polysaccharide (e.g., alginate) at a concentration of about 0.5% w/v of the composition.

According to some embodiments, the composition of step 110 comprises at least one type of protein at a concentration range of about 0.1-15% w/w of the composition and/or at least one polysaccharide at a concentration range of about 0.1-15% w/w of the composition. According to further embodiments, the composition of step 110 comprises at least one type of protein at a concentration range of about 0.5-10% w/w of the composition and/or at least one polysaccharide at a concentration range of about 0.5-10% w/w of the composition. According to still further embodiments, the composition of step 110 comprises at least one type of protein at a concentration range of about 1-5% w/w of the composition and/or at least one polysaccharide at a concentration range of about 1-5% w/w of the composition. It should be understood that w/w % ratios depend on the type of solvent (and the density thereof) added to the composition, wherein various types of solvents (e.g., water, PBS, etc.) may be used.

According to some embodiments, in the composition of step 110, the ratio of the at least one type of protein to the polysaccharide (i.e., protein:polysaccharide) is in the range of about 100:1 (i.e., protein:polysaccharide=100:1) to about 1:15 (i.e., protein:polysaccharide=1:15). According to further embodiments, the ratio of the at least one type of protein to the polysaccharide is in the range of about 50:1 to about 1:2. According to still further embodiments, the ratio of the at least one type of protein to the polysaccharide is in the range of about 25:1 to about 1:1.

According to some embodiments, the ratio of the at least one type of protein to the polysaccharide in the composition of step 110 is in the range of about 1-100 (protein):1-15 (polysaccharide). According to some embodiments, the ratio of the at least one type of protein to the polysaccharide in the composition of step 110 is in the range of about 1-100 (protein):1-5 (polysaccharide), meaning the ratio of protein: polysaccharide is between 100:1 to 1:5. According to further embodiments, the ratio of the at least one type of protein to the polysaccharide in the composition of step 110 is in the range of about 1-10 (protein):1-10 (polysaccharide). According to further embodiments, the ratio of the at least one type of protein to the polysaccharide in the composition of step 110 is in the range of about 1-5 (protein):1-5 (polysaccharide). According to still further embodiments, the ratio of the at least one type of protein to the polysaccharide in the composition of step 110 is in the range of about 1-2 (protein):1-2 (polysaccharide).

According to some exemplary embodiments, the ratio of the at least one type of protein to the polysaccharide in the composition of step 110 is 1:1. According to some exemplary embodiments, the ratio of the at least one type of protein to the polysaccharide in the composition of step 110 is 100:1. According to some exemplary embodiments, the ratio of the at least one type of protein to the polysaccharide in the composition of step 110 is 50:1. According to some exemplary embodiments, the ratio of the at least one type of protein to the polysaccharide in the composition of step 110 is 25:1.

According to some embodiments, the composition of step 110 comprises at least one type of protein selected from the group consisting of PPI, SPI, or a combination thereof, and a polysaccharide selected from the group consisting of alginate and RGD-modified alginate. Each possibility represents a different embodiment.

According to some embodiments, the at least one type of protein is selected from PPI, SPI, or a combination thereof and the at least one polysaccharide comprises alginate. According to further embodiments, the composition comprises at least one of PPI, SPI, or a combination thereof at a concentration range of about 0.1-10% w/v of the composition, and alginate or RGD-modified alginate at a range of about 0.1-10% w/v of the composition. According to still further embodiments, the composition comprises at least one of PPI, SPI, or a combination thereof at a concentration range of about 0.5-4% w/v of the composition, and alginate or RGD-modified alginate at a range of about 0.5-4% w/v of said composition. According to yet still further embodiments, the composition comprises at least one of PPI, SPI, or a combination thereof at a concentration range of about 0.5-2% w/v of the composition, and alginate or RGD-modified alginate at a range of about 0.5-2% w/v of said composition.

According to some embodiments, the composition of step 110 comprises PPI at a concentration range of about 0.1-5% w/v of the composition, SPI at a concentration range of about 0.1-5% w/v of the composition, and alginate or RGD-modified alginate at a concentration range of about 0.1-5% w/v of said composition.

According to some embodiments, the composition of step 110 is characterized by having a viscosity of no more than $6\times10^7$ mPa. According to some embodiments, the composition of step 110 is characterized by having a viscosity below about $6\times10^7$ mPa. According to some embodiments, the composition of step 110 is characterized by having a viscosity selected from the range of about 0.1 mPa to about $6\times10^7$ mPa. According to some embodiments, the composition of step 110 is characterized by having a viscosity in the range of from about 30 mPa to about $6\times10^7$ mPa.

According to some embodiments, the composition of step 110 comprises porogens materials, configured to undergo degradation and to form pores in the final 3D scaffold, and thereby to increase porosity therein, for future cell growth and maturation applications. The porogens can comprise particles made from various materials, such as for example, polysaccharides and/or proteins. The porogens can comprise meltable gelatin particles. The porogens can comprise oxidized alginate particles, which were previously shown to be susceptible to degradation during satellite cell growth and maturation. Various porogen materials are known in the art (see, e.g., Hwang, C. M. et al., 2010. Biofabrication, 2(3): 035003. DOI:10.1088/1758-5082/2/3/035003; Yeo M. et al., 2016. Biofabrication 16; 8(3):035021. DOI: 10.1088/1758-5090/8/3/035021; Huebsch N. et al., 2015. Nature Materials volume 14, pages 1269-1277).

As used herein, the term "porogen" refers to a material having specified dimensions and structure, used to make pores in the final 3D scaffold of the present invention, after the degradation thereof.

According to some embodiments, the composition of step 110 further comprises at least on additive, preferably an edible additive, selected from but not limited to, emollients, flavors compounds, aromatizing compounds, lipids, colorants, metals, vitamins, mineral salts, combinations thereof, or any other suitable additive known in the art. Each possibility represents a different embodiment. According to some embodiments, the colorants are natural colorants. According to some embodiments, the natural colorants are derived from plants. According to some embodiments, the colorant is selected from the group consisting of apple powder color, beet powder color and a combination thereof.

According to some embodiments, the at least one composition from step 110 can be used as ink for 3D printing processes, for the fabrication of 3D scaffolds, for various uses.

According to certain embodiments, the at least one composition of step 110 comprises edible compounds suitable for non-human-animal cell growth, particularly for the growth of non-human-animal cells. According to the embodiments, the ink is defined herein as "bio-ink". According to certain embodiments, the bio-ink further comprises at least one type of non-human-animal cells. It is to be explicitly understood that the term "bio-ink" as used herein refers to the printable-compositions of the present invention comprising edible compounds, with or without cells. According to some embodiments, the at least one composition from step 110 comprises bio-ink. According to some embodiments, the at least one composition from step 110 comprises non-human-animal cells encapsulated or disposed or dispersed therein.

According to certain embodiments the concentration of the cells within the bio-ink composition is in a range of about $5\times10^3$-$500\times10^6$ cells/ml of the composition. According to some embodiments, the cell concentration is from $1\times10^6$ to $100\times10^6$. According to other embodiments, the cell concentration is about $1\times10^6$, $5\times10^6$, $20\times10^6$, $50\times10^6$, $100\times10^6$, or $500\times10^6$. Each possibility represents a different embodiment. According to these embodiments, the at least one edible member and the 3D scaffold comprising same comprise a plurality of at least one type of animal cell. According to some embodiments, the cells are in the form of 3D cell aggregates.

As used herein, the term "plurality" refers to two or more.

Any type of non-human-animal cells can be used with the printing method of the present invention, depending on the final product to be formed.

According to certain embodiments, the plurality of at least one type of non-human-animal cells comprises bovine cells. According to certain exemplary embodiments, the bovine cells comprise pluripotent stem cells. According to certain embodiments, the pluripotent stem cells are bovine embryonic stem cells. According to some embodiments, the pluripotent stem cells are bovine induced pluripotent stem cells.

According to certain exemplary embodiments, the method of the present invention is employed for the production of a 3D printed nutritious scaffold, comprising at least one type of edible protein, at least one type of edible polysaccharide, and at least one type of a plurality of non-human-animal cells and/or progenitors thereof.

As used herein, the term "progenitor cell" refers to a cell capable of giving rise to differentiated cells in multiple lineages, such as, myoblasts, fibroblasts, adipocytes, stromal cells, fibroblasts, pericytes, smooth muscle cells, and endothelial cells. "Progenitor cells" differ from stem cells in that they typically do not have the extensive self-renewal capacity. According to certain embodiments, a progenitor cell comprises a mesenchymal stem cell (MSC), an embryonic stem cell (ESC), an adult stem cell, a differentiated ESC, a differentiated adult Stem cell, and an induced pluripotent Stem cell (iPSC).

According to certain exemplary embodiments, the method of the present invention is for 3D printing of nutritious scaffolds for the production of cultured meat. According to these embodiments, the plurality of non-human-animal cells comprises at least one type of cells selected from stromal and/or endothelial cells and/or fat cells together with at least one cell type according to the desired final meat product, including muscle cells (meat cuts); hepatocytes (liver); cardiomyocytes (heart); renal cells (kidney); lymphoid and epithelial cells (sweetbread made of thymus and pancreas), neural and neuronal cells (brain); ciliated epithelial (tongue), stomach cells (tripe) and progenitor cells thereof. Each possibility represents a separate embodiment of the invention.

According to certain embodiments, the non-human-animal cells are selected from the group consisting of muscle cells, extracellular matrix (ECM)-secreting cells, fat cells, endothelial cells, and progenitors thereof. Each possibility represents a separate embodiment of the invention. In some embodiments, non-human-animal cells comprise muscle cells or progenitors thereof and at least one additional cell type selected from the group consisting of ECM-secreting cells, fat cells, endothelial cells, and progenitors thereof. Each possibility represents a separate embodiment of the invention. In some embodiments, the non-human-animal cells comprise muscle cells or progenitors thereof, ECM-secreting cells or progenitors thereof, fat cells or progenitors thereof, and endothelial cells or progenitors thereof. Each possibility represents a separate embodiment of the invention.

According to certain embodiments, the non-human-animal is selected from the group consisting of ungulate, poultry, aquatic animals, invertebrate and reptiles. Each possibility represents a separate embodiment of the present invention.

According to certain embodiments, the ungulate is selected from the group consisting of a bovine, an ovine, an equine, a pig, a giraffe, a camel, a deer, a hippopotamus, or a rhinoceros. According to some embodiments the ungulate is a bovine. According to certain exemplary embodiments, the bovine is a cow.

According to certain exemplary embodiments, the at least one composition of step 110 comprises a plurality of at least one type of bovine cells. According to further certain exemplary embodiments, the plurality of cells comprises bovine adipocytes, bovine muscle cells and/or progenitors thereof.

According to some embodiments, the composition of step 110 comprises at least one type of protein, at least one type of polysaccharide, and at least one type of cells. According to further embodiments, the composition comprises: at least one type of protein selected from PPI and SPI at a concentration range of about 0.1-5% w/v of the composition; at least one type of polysaccharide comprising alginate at a concentration range of about 0.1-5% w/v of the composition, and at least one type of non-human-animal cells at a concentration range of about $5\times10^3$-$500\times10^6$ cell/ml of the composition.

According to some embodiments, the method 100 further comprises step 120 of providing a support medium compatible to scaffold fabrication.

In some embodiments, the support medium comprises an edible material. In some embodiments, the support medium comprises a non-toxic material. In some embodiments, the support medium comprises an edible, non-toxic, material. According to some embodiments, the edible material is non-animal derived material.

According to some embodiments, the support medium is in the form of a removable support bath. In further embodiments, the removable support bath is reusable. In certain embodiments, the present invention provides a reusable, removable, support bath comprising the support medium as presented herein, wherein the support medium comprises an edible, non-toxic, non-animal derived material disposed therein.

According to some embodiments, the material contained or comprised within the support medium from step 120 is selected from the group consisting of a hydrogel material, micronized particulates, a thermo-reversible material and any combination thereof. Each possibility represents a different embodiment. According to further embodiments, the material comprised within the support medium from step 120 is in the form of a hydrogel. According to further embodiments, the material comprised within the support medium from step 120 comprises at least one material selected from agar, agarose, gelatin, gellan gum, xanthan gum, gum *arabica*, and any combination thereof. Each possibility represents a different embodiment. According to certain embodiments, the material comprised within the support medium is edible, non-animal derived material compatible to scaffold fabrication.

According to some embodiments, the material contained or comprised within the support medium from step 120 comprises at least one divalent ion selected from the group consisting of calcium ($Ca^{+2}$), magnesium ($Mg^{+2}$), iron ($Fe^{+2}$), salts thereof, combinations thereof, or any other suitable material known in the art. Each possibility represents a different embodiment. According to some embodiments, the divalent ion salt is selected from the group consisting of $CaSO_4$, $CaCl_2$, $MgSO_4$, $FeCl_3$, combinations thereof, or any other suitable material known in the art. Each possibility represents a different embodiment.

According to some embodiments, the at least one divalent ion or the salt thereof is comprised/disposed within the support medium at a concentration range of from about 0.1 to about 20 mM. According to further embodiments, the at least one divalent ion or the salt thereof is comprised within the support medium at a concentration selected from about 0.1 to about 1 mM, about 1 to about 10 mM, or about 10 to about 20 mM. Each possibility represents a different embodiment.

According to some embodiments, the support medium comprises an edible, non-animal derived hydrogel comprising agar microparticles and at least one divalent ion. According to some exemplary embodiments, the support medium comprises an edible, non-animal derived hydrogel comprising agar microparticles and $CaCl_2$ as a crosslinking agent.

According to some embodiments, the method 100 further comprises step 130 of depositing the at least one composition of step 110 into the support medium of step 120 in a predetermined pattern, thereby forming at least one edible member therein. According to some embodiments, the at least one edible member is deposited during step 130 within the support medium in a liquid state and consists of the at least one composition of step 110. In further embodiments, the deposition is performed under conditions configured to enable the transition of the at least one edible member into a solid or semisolid state, thereby enabling to form a 3D scaffold having a predetermined structure. In still further embodiments, the predetermined structure of the scaffold corresponds to the predetermined pattern of the deposition.

In some embodiments, the support medium comprises an edible, non-animal derived hydrogel which is compatible to scaffold fabrication. The term "compatible to scaffold fabrication" as used herein, refers to a support medium being configured to mechanically support the deposition of at least one edible member therein, in order to enable the formation of the 3D scaffold therein.

According to some embodiments, step 130 comprises depositing the at least one aqueous composition of step 110 into the support medium of step 120 in a predetermined pattern, under conditions enabling the transition of the at least one aqueous composition to a solid or semisolid state, thereby forming a 3D scaffold having a predetermined structure, wherein the predetermined structure of the 3D scaffold comprises at least one layer, wherein the at least one layer comprises at least one edible member. In further embodiments, the predetermined structure of the 3D scaffold comprises at least one layer or a plurality of layers, wherein the at least one layer or each layer of the plurality of layers comprises a plurality of edible members, wherein the plurality of edible members can intersect between themselves and/or be arranged in parallel to each other, within the same layer or in different layers, in order to form various predetermined patterns within the 3D scaffold. Thus, the method of the present invention enables to form various 3D scaffolds having various predetermined structures, due to the 3D arrangement of the edible members within the 3D scaffold, during the deposition thereof.

According to some embodiments, during step 130, relative movement is initiated between the support bath and an apparatus configured to deposit the at least one composition of step 110 thereto, thereby forming the predetermined structure of the 3D scaffold therein. In some embodiments, the support bath is stationary during scaffold fabrication, wherein the apparatus configured to deposit the at least one composition of step 110 is configured to perform the relative movement during scaffold fabrication. In some alternative embodiments, the support bath is placed on a moving stage set (e.g., of a 3D printer), configured to perform movement during scaffold fabrication, wherein the apparatus can be movable or stationary.

According to some embodiments, the conditions enabling transition of the at least one edible member to a solid or semisolid state in step 130 comprises exposing said at least one edible member to at least one crosslinking mechanism, thereby causing said edible member to transition from a fluid (e.g., liquid) state to a solid or semisolid state, and forming the 3D scaffold.

As used herein, the term "transition to a solid or semisolid state" refers to the transition of the edible member consisting of the composition of step 110 from a liquid state to a hydrogel state, during and/or following the deposition thereof within the support medium, due to the crosslinking mechanism occurring during step 130, thereby forming the predetermined structure of the 3D scaffold, wherein the predetermined structure of the 3D scaffold comprises at least one layer comprising at least one edible member as disclosed herein. As used herein, the term "solid or semisolid state" refers to a state of a material being in hydrogel formation.

According to some embodiments, the crosslinking mechanism is selected from the group consisting of chemical crosslinking, thermal crosslinking, photopolymerization, enzymatic polymerization, and combinations thereof. Each possibility represents a different embodiment.

According to some embodiments, the chemical crosslinking comprises exposing the at least one edible member to at least one divalent ion selected from the group consisting of calcium ($Ca^{+2}$), magnesium ($Mg^{+2}$), iron ($Fe^{+2}$), salts thereof, and combinations thereof. Each possibility represents a different embodiment. According to some exemplary embodiments, the chemical crosslinking agent is $CaCl_2$.

According to some embodiments, the at least one divalent ion or the salt thereof is disposed or comprised within the support medium of step 120, prior to step 130. According to some embodiments, the at least one divalent ion or the salt thereof is comprised within the support medium at a concentration range of from about 0.1 to about 20 mM, prior to step 130. According to further embodiments, the at least one divalent ion or the salt thereof is comprised within the support medium at a concentration selected from about 0.1 to about 1 mM, about 1 to about 10 mM, or about 10 to about 20 mM. Each possibility represents a different embodiment.

According to other embodiments, the at least one divalent ion or the salt thereof is disposed within a solution added to the at least one edible member, during and/or following step 130. According to further embodiments, the solution comprising the at least one divalent ion or the salt thereof is externally added to the at least one edible member during step 130, and/or following step 130. According to some embodiments, the at least one divalent ion or the salt thereof is disposed within the solution added to the at least one edible member, at a concentration range of from about 50 to about 200 mM. According to further embodiments, the at least one divalent ion or the salt thereof is disposed within the solution added to the at least one edible member, at a concentration ranging from about 50 to about 100 mM, about 100 to about 150 mM, or about 150 to about 100 mM. Each possibility represents a different embodiment. According to some embodiments, step 130 further comprises depositing or pouring a solution on top of the at least one edible member, wherein the solution comprises the at least one divalent ion or the salt thereof as disclosed herein above, and wherein the deposition thereof is provided by performing at least one of dripping, injecting, pipetting, and the like. Each possibility represents a different embodiment.

According to some embodiments, the at least one divalent ion or the salt thereof as disclosed herein above is comprised/contained: (1) within the support medium prior to step 130; and/or (2) within a solution deposited on the at least one edible member during and/or following step 130, thereby enabling the chemical crosslinking thereof and the transition of the at least one edible member from a liquid state to a solid or semisolid state (i.e., hydrogel). According to some embodiments, during step 130, the at least one edible member is deposited within the support medium in a liquid state, wherein the deposition is performed under conditions configured to enable the transition of the at least one edible member from the liquid state into a solid or semisolid state, as disclosed herein above.

According to some embodiments, the concertation of the divalent ion or salt thereof within the solution is constant throughout the crosslinking process. According to some other embodiments, the concertation of the divalent ion or salt thereof within the solution is gradually elevated from the starting time point to the end time point of the crosslinking process during step 130.

According to some embodiments, step 130 comprises depositing the at least one composition of step 110 into the support medium of step 120, thereby forming a plurality of edible members therein. According to some embodiments, step 130 comprises depositing a plurality of edible members within the support medium, wherein each edible member comprises the at least one composition of step 110, thereby forming a 3D scaffold having a predetermined structure therein. In some embodiments, step 130 comprises depositing or stacking a plurality of layers one on top of the other, wherein each layer comprises a plurality of edible members.

According to some embodiments, step 130 comprises depositing the at least one composition of step 110 into the support medium of step 120, thereby forming one or more layers therein, wherein each layer comprises one or more edible members, and wherein the one or more layers forms the predetermined structure of the 3D scaffold. According to further embodiments, the deposition of the composition during step 130 comprises: depositing the predetermined structure material layer by layer in an XY plane, depositing the predetermined structure material layer by layer in an XZ plane, depositing the predetermined structure material layer by layer in an YZ plane, depositing the predetermined structure material in a non-planar configuration (e.g., a curved path), into the support material, or a combination thereof. Each possibility represents a different embodiment.

According to certain embodiments, deposition of the composition during step 130 is performed by 3D printing. The compositions and methods of the present invention provides a platform technology that may be easily adopted for use with an open-source or proprietary 3D Printers. Advantageously, the compositions and methods of the invention enables printing compositions comprising cells while keeping the viability of the cells throughout the printing process.

According to some embodiments, the apparatus configured to deposit the at least one composition of step 110 into the support medium is an extruder or a 3D printer head of a suitable 3D printer. According to some embodiments, during step 130, the deposition of the at least one composition of step 110 into the support medium of step 120 in a predetermined pattern is performed using an extruder or a 3D printer head that is at least partially inserted into the support medium, wherein the extruder moves within the support medium and extrudes or injects or deposits the at least one edible member at least partially within the support medium. In further such embodiments, the extruder is inserted fully into the support medium and extrudes the at least one edible member within the support medium.

The term “predetermined pattern” as used herein, refers to the movement of the extruder within the support medium during the extrusion of the at least one edible member therefrom, wherein the extruder moves in a specific or predetermined pattern to form the corresponding predetermined structure of the resulting 3D scaffold.

According to some embodiments, the extruder or a 3D printer head extrudes the at least one composition into the support medium in a liquid state, thereby forming at least one edible member therein, wherein the extrusion is performed under conditions enabling the transition of the at least one edible member from the liquid state into the solid or semisolid state, as disclosed herein above.

According to some embodiments, each edible member is an extruded member. In further embodiments, each extruded member is edible.

The terms “extrusion” or “extruded”, as used herein, refers to a process of forcing the at least one composition from step 110 through a corresponding at least one die orifice (i.e., the extruder’s nozzle or head or needle), thereby forming at least one extruded member. The die orifice has a desired cross-sectional shape corresponding to the desired shape of the extruded member. Said process of forcing the composition of the present invention through the die orifice is typically performed under a relatively low printing pressure, a volumetric flow-rate matching the movement speed of the extruder, and a temperature appropriate to maintain live cells.

As used herein, the term “volumetric flow-rate” refers to the flow rate of which the composition is forced through the die orifice.

As used herein, the term “printing pressure” refers to the pressure applied on the composition and optionally the cells contained therein during the process of forcing the composition through the die orifice during printing.

According to some embodiments, the 3D printing process during step 130 of forcing the at least one composition from step 110 through a corresponding at least one die orifice is performed under at least one printing condition selected from: a printing pressure selected from the range of about 0.1-20 psi, extruder movement speed selected from the range of about 0.1-50 mm/sec, a temperature selected from the range of about 4-37° C., and combinations thereof. It should be understood that printing conditions such as printing pressure and/or extruder movement speed may vary according to the 3D printer type and/or die orifice diameter/shape, and therefore different values than the ones specified above may be included.

According to some embodiments, the process of forcing the at least one composition from step 110 through a corresponding at least one die orifice is performed under at least one condition selected from: printing pressure selected from the range of about 2-10 psi, extruder movement speed selected from the range of about 15-35 mm/sec, a temperature selected from the range of about 4-37° C., and combinations thereof. According to a specific embodiment, the 3D printing process during step 130 of forcing the at least one composition from step 110 through a corresponding at least one die orifice is performed under the following printing conditions: a pressure selected from the range of about 4-9 psi, extruder movement speed selected from the range of about 20-30 mm/sec, and a temperature selected from the range of about 4-37° C. Advantageously, the bio-ink compositions of the present invention enable forcing said bio-ink composition through the die orifice at the printing conditions as disclosed above, that enable to maintain the viability of non-human-animal cells, when disposed therein.

As used herein, the terms “extruded member” or “edible member” are interchangeable, and refers to the formed material within the support medium, resulting from the deposition/extrusion of the at least one composition of step 110 through the nozzle into the support medium. The deposition, typically by extrusion of the at least one composition of step 110 within the support medium in a predetermined pattern, forms the at least one edible member composed of said composition, therein. In a preferred embodiment, the edible member is an edible member. It is to be explicitly understood that the member may or may not comprise non-human-animal cells.

According to some embodiments, the die orifice has a cross-sectional shape selected from a circle, square, ellipse, rectangle, triangle, or any other suitable curvilinear shape or polygon known in the art. The shape of the die orifice is typically dependent on the 3D printer type, and affects the resulting cross-sectional shape of the at least one extruded member.

According to some embodiments, the die orifice is circle-shaped and has an inner diameter selected from the range of 0.1 to 1.5 mm. According to further embodiments, the die orifice has an inner diameter selected from the range of 0.1 to 0.5 mm, 0.5 to 1 mm, or 1 to 1.5 mm. Each possibility represents a different embodiment. According to some embodiments, the at least one extruded member has a circle-shaped cross section, and a diameter of the at least one extruded member along said cross section is selected from the range of 0.1 to 1.5 mm. According to further embodiments, the diameter of the at least one extruded member is selected from the range of 0.1 to 0.5 mm, 0.5 to 1 mm, or 1 to 1.5 mm. Each possibility represents a different embodiment. It should be understood that the shape and/or diameter of the die orifice and/or extruded member may vary according to the 3D printer type and die orifice geometry, and therefore different values than the ones specified above may be included.

According to some embodiments, the extrusion of the composition during step 130 is performed by 3D printing, wherein the die orifice is a movable printer extruder head (i.e., the nozzle). The path of the printer head extruding the protein-polysaccharide composition of step 110, optionally further comprising non-human-animal cells disposed therein, into the support medium, can be designed to form any predetermined pattern, resulting in the predetermined structure of the 3D scaffold comprising the cells encapsulated therein, as may be suitable for the formed 3D scaffold according to its intended use. The predetermined structure of the 3D scaffold can be pre-designed utilizing various known computer modeling software used to design various possible predetermined patterns.

According to some embodiments, during step 130, the 3D printer's extruder head is displaced or moved within the support medium, thereby extruding a plurality of layers one on top of the other, wherein each layer comprises a plurality of edible members. The plurality of edible members within the same layer or within different layers may form various patterns, enabling to form various predetermined structures of the 3D scaffold.

According to some alternative embodiments, the extrusion of the composition at step 130 is performed manually, utilizing a syringe-based extruder, such as for example, a pipette.

According to some other alternative embodiments, the deposition during step 130 of the at least one composition of step 110 into the support medium, is performed by injecting or extruding the composition into a mold-based support medium, thereby forming the at least one edible member therein. In further embodiments, the injection or extrusion is performed under the conditions configured to enable the transition of the at least one edible member into a solid or semisolid state as presented herein, and to conform to the shape of the mold-based support medium, thereby forming a 3D scaffold having a predetermined structure therein. In some such embodiments, the mold-based support medium is characterized by having an inner predetermined pattern/design, corresponding to the desired predetermined structure of the 3D scaffold formed therein. In some such embodiments, the mold-based support medium is a unitary 'one-piece' mold, or can optionally consist of at least two detachable portions, which forms the inner predetermined pattern/design of the mold therebetween, when attached to each other.

According to some embodiments, the support medium may comprise microparticles, that may act as a Bingham plastic or Herschel-Buckley fluid, during the 3D printing process. As an extruder head moves through the support medium, the support medium shear thins and offers little mechanical resistance, yet the composition being extruded out of the extruder head and deposited within the support medium is held in place. The extruder head moves through the support medium fast enough that the extruder head generates a shear stress above a threshold shear force, and therefore sees the support medium as a fluid. In contrast, the 3D scaffold material (i.e., the composition from step 110) deposited out of the extruder head has a shear stress below the threshold shear force, and therefore sees the support medium as a solid material, and thus stays where it is deposited. Thus, a 3D printer can lower an extruder head into the support medium, generate relative movement therebetween, and deposit the edible or extruded members in various 3D geometries/patterns. The extruded members stay in place once the extruder head moves away, due to the characteristics of the support medium which is compatible to scaffold fabrication as disclosed above, and due to the crosslinking mechanism as disclosed herein above, thus forming the predetermined structure of the 3D printed scaffold as disclosed herein. Once the complete 3D scaffold is printed and the predetermined structure thereof has sufficiently assembled, the support medium is removed therefrom in a non-destructive manner, as will be disclosed herein below in step 140.

According to some embodiments, step 130 comprises at least partially inserting an extruder into the support medium and extruding at least partially the at least one extruded member comprising the at least one composition of step 110, within the support material, thereby forming the 3D scaffold as disclosed hereinabove. In further embodiments, the support medium comprises at least one divalent ion or the salt thereof disposed therein (i.e., a 'crosslinking agent'), as disclosed herein above, configured to initiate the crosslinking process of the at least one composition of step 110. In still further embodiments, the solution comprising the at least one divalent ion or the salt thereof is externally added to the extruded member, during the extrusion thereof and the formation of the 3D scaffold within the support medium. In yet still further embodiments, the concertation of the divalent ion or salt thereof within the solution is constant throughout the crosslinking process. In other alternative embodiments, the concertation of the divalent ion or salt thereof within the solution is gradually elevated from the starting time point to the end time point of the crosslinking process during step 130, thereby affecting the properties of the final crosslinked 3D scaffold and the structure thereof.

The type and/or concentration of the crosslinking agent (i.e., the at least one divalent ion or the salt thereof) may vary along the transition of the 3D scaffold to a solid or semi-solid state, according to the desired mechanical properties of the printed scaffold. For example, when the at least one composition from step 110 comprises PPI-Alginate, the crosslinking during step 130 may be performed with a first stage of crosslinking with low-concentration of calcium to allow smooth printing without the extruder's nozzle clogging. This can be followed by a second stage of enhanced crosslinking with higher calcium concentrations to saturate ionic crosslinking. This can be followed by a third finalizing stage of crosslinking, using a Genipin component as an additional chemical crosslinker or using transglutaminase as enzymatic crosslinker to enhance further the crosslinking and the mechanical properties of the scaffold.

According to some embodiments, step 130 comprises inserting the extruder into the support medium and extruding the at least one composition of step 130 thereto, wherein the composition comprises at least one type of protein selected from the group consisting of PPI, SPI, or a combination thereof and at least one polysaccharide selected from alginate and/or RGD-modified alginate, and wherein the support medium comprises agar and a crosslinking agent (i.e., divalent ions). Without wishing to being bound to any theory on mechanism of action, it is contemplated that PPI and/or SPI can crosslink in the presence of alginate and to form hydrogels, under the presence of calcium ions (termed 'cold-set' gelation) within the support bath. The agar mechanically supports the crosslinking hydrogel. Therefore, according to some embodiments, the present method enables the transition of the extruded members from a fluid state to a solid or semi-solid state, during and/or following the extrusion thereof, wherein the support medium includes a crosslinking agent configured to cause the extruded members to transition from the fluid to the solid or semi-solid state during the extrusion thereof, thereby enabling formation of the 3D scaffold of the present invention. Alternately and/or additionally, according to some embodiments, a solution comprising the crosslinking agent can be externally added to the extruded members, during and/or after the deposition thereof into the support bath.

International Application Publication No. WO 2020/030628 discloses 3D printing of edible viscoelastic micro-extruded elements, comprising high weight percentages of proteins and edible pseudoplastic polymers. The high amounts of proteins and/or polymers can affect the final product's characteristics, due to their effect when undergoing deformation, i.e., during the extrusion/printing thereof. It is contemplated that the extrusion of such highly viscous materials can affect the resulting final 3D structure of the scaffold, and optionally prevent the fabrication of delicate complex structures. Moreover, the viscous solutions may not be preferable for cellular printing, and may negatively affect the cell viability and characteristics. In contrast, the compositions and methods of the present invention enable the printing of 3D scaffolds, particularly edible scaffolds, with relatively low amounts of proteins and polysaccharides not originated from the animal cells to be cultured thereon/therewithin, resulting in relative low viscosity of the composition, thereby enabling the production of high-quality cultured tissue products, and particularly cultured meat products.

Without wishing to being bound to any theory on mechanism of action, it is contemplated that the utilization of the protein within the composition in a range of about 0.1-15% w/v enables the production of a high-quality scaffold, particularly edible scaffold having improved organoleptic properties and nutritional values, useful for cultured meat applications.

Advantageously, it is contemplated that the combination between: (1) the composition of step 110 comprising a protein and/or a polysaccharide, each in a range of about 0.1-15% w/v (or 0.1-15% w/w) of the composition of the present invention; (2) the utilization of the support baths as disclosed herein for 3D printing applications, and (3) the printing conditions as disclosed herein above, can enable the delicate 3D printing process thereof, resulting in the fabrication of delicate and complex 3D structures, beneficial for improved growth and spread of seeded cells thereon and/or therewithin, and for cellular viability and function, due to the relative low viscosity of the composition.

Additionally, the presently claimed 3D-fabrication method could be applied to produce 3D scaffolds in a delicate and cell-friendly manner, wherein the utilization of the composition containing non-human-animal cells disposed therein as bio-ink prior to printing, having a low viscosity (due to protein and/or polysaccharide content below about 15% w/v of the composition), enables the useful fabrication of more biologically-complex 3D scaffolds containing cells. The fabrication method relies on the ability of the low viscosity composition of step 110 to crosslink upon calcium diffusion from the removable support bath during fabrication, thus avoiding more severe protein extrusion techniques which rely on the extrusion of high viscosity protein compositions, which are not suitable to maintain cell viability within the protein compositions during the extrusion thereof.

When cells are mixed in the composition prior to printing, a crucial parameter for maintaining cell viability is the shear-stress applied on the cells during printing. The amount of shear stress exerted on the cells during printing depends on the rheological properties of the composition (i.e., the viscosity thereof), and on the different printing parameters such as: printing pressure (i.e., the pressure applied on the composition and the cells during the process of forcing the composition through the die orifice), printing temperature, nozzle or die orifice speed (i.e. extruder movement speed), nozzle or die orifice inner diameter, and nozzle or die orifice geometry (i.e., shape).

Herein, the present inventors have shown that the cells contained within the composition prior to printing appear to be alive and functioning after printing in all cellular printing trials, as can be seen in the example section below. Without wishing to be bound by any specific theory or mechanism of action, this is attributed mainly to the low viscosity of the compositions of the present invention (due to protein and/or polysaccharide content below about 15% w/v of the composition) which reduces the potential shear-stress applied on the cells during printing, in advance. Furthermore, to maintain cell viability, the 3D printing process during step 130 was performed under the printing conditions as disclosed herein above, including: temperature selected from the range of about 4-37° C., extruder movement speed selected from the range of about 0.1-50 mm/sec, and printing pressure selected from the range of about 0.1-20 psi.

Furthermore, one of the key challenges of cultivated meat production is enabling sufficient material transfer within thick tissue scaffolds, essential for tissue survival. Thus, the production of cultivated meat which aims to mimic fresh meat, is a far more challenging goal than the preparation of finely minced or ground meat products (M. J. Post, et al., Scientific, sustainability and regulatory challenges of cultured meat, Nat. Food. 1, pp 403-415, 2020). Therefore, it is contemplated in some embodiments, that 3D printing of cells disposed within the composition of step 110 inherently creates an even distribution of cells throughout the fabricated 3D printed scaffold. In this manner, the methods of the present invention allow for an even, dense cell distribution throughout the fabricated scaffolds presented herein. Thus, 3D printing of cells as disclosed herein above can be beneficial for bypassing cell-seeding challenges common to other methodologies, where cells are seeded after scaffold preparation.

According to some embodiments, the fabrication of such 3D scaffolds based on the compositions of the present invention is based on the use of support baths, preferably comprising agar. The utilization of agar can be advantageous, since it has a low cost, and is an edible, non-animal derived product. Agar may further be reusable since it may be mechanically removed from the printed 3D scaffolds, in contrast to thermal removal methods (e.g., heating or cooling the support medium to dissolve or melt it) used for other bath types like gelatin-based materials. Hence, the concept of using Agar or other similar materials, as more sustainable, reusable support baths intended for 3D-printing cultured meat is advantageous.

According to some embodiments, providing at least one composition during step 110 comprises providing a plurality of compositions. According to further embodiments, the plurality of compositions can be extruded by a corresponding plurality of extruders, during step 130. According to further embodiments, providing a plurality of compositions during step 110 comprises providing a first composition and a second composition, wherein each of the first and the second composition comprises at least one type of protein at a concentration range of about 0.1-15% w/v of the composition, and at least one type of polysaccharide.

According to some embodiments, the first and the second compositions, each comprises a different combination and/or concentration of the at least one type of protein and the at least one type of polysaccharide, and optionally at least one type of non-human-animal cells. When cells are present, the composition may further comprise materials/combinations supporting cell anchorage and attachment. According to some embodiments, the first composition comprises alginate and PPI and/or SPI, each in a concentration selected from the range of 0.1-10% w/v, and adipocyte cells. According to further embodiments, the first composition comprises alginate-PPI in a concentration of 1% w/v-2% w/v of the composition, and adipocyte cells. According to some embodiments, the second composition comprises RGD-modified alginate and PPI and/or SPI, each in a concentration selected from the range of 0.1-10% w/v, and satellite cells (SCs) in a concentration selected from the range of 1-500 Million cells/ml. According to further embodiments, the second composition comprises RGD-modified alginate-PPI in a concentration of 1% w/v-1% w/v of the composition, and $50\times10^6$ cells/ml of SCs. According to certain exemplary embodiments, the adipocytes and/or the satellite cells are bovine cells.

According to some embodiments, the first and the second compositions further comprise at least one type of porogen.

According to some embodiments, the first and the second compositions can have different additives, such as for example, different color additives (i.e., colorants).

According to some embodiments, during step 130 the first and second compositions are simultaneously extruded by a first and second extruders, respectively, at least partially into the support medium.

According to some embodiments, the utilization of the first and the second compositions enables to form 3D scaffolds having various portions with different characteristics, such as different Young's modulus, different elasticity, etc. The specific characteristics of each scaffold portion may affect the anchorage, attachment, differentiation and/or maturation of each of the cell types comprised with the compositions or seeded on the printed 3D scaffold. According to some embodiments, the first composition comprises a higher concentration of the protein and/or the polysaccharide, compared to the second composition. In further such embodiments, following the crosslinking during step 130, the first composition transitions into a first hydrogel, while the second composition transitions into a second hydrogel. In further embodiments, the first hydrogel is more rigid compared to the second hydrogel, due to its higher protein and/or the polysaccharide content. In further optional embodiments, the first hydrogel has a higher Young's modulus compared to the second hydrogel, due to its higher protein and/or the polysaccharide content.

According to some embodiments, the resulting 3D scaffold fabricated according to the present method is characterized by having a first rigid portion of the extruded members, cause by the first hydrogel, and a second softer portion of the extruded members which are caused by the second hydrogel. In yet still further such embodiments, the 3D scaffold comprises a plurality of layers, wherein each layer comprises a plurality of extruded members comprising the first and second hydrogels. According to certain exemplary embodiments, the rigid first portions can enable to provide mechanical structure support to the 3D scaffold, while the softer second portions can enable to provide enhanced support for cell growth and spread thereon and/or therewithin. Additionally, the first and second hydrogels can have different colors, thus optionally enabling to mimic meat-like mechanical properties, such as meat resemblance.

It is to be understood that the first and the second compositions may comprise other types of cells, and/or other protein-polysaccharide ratios, thus resulting in the transition of both compositions (following the crosslinking of step 130) into rigid hydrogel, softer hydrogel, or various combinations of rigid-softer hydrogels. According to some embodiments, providing a plurality of compositions during step 110 comprises providing the first composition, the second composition, and optionally additional compositions, wherein all compositions may have various protein-polysaccharide ratios and/or comprise various types of cells.

According to some embodiments, the predetermined structure of the 3D scaffold formed during step 130 comprises at least one layer comprising at least one edible member. According to some embodiments, the predetermined structure comprises a plurality of layers stacked one over the other, wherein each layer comprises at least one edible member. In further embodiments, each layer comprises a plurality of edible members. According to some embodiments, each layer comprises a plurality of parallel edible extruded members. According to some embodiments, the predetermined structure comprises a plurality of layers, optionally parallel to each other, and vertically stacked one on top of the other, thereby forming the 3D scaffold.

According to some embodiments, the predetermined structure of at least one layer comprising a plurality of extruded members of the 3D scaffold comprises a plurality of intersecting polygons. In such embodiments, the extruded members are deposited during step 130 in a manner which forms intersecting polygons shapes. According to further embodiments, the structure of at least one layer comprising a plurality of extruded members of the 3D scaffold is selected from a honeycomb structure/pattern, parallel lines structure/pattern, grid structure/pattern, and combinations thereof. Each possibility represents a different embodiment. According to further embodiments, the extruded members within at least one layer are intersected with each other so as to form a structure/pattern selected from a grid and a honeycomb structure. According to other embodiments, the extruded members within at least one layer are aligned in parallel to each other.

According to some embodiments, the predetermined structure of the 3D scaffold comprises a plurality of layers, wherein consecutive layers are spaced from each other, forming inter-layer spaces within the predetermined structure. The inter-layer spaces can be referred to as voids between the consecutive layers. According to certain embodiments, the consecutive layers are spaced from each other by at least one spacing element. In further embodiments, consecutive layers are spaced from each other by a plurality of spacing elements. In some embodiments, the spacing element comprises at least one additional extruded member. In further embodiments, the spacing element comprises a plurality of additional extruded members. In some embodiments, said additional extruded members are positioned between consecutive layers of the 3D scaffold, optionally at a different angle relative thereto, thereby spacing between consecutive layers to form voids therein. According to certain additional embodiments, the consecutive layers are spaced from each other by depositing a consecutive layer with a slight location shift compared to the previous layer in a direction which is perpendicular to the members' direction. Advantageously, according to some embodiments, the formation of such inter-layer spaces or voids can optionally enable a 3D edible scaffold to mimic meat-like mechanical properties, such as in terms of inner fibrous texture of the scaffold. Additionally, the formation of such inter-layer spaces or voids can optionally enable enhanced growth medium flow therethrough and nutrient availability to cells, thus promoting cell growth and spread within the scaffold.

According to some embodiments, the predetermined structure of the 3D scaffold comprises a plurality of layers, wherein each layer comprises a plurality of extruded members, wherein the extruded members within consecutive layers are aligned in different directions, thereby forming different extruded member orientations therebetween. The different direction alignment can be also referred to as a "shift" between extruded members within consecutive layers. For example, according to some embodiments, the 3D scaffold comprises a first layer comprising a plurality of extruded members aligned in the same direction and in parallel to each other. According to further such embodiments, the 3D scaffold comprises a second layer attached to the first layer, wherein the second layer comprises a plurality of parallel extruded members, aligned perpendicularly to the alignment of the extruded members of the first layer. In still further such embodiments, the 3D scaffold comprises additional layers, each layer comprising a plurality of parallel extruded members aligned perpendicularly relative to the alignment of the extruded members within the previous or consecutive layer.

According to some embodiments, the 3D scaffold comprises a plurality of parallel layers, wherein each layer comprises a plurality of extruded members. In further such embodiments, a first portion of the extruded members are aligned in the same direction and in parallel to each other. In still further embodiments, a second portion of the extruded members are aligned in a different direction relative to the first portion of extruded members, in the same layer and/or between consecutive layers, thereby forming various inner patterns within the same layer and/or between consecutive layers of the 3D scaffold. In still further such embodiments, the 3D scaffold comprises additional portions of the extruded members which are aligned in different directions relative to each other, thereby forming a plurality of inner patterns therein, within the same layer and/or between consecutive layers. Advantageously, according to some embodiments, said inner patterns can optionally enable a 3D edible scaffold to mimic meat-like mechanical properties, such as in terms of meat resemblance, integrity, deformability, elasticity, inner fibrous texture of the scaffold, and the like.

According to some embodiments, the first and second portions of the extruded members are characterized by having the same member properties, such as having the same protein-polysaccharide composition within each member. Moreover, the first and second portions of the extruded members can have the same color, such as for example, both portions can be red.

According to some alternative embodiments, the first and second portions of the extruded members are characterized by having different properties, such as by having a different protein-polysaccharide composition within each member. Moreover, the first and second portions of the extruded members can have different colors, such as for example, the first portion can be red and the second portion can be white. Advantageously, according to some embodiments, said different properties can optionally enable the 3D edible scaffold to mimic meat-like mechanical properties, such as in terms of meat resemblance, integrity, deformability, elasticity, inner fibrous texture of the scaffold, and the like.

According to some embodiments, the 3D scaffold comprises a plurality of layers, wherein each layer comprises a plurality of elongated extruded members aligned in the same direction in parallel to each other, wherein the layers are vertically stacked one on top of the other and are spaced apart from each other. It is contemplated that such a configuration of the 3D scaffold is advantageous, since it is able to facilitate a formation of a multi-layer expansion in the form of a 3D multi-layer structure of muscle fibers, wherein the muscle fibers adhere to the 3D scaffold and/or to each other to form connected muscle multi-layer fibers. This is possible due to the elongated and parallel configuration of the extruded members, which resembles the orientation of muscle fibers of skeletal muscles of a variety of animals. According to certain exemplary embodiments, said 3D scaffold is edible.

As used herein, the term "elongated" refers to a member or a scaffold having a long dimension and a short dimension, wherein the long dimension thereof (e.g., length) is greater than the short dimension (e.g., width or diameter) thereof. For example, the length of an elongated extruded member may be at least three times, at least five times, at least ten times, or more, greater than of the width or diameter thereof.

According to some embodiments, the predetermined structure of the 3D scaffold comprises a plurality of layers, wherein each layer comprises a plurality of extruded members, wherein the extruded members within the same layer are spaced from each other, thereby forming inner-layer spaces. As used herein, the terms "inner-layer spaces", "inner-layer voids" and "inner-layer channels" are interchangeable, and refers to spaces between adjacent extruded members within the same layer of the 3D scaffold of the present invention. According to further embodiments, each layer comprises a plurality of elongated extruded members spaced from each other by elongated inner-layer channels.

According to some embodiments, the predetermined structure of the 3D scaffold comprises a plurality of layers, wherein each layer comprises a plurality of edible members, wherein the plurality of edible members are intersected between themselves and/or are arranged in parallel to each other within the same layer or in different layers, wherein consecutive layers are spaced from each other to form voids therebetween, and wherein edible members within the same layer are spaced from each other, thereby forming channels therebetween.

As was disclosed herein above, one of the key challenges of cultivated meat production is enabling sufficient material transfer within thick tissue scaffolds, essential for tissue survival. Advantageously, according to some embodiments, the formation of the inner-layer spaces/channels and/or inter-layer spaces/voids as disclosed herein above can enable the 3D edible scaffold to mimic meat-like mechanical properties, such as in terms of at least one of meat resemblance, integrity, deformability, elasticity, inner fibrous texture of the scaffold, and the like. Additionally, the formation of spaces/channels/voids between consecutive layers and/or consecutive edible members within the same layer, can enable enhanced and sufficient material (e.g., growth medium) flow therethrough and nutrient availability to cells, thus promoting cell growth and spread thereon within thick tissue scaffolds.

According to some embodiments, the predetermined structure of the 3D scaffold comprises a plurality of layers, wherein each layer comprises a plurality of extruded members. In further such embodiments, within the same layer, the extruded members are spaced from each other by inner-layer spaces. In still further such embodiments, within the same layer, various portions of the extruded members are aligned in different directions relative to one another. In yet still further such embodiments, within the same layer, various portions of the extruded members comprise different protein-polysaccharide compositions. In some such embodiments, the extruded members within consecutive layers are aligned in different directions and are spaced from each other, thereby forming different extruded member orientations and inter-layer spaces therebetween.

According to some embodiments, the predetermined structure of the 3D scaffold comprises a plurality of layers, wherein each layer comprises a plurality of extruded members. In further embodiments, at least one extruded member comprises a core-shell structure, comprising an inner core and an outer shell encompassing said core. In further such embodiments, a plurality of extruded members within each layer comprises the core-shell structure. In still further embodiments, each layer comprises a first plurality of core-shell extruded members each comprising the core-shell structure, and a second plurality of continuous extruded members devoid of the core-shell structure.

According to some embodiments, said core is a hydrogel comprising RGD-modified alginate and PPI and/or SPI, each in a concentration selected from the range of 0.1-15% w/v, and optionally non-human-animal cells in a concentration selected from the range of 1-500 Million cells/ml. According to certain embodiments, the non-human-animal cells are bovine satellite cells (BSCs). In some embodiments, the core is a hydrogel comprising collagen and/or hyaluronic acid, and optionally bovine satellite cells (BSCs) in a concentration selected from the range of 1-500 Million cells/ml. In further embodiments, the core comprises a non-gelling hyaluronic-acid solution serving as an inner, liquid, bio-degradable, cell-carrier material, further comprising BSCs.

According to some embodiments, the shell is a hydrogel comprising alginate in a concentration selected from the range of 0.1-5% w/v, PPI and/or SPI each in a concentration selected from the range of 0.1-15% w/v, and optionally Bovine mesenchymal stem cells (BMSCs) in a concentration selected from the range of 1-500 Million cells/ml. In other alternative embodiments, the BMSCs are present in other extruded members which do not comprise the core-shell structure.

According to some embodiments, the core-shell structure is achieved by a coaxial extrusion of the core within the shell, utilizing a coaxial extruder head optionally made from at least two coaxial nozzles, configured to ensure that the core exits at the geometric center of the shell in a coaxial configuration. In some such embodiments, the coaxial extrusion enables to form a core-shell structure of at least one extruded member, wherein the shell is made from a rigid hydrogel configured to provide mechanical structure support to the 3D scaffold, and the core is made from a softer hydrogel configured to provide enhanced support for cell growth and spread thereon and/or therewithin. In some alternative embodiments, the coaxial extrusion enables to form a core-shell structure of at least one extruded member, wherein the shell forms hollow tubes configured to enable enhanced growth medium flow therethrough and nutrient availability to cells, thus promoting cell growth and spread thereon. The hollow tube structures made by coaxial printing, could further aid in nutrient transfer by diffusion into neighboring members which contain cells, very similarly to a natural vascular network. The hollow tubes can further comprise nutrients/growth aiding factors, which may be in the form of slow-release and/or sustained release formulations. The shell structure may be formed with or without cells. Temporary removable/dissolvable/non-gelling core materials could be used to create the hollow tubes, such as hyaluronic acid, pectin, carrageenan, guar gum, xanthan gum, recombinant gelatin, Pluronic F-127, PVA, Butenediol vinyl alcohol (BVOH), etc.

According to some embodiments, the core-shell structure of the scaffold achieved by coaxial extrusion can enable the fabrication of the inner-layer spaces/channels, thus enabling sufficient material transfer through the scaffold to promote cell growth and spread thereon preferably within thick tissue scaffolds.

According to some embodiments, the predetermined structure of the 3D scaffold following step 130 is configured to resemble a muscle tissue (e.g., a steak, when the scaffold is edible).

According to some embodiments, the 3D scaffold has an elongated predetermined structure, wherein a long dimension of the scaffold (i.e., length) is in the range of about 50 μm to about 100 cm, or more. In further embodiments, the long dimension of the scaffold is in the range of about 50 μm to about 100 μm, about 100 μm to about 1 mm, about 1 mm to about 50 mm, about 50 mm to about 1 cm, about 1 cm to about 50 cm, about 50 cm to about 100 cm, or more. Each possibility represents a different embodiment. In further embodiments, the long dimension of the scaffold is below about 50 μm or optionally greater than 100 cm.

According to some embodiments, the method 100 further comprises step 140 of separating or removing the support medium from the solid or semisolid 3D scaffold formed during step 130, in order to release it therefrom. In further embodiments, the 3D scaffold is edible.

According to some embodiments, step 140 of separating or removing the support medium from the solid or semisolid 3D scaffold can be performed by thermal removal methods, such as heating or cooling the support medium in order to dissolve or melt it, thereby removing it from the 3D scaffold. In further embodiments, additional techniques for removing the support medium include vibration, irradiation with ultraviolet, infrared, or visible light, or application of a constant or oscillating electric or magnetic field. Each possibility represents a different embodiment.

According to some exemplary embodiments, step 140 of separating or removing the support medium from the solid or semisolid 3D scaffold is performed by mechanical methods, such as by gentle pipetting. According to further such embodiments, step 140 of separating or removing the support medium from the solid or semisolid 3D scaffold is performed manually, utilizing standard laboratory equipment, such as by manual gentle pipetting.

Advantageously, it is contemplated, that mechanical removal methods of the support medium comprising agar from the 3D scaffold, may enable to maintain complex and delicate predetermined structures of the 3D scaffolds of the present invention.

Additionally, following the removal of a support medium comprising agar from the 3D scaffold, the support medium may be reusable, since it may be mechanically removed from the printed 3D scaffolds, in contrast to thermal removal methods in which the support medium melts during the removal thereof. Hence, the concept of using agar or other similar materials, as more sustainable, reusable support baths intended for 3D printed scaffolds is advantageous. In addition, in some embodiments, the support medium is devoid of animal-derived components (unlike like gelatin-based support baths, which are animal-derived).

According to some embodiments, the 3D scaffold is characterized by having a Young's modulus in the range of about 0.1 kPa to 1 MPa. According to further embodiments, the Young's modulus is in the range of about 1 kPa to 75 kPa. According to still further embodiments, the Young's modulus is in the range of about 5 kPa to 50 kPa. According to yet still further embodiments, the Young's modulus is in the range of about 5 kPa to 25 kPa. According to a certain embodiment, the Young's modulus is in the range of about 5 kPa to 10 kPa. It is contemplated, that such values of the Young's modulus as disclosed herein above, can correlate to an elastic 3D scaffold which could be preferable when aiming to design a scaffold with characteristics close to those of native muscle tissue, for cultured meat applications.

According to some embodiments, the 3D scaffold fabricated by the present method is in a form of a hydrogel, comprising a plurality of layers, vertically stacked one on top of the other.

According to some embodiments, step 140 of separating or removing the support medium comprises a combined crosslinking and extraction from the agar support bath process, wherein the support medium comprising the 3D scaffold formed therein is immersed within an aqueous crosslinking solution. In further embodiments, said solution comprises at least one divalent ion or the salt thereof as disclosed herein above, configured to perform a final crosslinking of the 3D scaffold, while gentle pipetting is simultaneously performed in order to remove the support medium from the scaffold. According to further embodiments, the at least one divalent ion or the salt thereof is disposed within the solution at a concentration range of from about 50 to about 200 mM. In further exemplary embodiments, the at least one divalent ion or the salt thereof is comprised within the solution at a concentration range of 100 mM. In further embodiments, the 3D scaffold is edible.

According to some embodiments, following step 140, the method further comprises placing the edible 3D scaffold comprising a plurality of at least one type of non-human-animal cells disposed therein under growth conditions, enabling proliferation and/or differentiation and/or maturation of the plurality of at least one type of non-human-animal cells to form at least one type of tissue, thereby producing a cultured tissue product. In specific embodiments, the cultured tissue product is a cultured meat product.

In further embodiments, the cultured meat product comprises fat cells and/or tissue and muscle cells and/or tissue. According to some embodiments, the cultured meat further comprises endothelial cells that may enable the formation of blood vessels.

According to some embodiments, following step 140, the 3D scaffold comprising a plurality of at least one type of non-human-animal cells is not subjected to freeze drying, in order to maintain cell viability within the scaffold. According to some embodiments, following step 140, method 100 does not include freeze drying the 3D scaffold.

According to some embodiments, the method of the present invention enables to fabricate a 3D edible scaffold in a form of a hydrogel, comprising at least one layer comprising at least one edible extruded member, wherein each extruded member comprises a composition comprising at least one protein at a concentration range of about 0.1-10% w/v of the composition, at least one polysaccharide at a concentration range of about 0.1-10% w/v of the composition, and optionally at least one type of non-human-animal cells at a concentration range of about $5\times10^3$-$500\times10^6$ cell/ml of the composition.

According to some embodiments, there is provided a 3D edible scaffold comprising a plurality of at least one type of non-human-animal cells as disclosed herein above, fabricated by the method of the present invention. According to further embodiments, the 3D edible scaffold comprises a plurality of layers, wherein each layer comprises a plurality of extruded members. According to still further embodiments, each member comprises at least one hydrogel, wherein the hydrogel comprises the at least one composition as disclosed herein above. According to yet still further embodiments, the composition comprises at least one protein at a concentration range of about 0.1-15% w/v of the composition, at least one polysaccharide at a concentration range of about 0.1-5% w/v of the composition, and at least one type of non-human-animal cells at a concentration range of about $5\times10^3$-$500\times10^6$ cell/ml of the composition.

The 3D edible scaffold as presented herein can be used in growing a 3D nutritious engineered edible tissue, intended for cultured meat applications.

According to some alternative embodiments, the method 100 optionally comprises step 150 of freeze drying the 3D scaffold, thereby forming a freeze-dried porous 3D scaffold, preferably wherein the at least one composition from step 100 is devoid of cells. According to certain such embodiments, the freeze-dried porous 3D scaffold has a porosity in the range of about 50%-95%, out of the total volume of the 3D scaffold.

According to some embodiments, following step 150 of freeze drying the 3D scaffold, the method further comprises seeding the freeze-dried 3D scaffold with a plurality of at least one type of cells, and placing the scaffold under growth conditions enabling differentiation and/or growth of the cells, to form at least one type of tissue thereon, thereby producing a cultured tissue product. According to certain embodiments, the cells are non-human animal cells, thereby the method results in producing cultured meat product.

Advantageously, the freeze-dried porous 3D scaffold of the present invention is characterized by having a macroporous structure having a high porosity, wherein the macropores can enable improved growth-medium passage therethrough (as part of the growth conditions) in order to support the growth and/or expansion of cells and/or tissues cultured thereon, as well as improve growth and spread of seeded cells thereon. In further embodiments, the scaffold is edible and the cells are non-human-animal cells.

Typical freeze-drying processes are known for enabling gentle low temperature dehydration of materials, unlike most conventional dehydration methods that evaporate water using heat, and therefore freeze drying can enable to maintain the quality and 3D structure of the dried materials. Thus, it is contemplated that the utilization of a freeze-drying process can enable to maintain the advantageous predetermined macro-porous structure of the 3D scaffolds.

In addition, it is contemplated that the utilization of the composition of step 100 as disclosed above, comprising a protein and/or a polysaccharide, each in a range of about 0.1-15% w/v of the composition of the present invention, enables to form the advantageous macro-porous structure of the scaffolds. It is possible that a composition comprising a higher concentration of proteins may result in a more viscous or dense hydrogel, resulting in the fabrication of a scaffold having a lower porosity or a different undesired porous structure.

As used herein, the term "macro-porous" refers to a 3D scaffold comprising a plurality of extruded members, wherein each extruded member comprises a plurality of pores having a size greater than 50 nanometers.

According to some embodiments, the freeze-dried porous 3D scaffolds of the present invention can be used for cell seeding thereon/therewithin, for various tissue engineering applications and optionally for cultured meat applications. According to some embodiments, the porous 3D scaffold can be utilized for cell seeding thereon, wherein the cells are seeded on sterilized freeze-dried scaffolds fabricated as presented hereinabove.

For example, Bovine satellite cells (BSCs) can be seeded on sterilized scaffolds, fabricated as previously mentioned. The cells can be left to proliferate and later differentiate into mature myotubes, using suitable growth media. In order to maintain shape fidelity of the 3D-printed seeded scaffolds for long cultivation periods, they could be mechanically constrained (for example, they could be placed on poly-di-methyl-siloxane (PDMS) surfaces and pinned in the corners thereof).

According to some embodiments, there is provided a freeze-dried 3D scaffold fabricated by the method of the present invention as disclosed herein above. According to further embodiments, the freeze-dried 3D scaffold comprises a plurality of layers, wherein each layer comprises a plurality of extruded members. According to still further embodiments, each member comprises at least one hydrogel, wherein the hydrogel comprises the at least one composition as disclosed herein above. According to yet still further embodiments, the composition comprises at least one protein at a concentration range of about 0.1-15% w/v of the composition, and at least one polysaccharide at a concentration range of about 0.1-5% w/v of the composition. According to still further embodiments, the composition is devoid of cells. According to certain exemplary embodiments, the freeze-dried 3D scaffold is edible.

The freeze-dried 3D edible scaffold as presented herein can be used in growing a 3D nutritious engineered edible tissue, intended for cultured meat applications.

According to some embodiments, there is provided a cultured meat product produced by the method of the present invention as disclosed herein above.

According to some embodiments, the 3D edible scaffolds manufactured by the present invention as disclosed herein above are configured to have meat-mimetic mechanical properties, such as in terms of external resemblance, integrity, deformability, elasticity, and fibrous texture.

Figure 1B:
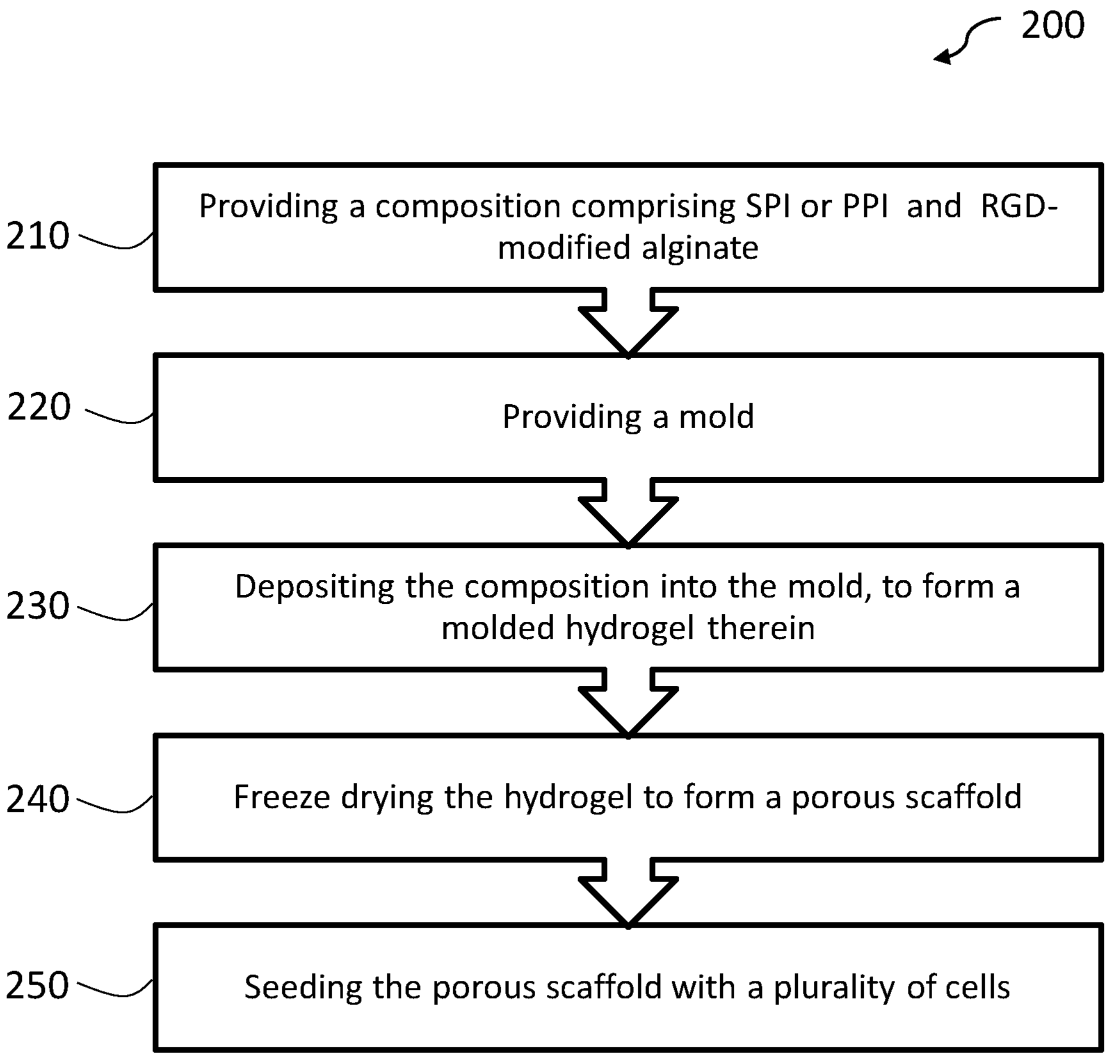
FIG. 1B show a flowchart for a method 200 for the fabrication of a freeze-dried porous scaffold based on SPI or PPI hydrogel solutions, according to some embodiments.

Reference is now made to FIG. 1B showing a flowchart for a method 200 for the fabrication of a freeze-dried porous scaffold based on SPI or PPI hydrogel solutions, according to some embodiments.

According to certain embodiments, there is provided a method 200 for producing a freeze-dried porous scaffold, wherein method 200 is a specific embodiment based on the embodiments of method 100 as disclosed herein above. In some embodiments, the method 200 comprises step 210 of providing a composition comprising a protein selected from SPI or PPI at a concentration selected from the range of about 1-3% w/v of the composition, and a polysaccharide comprising RGD-modified alginate at a concentration selected from the range of about 1-3% w/v of the composition. In some embodiments, method 200 further comprises step 220 of providing a mold. In some embodiments, method 200 further comprises step 230 of depositing the composition of step 210 into the mold of step 220, to form a molded hydrogel, and then depositing a crosslinking solution comprising $CaCl_2$ on the molded hydrogel, to induce gelation of the composition while it is in the mold. In some embodiments, method 200 further comprises step 240 of freeze-drying the 3D molded hydrogel, to form a freeze-dried porous scaffold. In some embodiments, method 200 further comprises step 250 of seeding the freeze-dried porous scaffold with a plurality of BSCs, and placing the scaffold under growth conditions enabling differentiation and/or growth of the cells thereon.

Figure 1C:
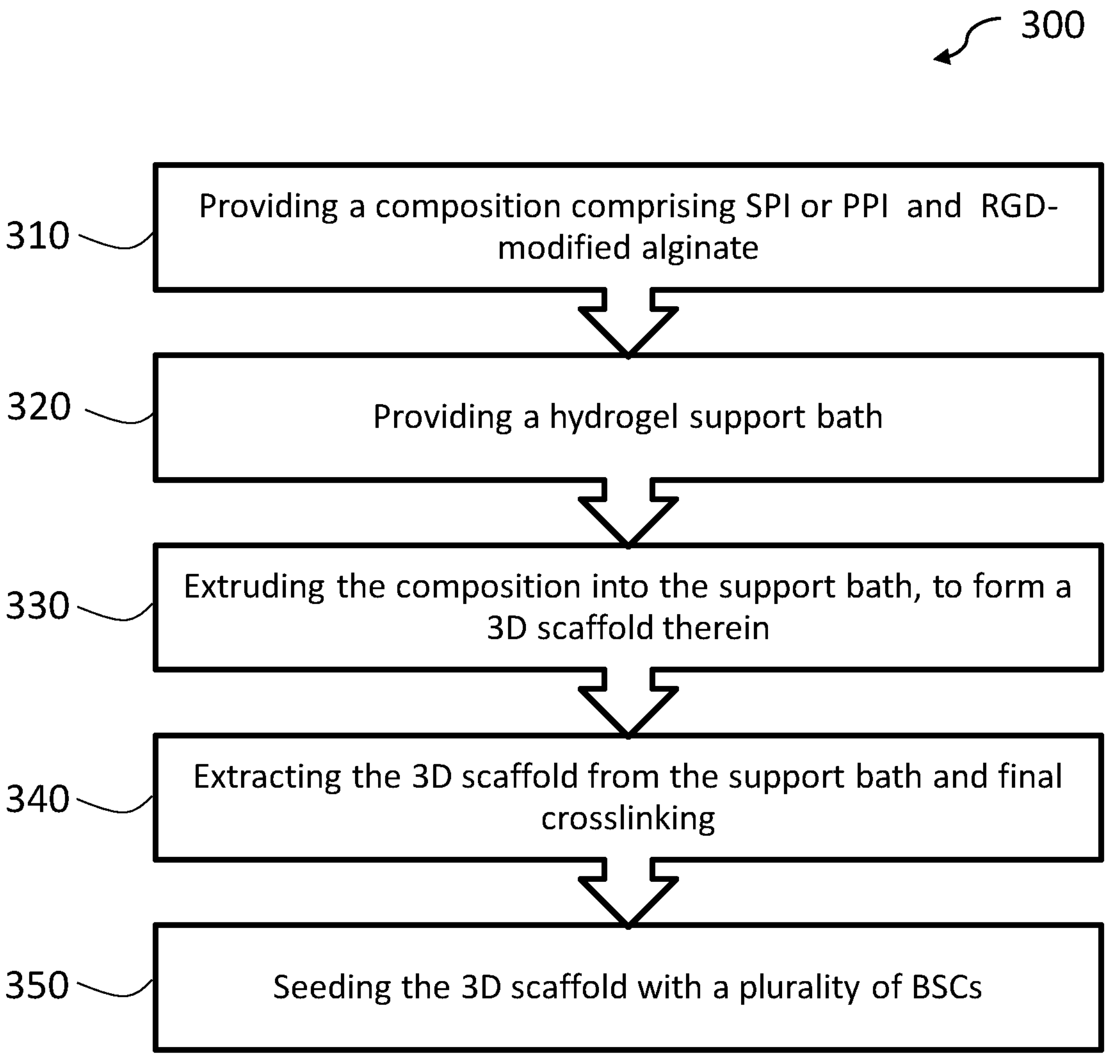
FIG. 1C show a flowchart for a method 300 for the fabrication of a 3D scaffold based on SPI or PPI hydrogel solutions, according to some embodiments.

Reference is now made to FIG. 1C showing a flowchart for a method 300 for the fabrication of a 3D scaffold based on SPI or PPI hydrogel solutions, according to some embodiments.

According to certain embodiments, there is provided a method 300 for producing a 3D scaffold, wherein method 300 is a specific embodiment based on the embodiments of method 100 as disclosed herein above. In some embodiments, the method 300 comprises step 310 of providing a composition comprising a protein selected from SPI or PPI at a concentration selected from the range of about 1-3% w/v of the composition, and a polysaccharide comprising RGD-modified alginate at a concentration selected from the range of about 1-3% w/v of the composition. In some embodiments, method 300 further comprises step 320 of providing an agar hydrogel support bath comprising a low concentration of $CaCl_2$ disposed therein. In some embodiments, method 300 further comprises step 330 of extruding the composition of step 310 into the support bath of step 320 via 3D printing, to form a 3D scaffold therein, which may have various 3D structures and inner patterns. In some embodiments, method 300 further comprises step 340 of extracting the 3D scaffold from the agar support bath while crosslinking the 3D scaffold. In further embodiments, step 340 is performed by immersing the support bath with the 3D scaffold within a $CaCl_2$ solution for final crosslinking of the scaffold, while performing gentle pipetting for the agar hydrogel removal from the 3D scaffold. In some embodiments, method 300 further comprises step 350 of seeding the 3D scaffold with a plurality of BSCs, and placing the scaffold under growth conditions enabling differentiation and/or growth of the cells thereon.

Figure 1D:
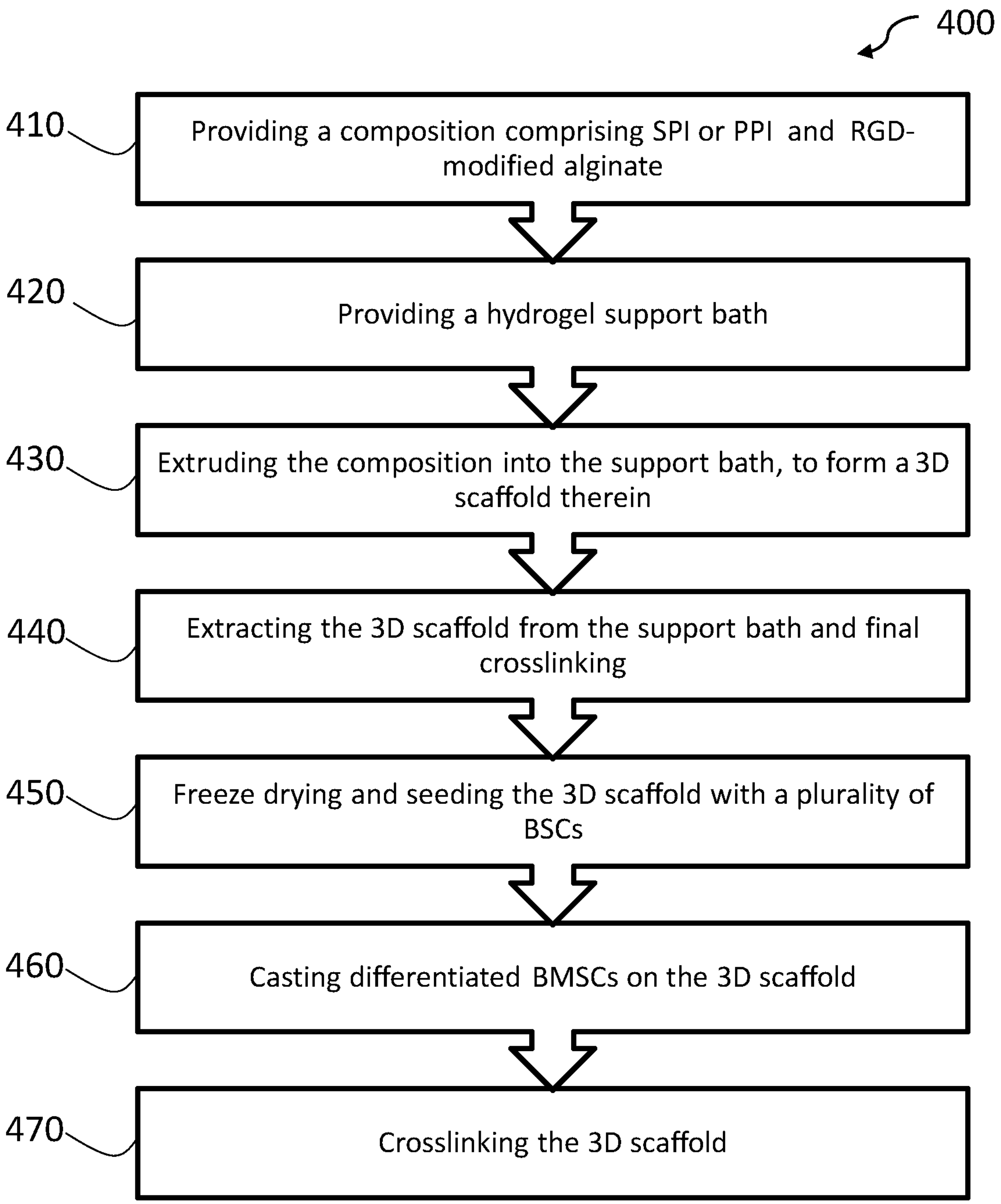
FIG. 1D show a flowchart for a method 400 for the fabrication of a 3D scaffold comprising two cells-types, according to some embodiments.

Reference is now made to FIG. 1D showing a flowchart for a method 400 for the fabrication of a 3D scaffold comprising two cells-types, according to some embodiments.

According to certain embodiments, there is provided a method 400 for producing a 3D scaffold, wherein method 400 is a specific embodiment based on the embodiments of method 100 as disclosed herein above. In some embodiments, the method 400 comprises step 410 of providing a composition comprising a protein selected from SPI or PPI at a concentration of about 1% w/v of the composition, and a polysaccharide comprising RGD-modified alginate at a concentration of about 1% w/v of the composition. In some embodiments, method 400 further comprises step 420 of providing an agar hydrogel support bath comprising a low concentration of $CaCl_2$ disposed therein. In some embodiments, method 400 further comprises step 430 of extruding the composition of step 410 into the support bath of step 420 via 3D printing, to form a 3D scaffold therein, which may have various 3D structures and inner patterns. In some embodiments, method 400 further comprises step 440 of extracting the 3D scaffold from the agar support bath while crosslinking the 3D scaffold. In further embodiments, step 440 is performed by immersing the support bath with the 3D scaffold within a $CaCl_2$ solution for final crosslinking of the scaffold, while performing gentle pipetting for the agar hydrogel removal from the 3D scaffold. In some embodiments, method 400 further comprises step 450 of freeze-drying the 3D scaffold, and then seeding the rehydrated freeze-dried 3D scaffold with a plurality of cells, for example BSCs, and placing the scaffold under growth conditions enabling differentiation and/or growth of the cells thereon. In some embodiments, method 400 further comprises step 460 of depositing or casting differentiated cells, for example BMSCs (i.e., Adipocytes) suspended in an alginate mixture on the 3D scaffold from step 450. In some embodiments, method 400 further comprises step 470 of pouring or casting a $CaCl_2$ solution on top of the differentiated cells, for example BMSCs suspended in the alginate mixture from step 460 in order to perform a final crosslinking of the scaffold, to create a hybrid 3D scaffold comprising two cell-types.

Figure 1E:
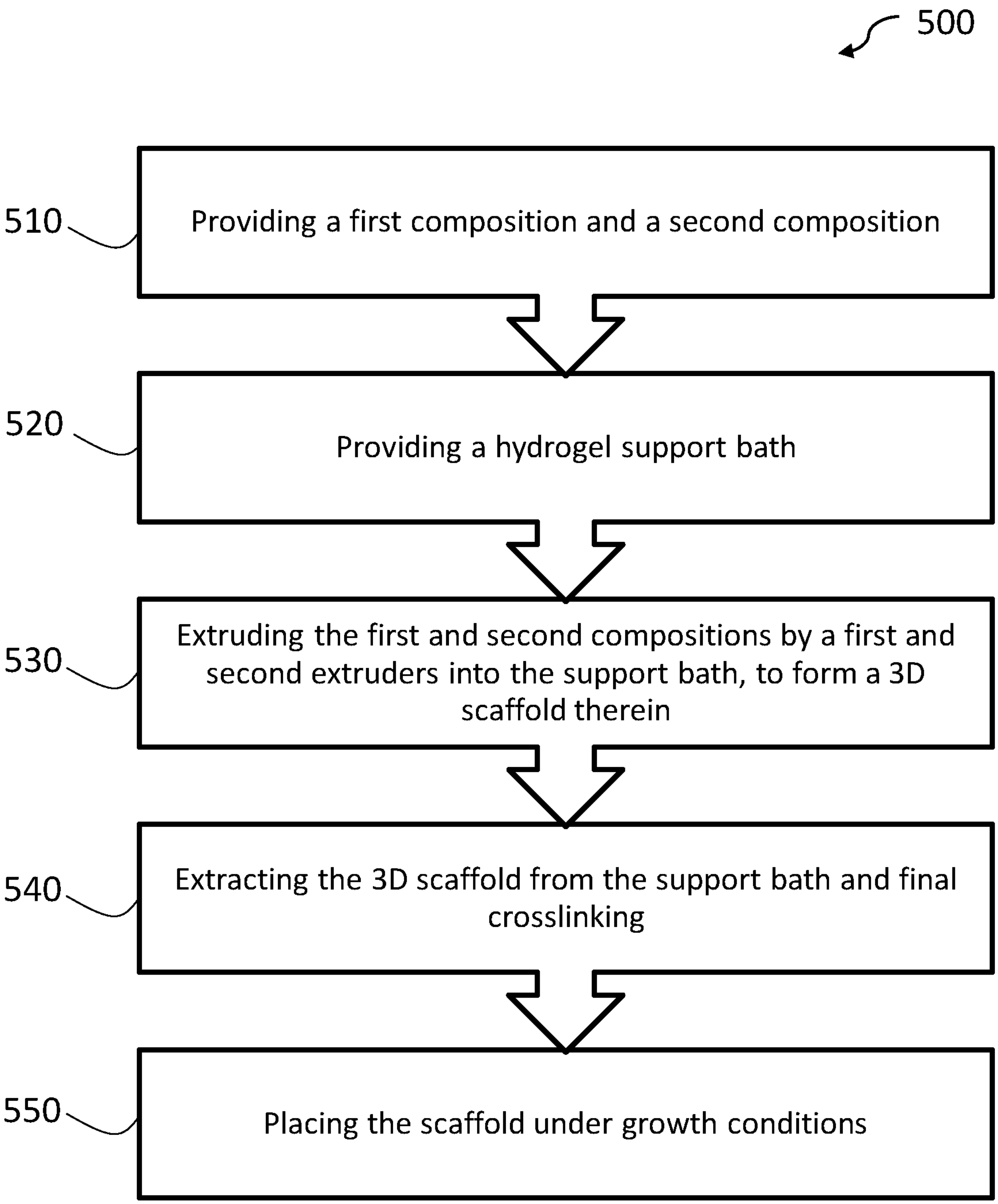
FIG. 1E show a flowchart for a method 500 for the fabrication of a 3D scaffold, according to some embodiments.
Figure 1F:
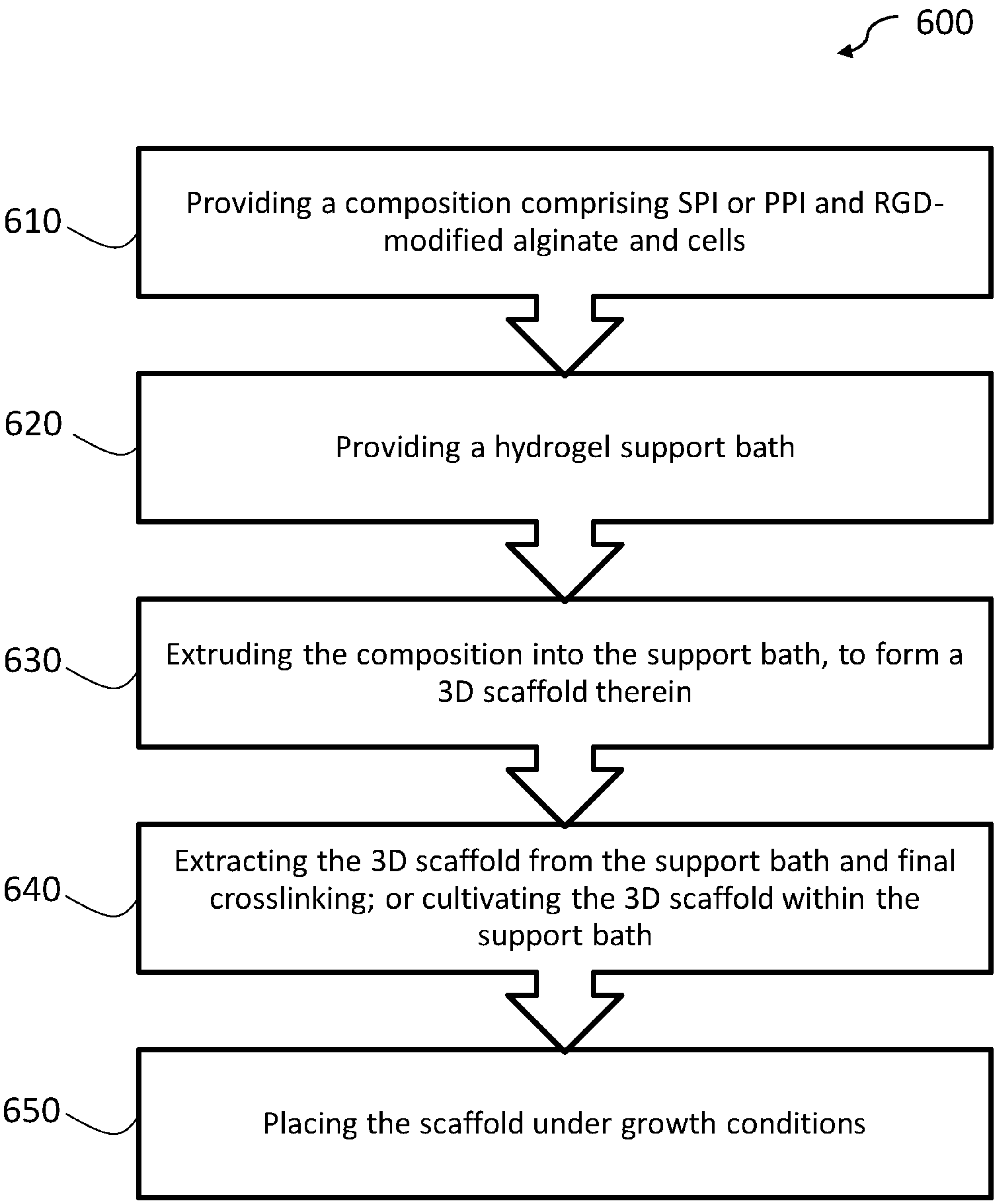
FIG. 1F show a flowchart for a method 600 for the fabrication of a 3D scaffold, according to some embodiments.

Reference is now made to FIG. 1E showing a flowchart for a method 500 for the fabrication of a 3D scaffold, according to some embodiments.

According to certain embodiments, there is provided a method 500 for producing a 3D scaffold, wherein method 500 is a specific embodiment based on the embodiments of method 100 as disclosed herein above. In some embodiments, the method 500 comprises step 510 of providing a first composition comprising a protein comprising PPI at a concentration of about 1% w/v of the composition, a polysaccharide comprising RGD-modified alginate at a concentration of about 1% w/v of the composition, first type of non-human-animal cells, for example Bovine Satellite cells (BSCs), and optionally gelatin-microparticles acting as porogens. In some embodiments, the first composition of step 510 comprises a protein comprising collagen at a concentration of about 1% w/v of the composition, cells (e.g., BSCs), and optionally gelatin-microparticles acting as porogens. In some embodiments, step 510 further comprises providing a second composition comprising a protein comprising PPI at a concentration of about 2% w/v of the composition, a polysaccharide comprising alginate at a concentration of about 1% w/v of the composition, and a second type pf cells being mature cells, for example BMSCs—Bovine mesenchymal stem cells (e.g., Adipocytes). In some embodiments, method 500 further comprises step 520 of providing an agar hydrogel support bath comprising a low concentration of $CaCl_2$ disposed therein. In some embodiments, method 500 further comprises step 530 of extruding the first and second compositions simultaneously by a first and second extruders, respectively, into the support bath of step 520 via 3D printing, to form a 3D scaffold therein, which may have various 3D structures and inner patterns. In some embodiments, method 500 further comprises step 540 of extracting the 3D scaffold from the agar support bath, optionally while crosslinking the 3D scaffold, similarly to step 340 as disclosed above. In some embodiments, method 500 further comprises step 550 of placing the scaffold under growth conditions enabling differentiation and/or growth of the cells thereon.

According to certain embodiments, there is provided a method 600 for producing a 3D scaffold, wherein method 600 is a specific embodiment based on the embodiments of method 100 as disclosed herein above. In some embodiments, the method 600 comprises step 610 of providing a composition comprising: a protein selected from SPI or PPI at a concentration of about 1% w/v of the composition; a polysaccharide comprising RGD-modified alginate at a concentration of about 1% w/v of the composition; cells, for example Bovine Satellite cells (BSCs) at a final concentration of $50\times10^6$ cells/ml, and optionally gelatin-microparticles acting as porogens. In some embodiments, method 600 further comprises step 620 of providing an agar hydrogel support bath comprising a low concentration of $CaCl_2$ disposed therein. In some embodiments, method 600 further comprises step 630 of extruding the composition into the support bath of step 620 via 3D printing, to form a 3D scaffold therein, which may have various 3D structures and inner patterns. In some embodiments, method 600 further comprises step 640 of extracting the 3D scaffold from the agar support bath while crosslinking the 3D scaffold. In alternative embodiments, step 640 comprises crosslinking the 3D scaffold and cultivating it within the agar support bath. In some embodiments, method 600 further comprises step 650 of placing the scaffold under growth conditions (such as supplementing the scaffold with a suitable medium), within or without the agar support bath, thus enabling differentiation and/or growth of the cells thereon and/or therewithin.

The term "about", as used herein, when referring to a measurable value such as an amount, a temporal duration, and the like, is meant to encompass variations of +/−10%, more preferably +/−5%, even more preferably +/−1%, and still more preferably +/−0.1% from the specified value, as such variations are appropriate to the disclosed devices, systems and/or methods.

Certain embodiments of the present invention may include some, all, or none of the above advantages. Further advantages may be readily apparent to those skilled in the art from the figures, descriptions, and claims included herein. Aspects and embodiments of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The following embodiments and aspects thereof are described and illustrated in conjunction with systems, tools and methods which are meant to be exemplary and illustrative, but not limiting in scope. In various embodiments, one or more of the above-described problems have been reduced or eliminated, while other embodiments are directed to other advantages or improvements.

EXAMPLES

Example 1—F.D Mold-Based Scaffold Fabrication

In order to prepare freeze-dried (termed herein 'F.D') mold-based scaffolds, SPI (Soy protein isolate, MP Biomedicals), which contains 90% protein (dry basis), and PPI (Pea protein isolate, Roquette), which contains 83% protein (dry basis), were each dissolved in ultrapure water into 2% w/v protein concentration. The two solutions were then autoclaved at 121° C. for 20 minutes. Meanwhile, Alginate:RGD (RGD modified alginate, Novamatrix) was also dissolved in PBS, 2% w/v. Each of the protein-enriched solutions were mixed in a 1:1 ratio with the Alginate:RGD, creating final mixtures of: Alginate:RGD-SPI (1%-1% w/v) and Alginate:RGD-PPI (1%-1% w/v).

For mold-based scaffold assessments, two additional solutions were prepared: 1% Alginate:RGD, and 1% of non-modified alginate (Alginic acid sodium salt from brown algae, Sigma).

All four solutions (see Table 1) were then casted into Teflon molds (8 mm inner diameter, 1.5 mm height) and crosslinked with 100 mM $CaCl_2$ (Calcium Chloride anhydrous, spectrum) for 20 minutes, in order to create 3D molded hydrogel plugs.

Figure 2A:
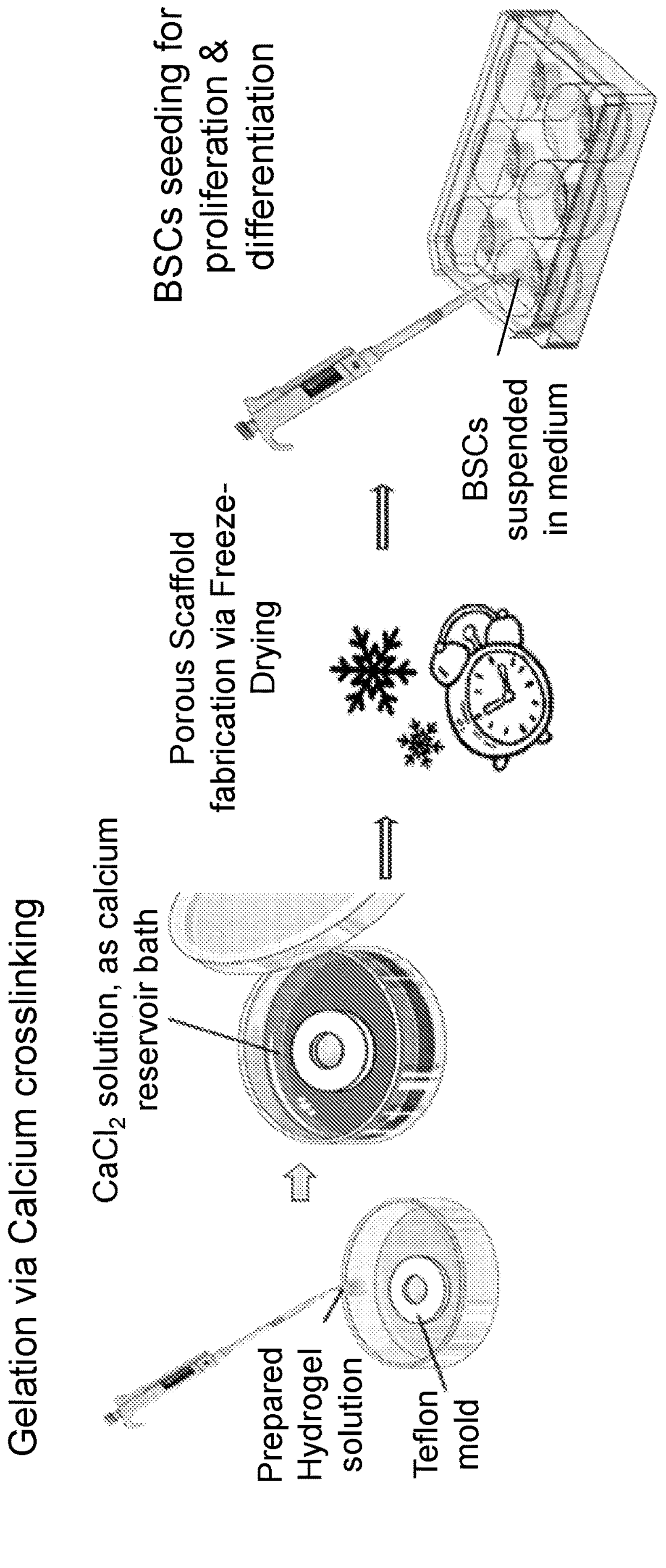
FIG. 2A schematically illustrates a preparation process for freeze-dried (F.D) mold-based scaffolds based on various hydrogel solutions, according to some embodiments of the present invention.

FIG. 2A schematically illustrates the preparation process for the F.D mold-based scaffolds, which was similar to method 200 as disclosed herein above, wherein the compositions were based on the hydrogel solutions as presented at Table 1.

During polymerization, alginate was able to crosslink via an 'egg-box' model, while the denatured protein aggregates were able to undergo the second and final step of 'cold-set' gelation. Later, said 3D molded hydrogels were frozen at −20° C. for about 12-18 hrs., and subsequently lyophilized (freeze-drying) for additional 24 hrs., thus resulting in the formation of F.D porous sponge-like scaffolds.

TABLE 1

| Protein-enriched hydrogel solutions | |
|---|---|
| Hydrogel composition type | Component concentration [W/V] |
| Alginate | 1% |
| Alginate:RGD | 1% |
| Alginate:RGD - SPI | 1%-1% |
| Alginate:RGD - PPI | 1%-1% |

Example 2—Alar Support Bath Preparation

It is contemplated that both of the solutions of Alginate: RGD-SPI (1%-1% w/v) and Alginate:RGD-PPI (1%-1% w/v) from example 1 can polymerize in the presence of calcium ions, and therefore agar support baths containing $CaCl_2$ for hydrogel formation and support during 3D-printing were prepared. Utilizing 500 ml Mason jars, 1.5% agar (agar bacteriological, Acumedia) and 10 mM $CaCl_2$ were dissolved in distilled water (250 ml), by autoclaving at 121° C., 20 min. Gelation of the Agar solutions into pucks was later induced by cooling at room temperature. The jars were then transferred to 4° C., overnight. 10 mM calcium solution was later poured on-top of the gelled agar puck, and a spatula was used to detach them from the jars. Each jar was then filled to the brim with the $CaCl_2$ solution (10 mM) and blended in pulse mode, 45 s, using a household blender (Classic series, Oster). The contents were then aliquoted in 50 mL tubes, and centrifuged (after resuspension) at 4° C. for 5 min. After discarding of the supernatant, the final micro-gel support bath was established and kept in suspension with additional Calcium solution, 4° C. Prior to 3D-printing, the materials were centrifuged again for supernatant removal and support bath transfer into 35 mm petri dishes, placed onto the printer's stage section.

Example 3—3D-Printed Scaffold Fabrication 3D printing of various structures was done using two 3D printer types: a 3D-Bioplotter Manufacturer Series (Envisiontec), and BIO X™ (Cellink), wherein the printing process was based on the hydrogel compositions from Table 1. A 3D 10×10 mm model was created using SolidWorks, then exported as an STL file for slicing, later translated into a G-code suitable for 3D printing. For the 3D-Bioplotter printer, slicing was done using the Perfactory software, while files were sliced by Slic3r for the BIO X™. Printing characteristics of printed scaffolds, such as inner scaffold patterns, infill percentage, pattern density, pneumatic pressure, needle speed, and the like, were all determined using the printers' control software.

The infill percentage represents an amount of printed material within a frame structure of each scaffold. This parameter can vary from 0% up to 100%. An infill percentage of 0% represents a printed scaffold containing only an external structure (e.g., frame), with no inner pattern material inside. If the percentage value is higher than 0%, the 3D printer will print material inside the frame (i.e., the edible (extruded) members), using a specific laying geometry pattern that can be pre-determined using a computer model.

Figure 2B:
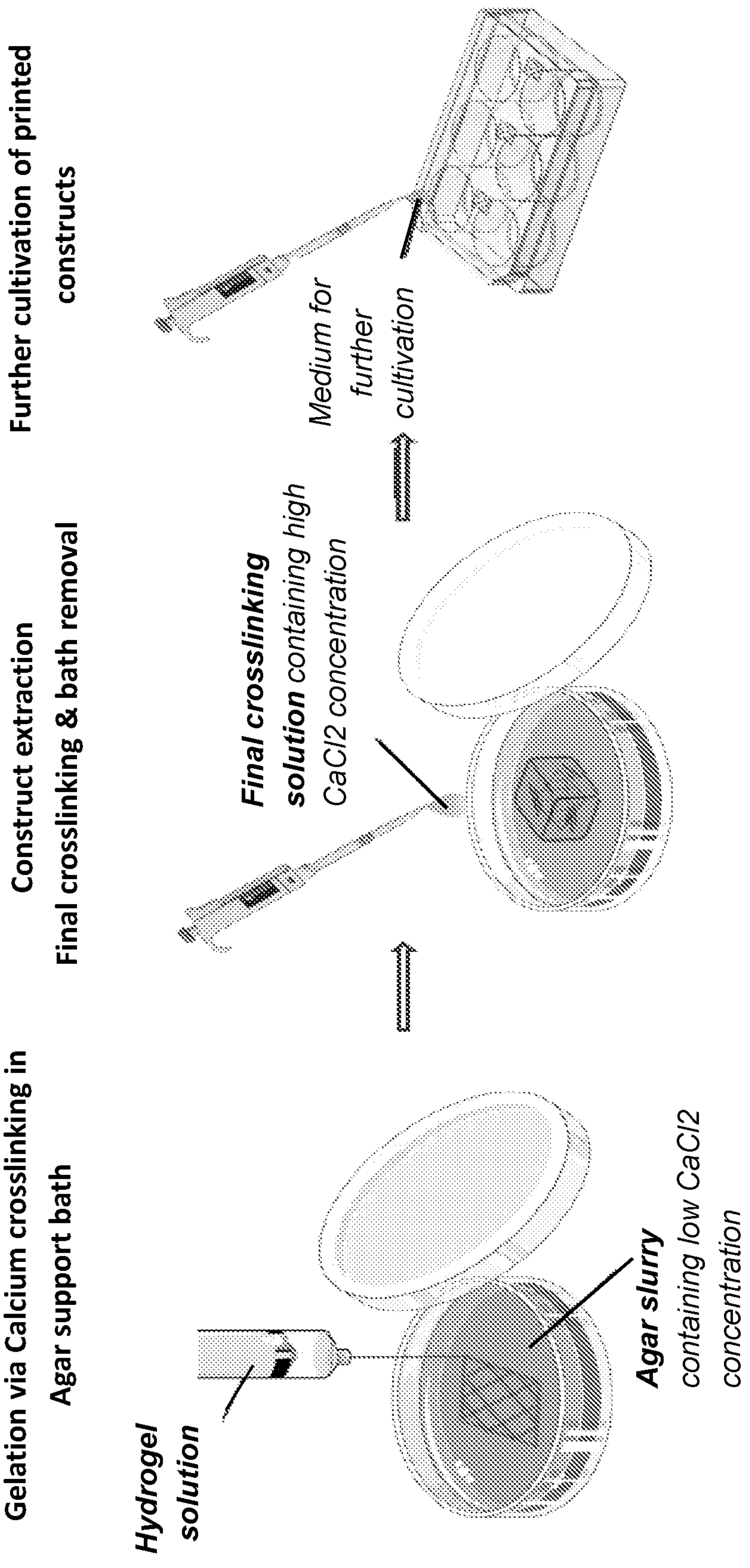
FIG. 2B schematically illustrates a preparation process for 3D printing of protein-enriched scaffolds, by means of Agar slurry support bath usage and removal, according to some embodiments the present invention.

FIG. 2B schematically illustrates the printing process of various 3D scaffolds described herein, which was similar to method 300 as disclosed herein above. All scaffolds were fabricated by extruding the hydrogel solutions from example 1 into the agar support baths from example 2, thereby forming a plurality of edible members therein arranged in various patterns to from the desired structure of the final scaffold. The hydrogel solutions were deposited and embedded within the support bath in order to maintain the intended structure during the printing process while significantly improving printing accuracy. The plurality of edible members was arranged in a grid pattern, a honeycomb pattern, and a parallel pattern.

Figure 3A:
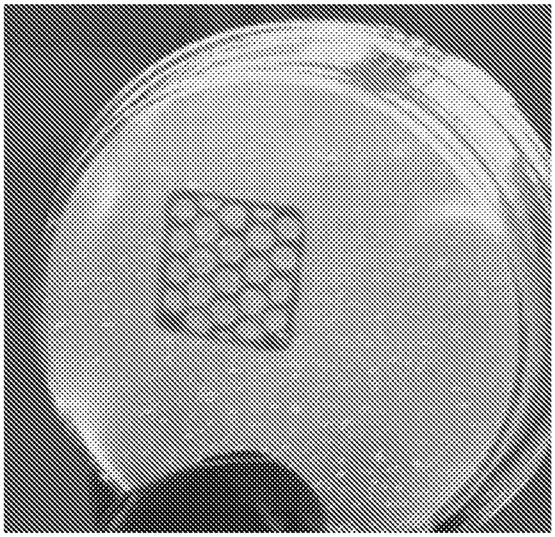
FIGS. 3A-3G show 3D printed protein-enriched scaffolds, based on the process of FIG. 2; 5-layered honeycomb structure, 13% infill (FIG. 3A); 5-layered grid structure, 12% infill (FIG. 3B); 15-layered grid structure, 15% infill (FIG. 3C); 3-layered grid structure (FIG. 3D); 5× magnification of FIG. 3D following extraction using confocal Bright-Field imaging (scale bar=2 mm) (FIG. 3E); 10× magnification of FIG. 3E (scale bar=500 μm) (FIG. 3F); and 2-layered parallel strands, following extraction and confocal Bright-Field imaging (5× magnification, scale bar=2 mm) (FIG. 3G).
Figure 3B:
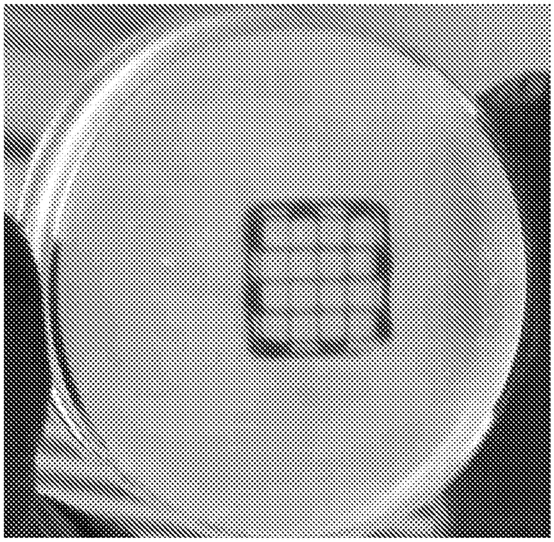
Figure 3C:
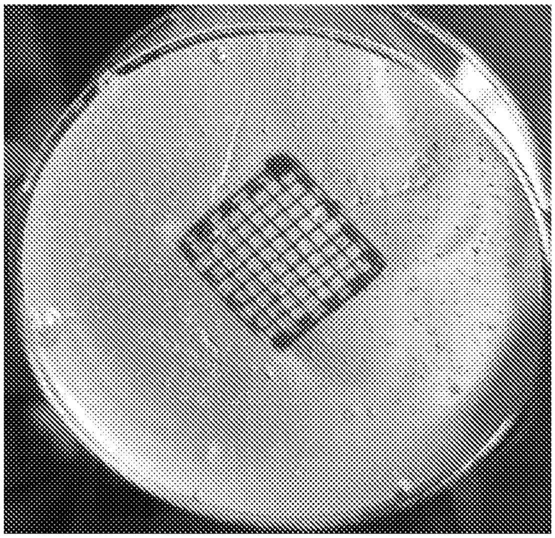

Three types of scaffolds having various multi-layer patterns containing Alginate:RGD-SPI hydrogels were fabricated using the BIO X, with 27 G needle, 100 kPa pressure and 12 mm/sec needle speed: (1) honeycomb 5-layer structure (13% infill), (2) grid 5-layer (12% infill), and (3) grid 15-layer (15% infill) (FIGS. 3A-3C, respectively).

Figure 3D:
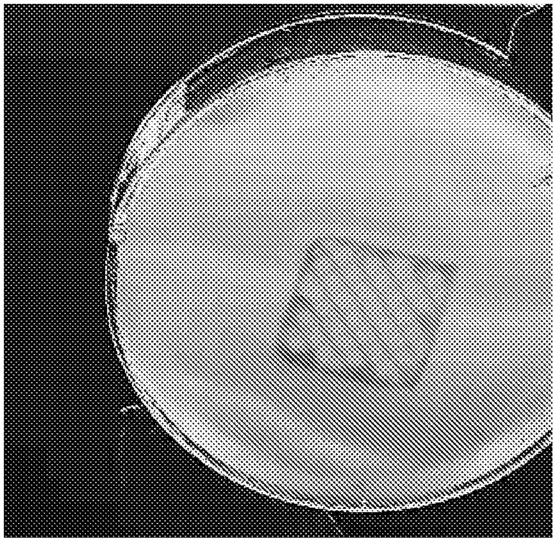
Figure 3E:
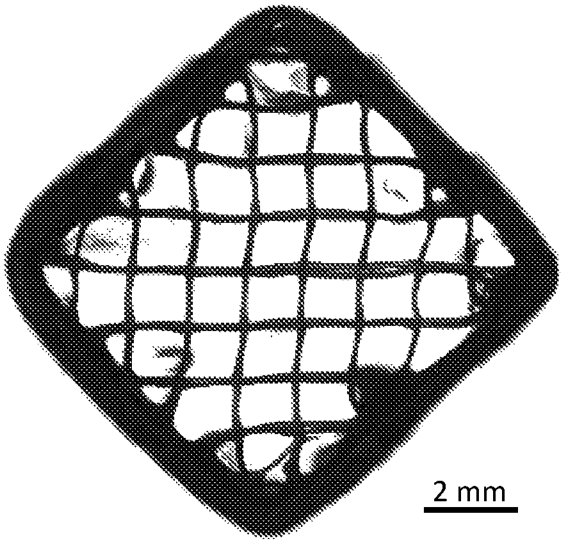
Figure 3F:
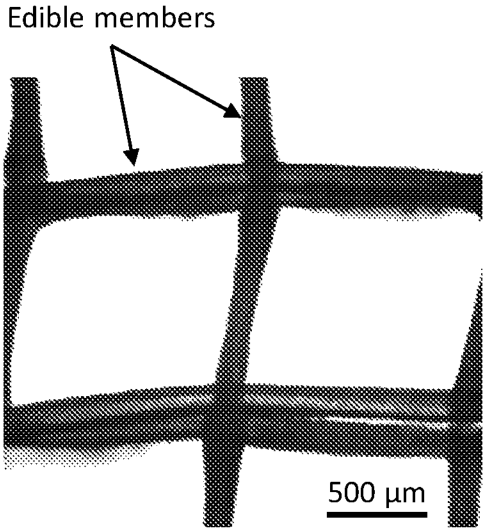
Figure 3G:
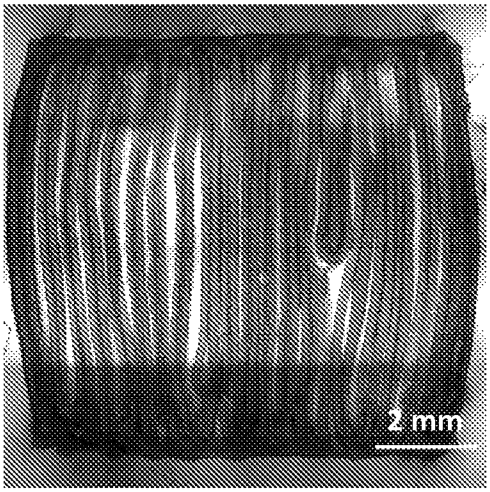

For scaffolds fabricated using the 3D-Bioplotter, a 27 G (0.22 mm) needle was used, with 0.6 bar pressure and 30 mm/sec needle speed, resulting in two multi-layered scaffold patterns: 3-layered grid containing the Alginate:RGD-SPI hydrogel (1.5 mm distance between adjacent strands, 90° rotation between layers) (FIGS. 3D-3F); and 2-layered parallel strands containing the Alginate:RGD-PPI hydrogel (0.5 mm distance between adjacent strands, 0.25 mm shift between layers) (FIG. 3G).

Final crosslinking and extraction from the agar support bath of all printed scaffolds was done by immersion of the bath within a 100 mM $CaCl_2$) solution for 20 min, while performing gentle pipetting for agar slurry removal.

Example 4—Mechanical Characterization Protocols

Swelling Ratio

Swelling ratio of F.D mold-based scaffolds from example 1 was evaluated by measuring their weight change due to liquid uptake. Two weight measurements were performed: the first measurement was performed in the dry state (WD) of the scaffolds, and a second measurement was performed after 24 hrs. of immersion within PBS (—Ca, —Mg) under 37° C. (WH) of the scaffolds. For the second measurement, the swollen scaffold sponges were removed from the solution, and excess liquid was removed using filter paper. All measurements were done using an analytical balance (AB104, Mettler Toledo). Eventually, after obtaining WD and WH of all samples, the swelling ratio could be determined by equation 1:

$$\text{Weight fold change} = \left[\frac{WH - WD}{WD}\right] \quad (1)$$

Scaffold Elasticity

Elasticity of F.D mold-based scaffolds from example 1 was assessed by measuring their tensile Young's modulus. F.D mold-based scaffolds from example 1 were evaluated after 1 hr. of rehydration in PBS (—Ca,—Mg) solution, at 37° C. The measurements were performed using a biodynamic test instrument (Electroforce; Bose). All samples were stretched uniaxially until failure was reached. From the obtained data, a stress-strain curve was generated for each sample: Stress was calculated as the measured force divided by the surface area (scaffolds' cross section area), while Strain was calculated as the length displacement divided by the scaffold's initial length. The Elastic modulus was then defined as the slope of the linear region in the stress-strain curve.

In-Vitro Degradation

In-vitro degradation of the F.D mold-based scaffolds from example 1 was calculated as well, at three predetermined time points: 1, 7, and 14 days of incubation. The scaffolds were kept in PBS (—Ca,—Mg) solution at 37° C. At each time point, the suitable scaffolds were taken out, lyophilized (i.e., freeze-dried) for 3 hours to remove all liquid content, and measured for their dry weight using analytical balance (AB104, Mettler Toledo). The weight loss was determined as presented in equation 2:

$$\text{Scaffold weight loss } [\%] = \left[\frac{\text{initial dry weight} - \text{final dry weight}}{\text{initial dry weight}}\right] \times 100 \quad (2)$$

Micro-CT Scanning, Reconstruction, and Porosity Analysis

Mold-based FD scaffolds from example 1 were scanned using a high-resolution microCT scanner (Skyscan 1276, Bruker, Kontich, Belgium). The following scanning parameters were used: source voltage of 55 kV, source current of 72 μA, applied filter of aluminum 0.25 mm. Scanning was performed using a 0.3-degree rotation step with frame averaging (2) and an exposure time of 1420 ms (milliseconds), yielding a total of 1201 projections in 360 degrees around the scanned object. Images were acquired with a scaled pixel size of 5 μm. Back projections were reconstructed using NRecon (Skyscan, version 1.7.3.0), Dataviewer (Skyscan, version 1.5.4.6) was used to verify proper alignment of scanned objects, CTAnn Software (Skyscan, version 1.17.7.2) was used for segmentation, VOI for construction and analysis, and CTVox (Skyscan, version 3.3.0) for 3D visualization. VOIs consisting of 200 cross-sections were analyzed for their total porosity.

Example 5—Mechanical Characterization Results

To evaluate physio-mechanical attributes essential for muscle-cell cultivation on the fabricated freeze-dried F.D mold-based scaffolds of example 1 composed of Alginate: RGD with/out added proteins, the total porosity, the swelling ratio, initial tensile Young's modulus, and degradation rate of the scaffolds were assessed.

Figure 4A:
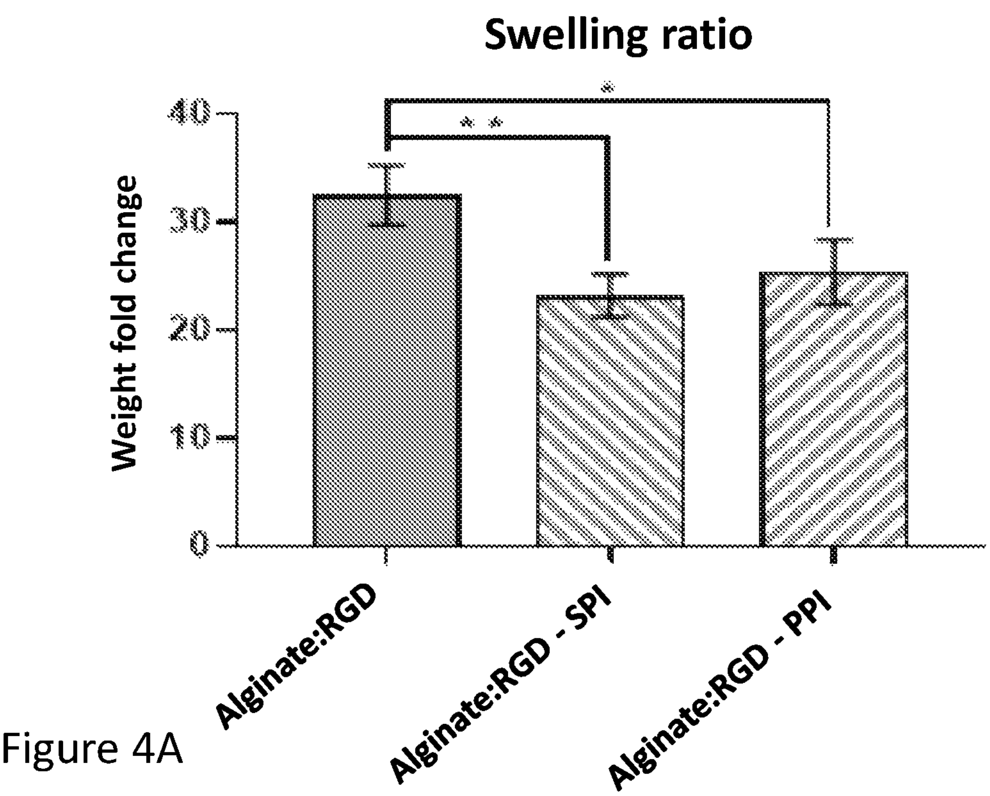
FIGS. 4A-E show results for physical and mechanical properties of freeze-dried acellular scaffolds: The scaffolds were assessed by swelling ratio after 24 hrs. of rehydration (FIG. 4A); tensile Young's modulus (FIG. 4B); in-vitro degradation degree during 2 weeks of incubation (FIG. 4C); total porosity of the scaffolds, as determined by 3D analysis of the 3D-reconstructed scans (FIG. 4D); and microCT scans of the different scaffold types: i) Cross-sectional view, and ii) 3D-reconstructions (FIG. 4E). Statistical analysis was done using One-Way ANOVA for both FIG. 4A and FIG. 4B, N=3-4 and N=3-5 respectively. Two-Way ANOVA was performed for FIG. 4C, N=3. *, , * and **** signify a p-value below 0.05, 0.01, 0.001 and 0.0001, respectively.

Swelling ratio of the different scaffolds types was measured as an indication for material transfer capabilities of the hydrogel-based scaffolds with their liquid surroundings (FIG. 4A). After 24 hrs within PBS solution at 37° C., all three scaffold types had high swelling degrees or liquid uptakes, with the highest value corresponding to Alginate: RGD alone (32.5±2.784 weight fold change). All types included hydrophilic Alginate content, yet some also included protein-aggregates (SPI or PPI) with more hydrophobic properties. While the values obtained for protein enriched types were significantly lower (23.20±1.975 and 25.38±2.978), their swelling capabilities were still high.

Figure 4B:
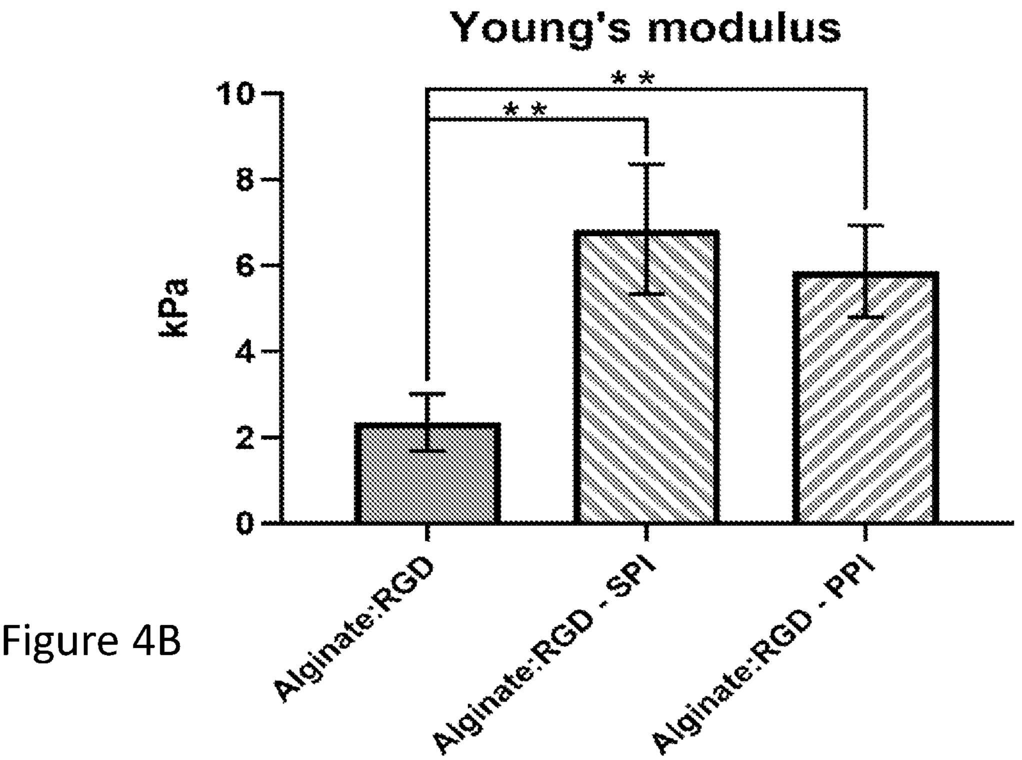

As another main mechanical property known to affect tissue growth and overall sensory attributes, the Young's modulus of the scaffolds was assessed as well, using the tensile method (FIG. 4B). The measured elasticity of all swelled scaffolds was shown to be in the same order of magnitude, with protein-enriched ones reaching significantly higher values than of the Alginate:RGD alone (6.846±1.505 and 5.865±1.070 compared to 2.351±0.6645 kPa; p-values <0.01). Thus, the incorporation of either SPI or PPI enhanced the scaffolds' stiffness.

Figure 4C:
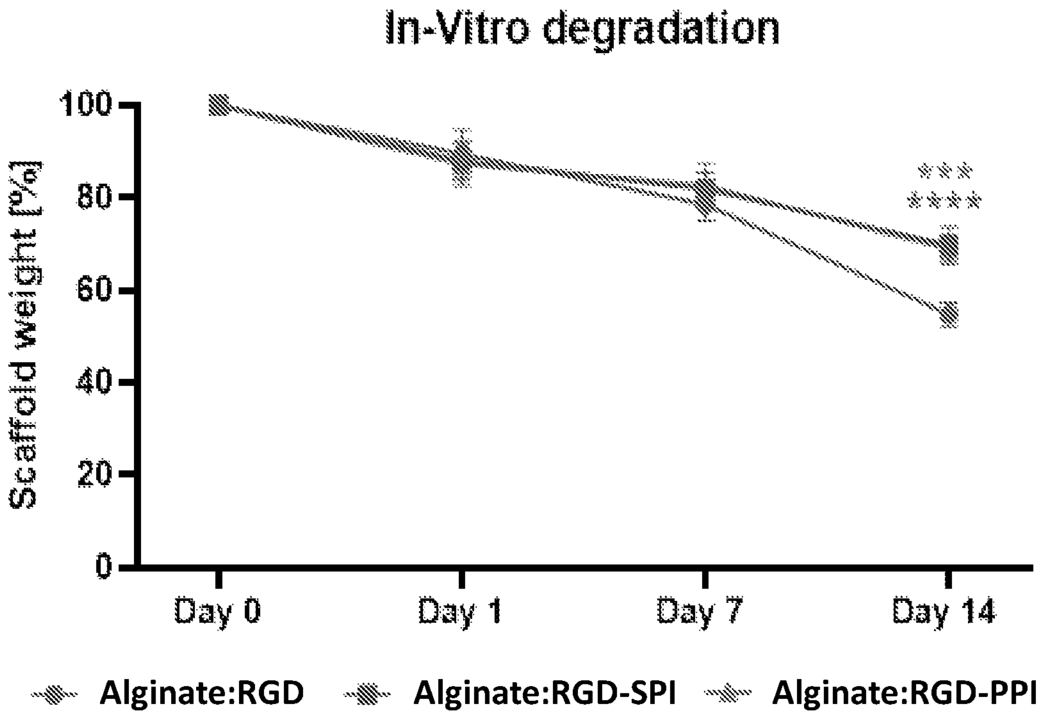

To determine long-term culturing possibilities using the suggested scaffolds, their resistance to degradation overtime was measured. To evaluate their degradation degree, their weight was measured at three time points during two weeks of acellular incubation (FIG. 4C). No significant degradation differences were observed during the first 7 days (p-values >0.05). However, significantly higher degradation of the Alginate:RGD alone was observed after 14 days, appearing less resilient compared to the protein containing scaffolds (p-value <0.0001 for Alginate:RGD-SPI, p-value=0.0001 for Alginate:RGD-PPI).

Figure 4D:
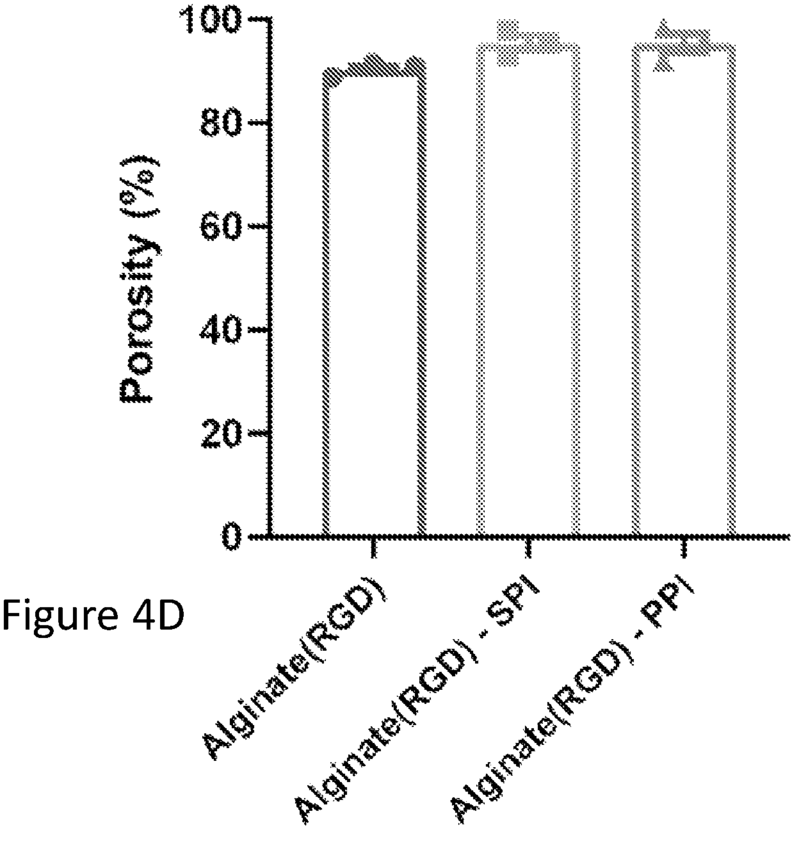
Figure 4E:
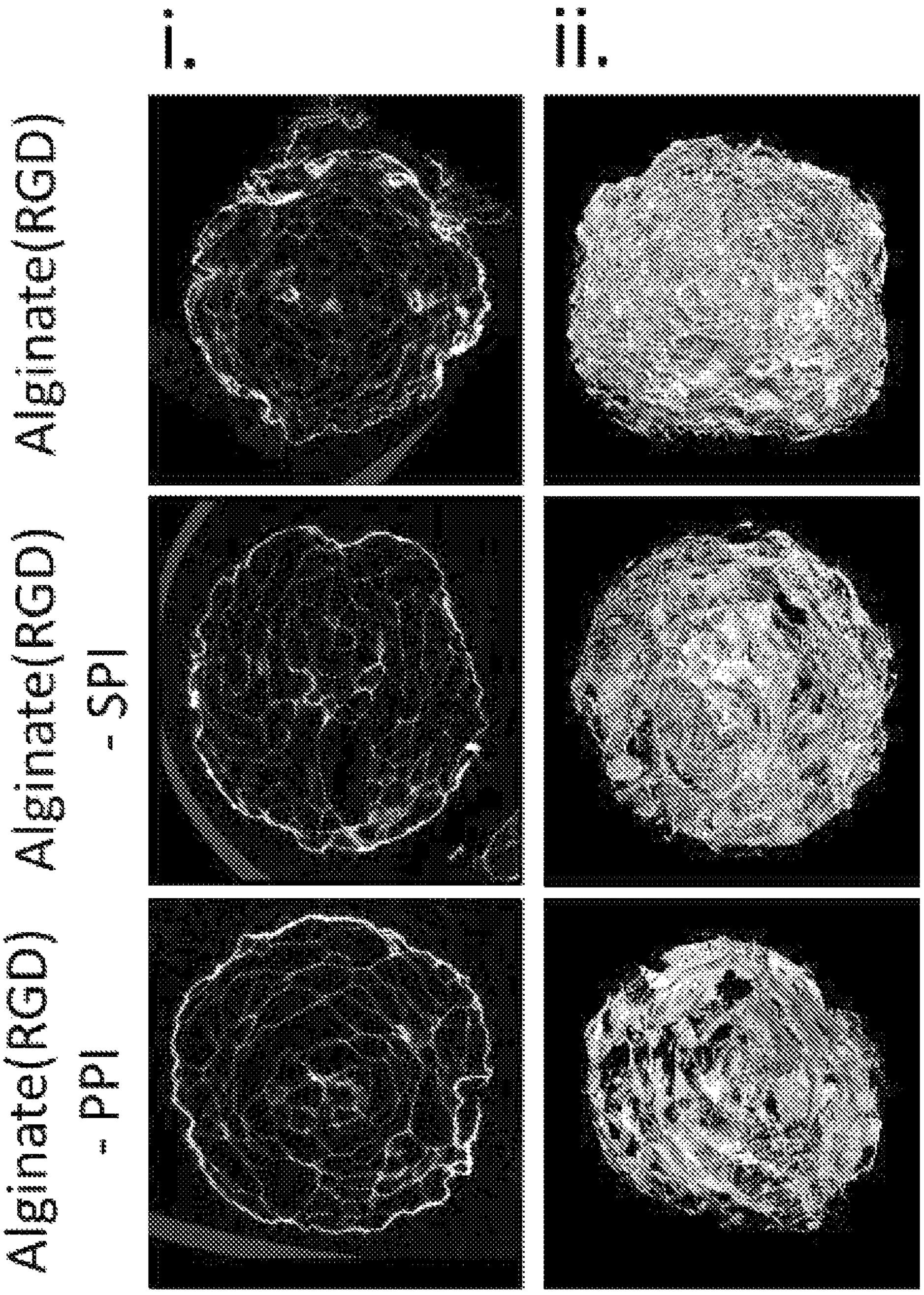

All types of Alginate:RGD, Alginate:RGD-SPI and Alginate:RGD-PPI scaffolds had similarly high total porosities (p-value >0.05), of 90.33±1.35%, 95.35±2.47% and 95.35±3.18%, respectively (see FIGS. 4D-4E).

Example 6—Bovine Satellite Cells (BSCs) Isolation Protocol

Bovine satellite cells (BSCs) isolation was previously described at Ben-Arye et al. (Ben-Arye, T. et al. Textured soy protein scaffolds enable the generation of three-dimensional bovine skeletal muscle tissue for cell-based meat. Nat. Food 1, 210-220, 2020).

Example 7—Cell Culture Protocols

Seeding

For all 3D experiments using either F.D mold-based scaffolds from example 1 or 3D printed scaffolds from example 3, BSCs passage 1 (P.1) were initially sub-cultured in 2-dimensional (2D) 0.1% w/v gelatin-coated flasks, for increase in cell numbers needed for seeding (number of cell passage is define as P.1, P.2, etc.).

Upon reaching adequate cell numbers, BSCs (P.2) were seeded on sterile freeze-dried (F.D) mold-based scaffolds.

Additional BSCs (P.2) cell-seeding was performed on the 3D printed scaffolds (see FIG. 2B) using the multi-layered grid/parallel patterned scaffolds fabricated by the 3D-Bioplotter (the scaffolds of FIGS. 3D-3G), wherein the scaffolds were incubated in PBS solution for 1 hr, 37° C., prior to cell-seeding.

All seeded scaffolds were left to incubate at 37° C. for 1 hr, before being supplemented with proliferation medium. For further BSCs proliferation (termed herein '3D proliferation phase'), seeded scaffolds were supplemented with a proliferation medium, as was previously described at Ben-Arye et al. (2020, ibid). For BSCs myogenesis experiments (termed herein 'differentiation phase'), a differentiation medium was used, identical to the one detailed at Ben Arye et al. (2020, ibid). All scaffolds were kept in a 5% $CO_2$ humidified incubator at 37° C., with full replacement of the medium every other day.

Efficiency

Cell seeding efficiency on the F.D mold-based scaffolds of example 1 was calculated 24 hrs. post seeding. For each well, all cells which were attached to the wells' bottom were lifted by trypsinization (0.25% trypsin-EDTA) and mixed with cells which might be present in culture media. Thus, the number of cells unattached/not entrapped within the scaffolds was measured by cell-counting. Seeding efficiency was then calculated by equation 3:

$$\text{Seeding efficiency [\%]} = \left[\frac{\text{Initially seeded cells} - \text{Unattached cells}}{\text{Initially seeded cells}}\right] \times 100 \quad (3)$$

Viability

Cell viability within F.D mold-based scaffolds of example 1 was evaluated 24 hrs. post seeding by a Calcein-Ethidium homodimer I Live/Dead assay. In this assay, the nonfluorescent calcein-acetoxymethyl (AM) is converted to a green-fluorescent calcein after acetoxymethyl ester hydrolysis by intracellular esterases. Imaging of the stained scaffolds was done with a confocal microscope (LSM700, Zeiss), with 10× magnifications.

Live cells were stained with fluorescent calcein inside their cytoplasm (green; excitation/emission ~495 nm/~515 nm). Dead cells were stained with Ethidium Bromide (red; excitation/emission ~495 nm/~635 nm), indicating on its intercalation into nucleic acids inside their nucleus—accessible due their damaged membranes.

Finally, image analysis was carried out using ImageJ software, to count the dead and live cell numbers separately, according to each imaging channel. Thresholding was determined for each channel separately: the Huang and Default auto-thresholding algorithms were chosen for the Calcein and Ethidium channels, respectively.

Calcein and Ethidium quantifications were then calculated using "analyze particles" module, yielding the live and dead cell numbers. Finally, viability was calculated for each sample as described below, in equation 4:

$$\text{Cell viability [\%]} = \left[\frac{\text{Live cells}}{\text{Live cells} + \text{Dead cells}}\right] \times 100 \quad (4)$$

Each scaffold type was measured 3 times, with two internal imagining replicates of each sample, thus each result represents the average of 6 calculations.

Overall cellular metabolic activity of BSCs seeded on the F.D mold-based scaffolds of example 1 was determined by an Alamar-Blue assay, based on resazurin reduction by the cells. At 3 pre-determined time points during the 3D proliferation phase (1, 4 and 7-day post seeding) all samples were incubated with medium containing 10% Alamar Blue. Wells with 10% Alamar solution served as blank. The solutions were then transferred (with technical triplicates) to a 96 flat-bottom well plate. Fluorescence was measured using excitation of 555 nm & emission of 585 nm wavelengths, using a Varioskan LUX plate reader (ThermoFisher). For each sample, measured values of days 4 and 7 were normalized to the value obtained at day 1. 3-4 replicates were done for each scaffold type (N=3-4).

Example 8—Cell Culture Results

To evaluate initial cell-biomaterial interactions essential for further cell-cultivation, BSCs were seeded on the three Alginate:RGD containing F.D scaffolds. A negative control of non-modified Alginate scaffold was fabricated and seeded as well.

Figure 5A:
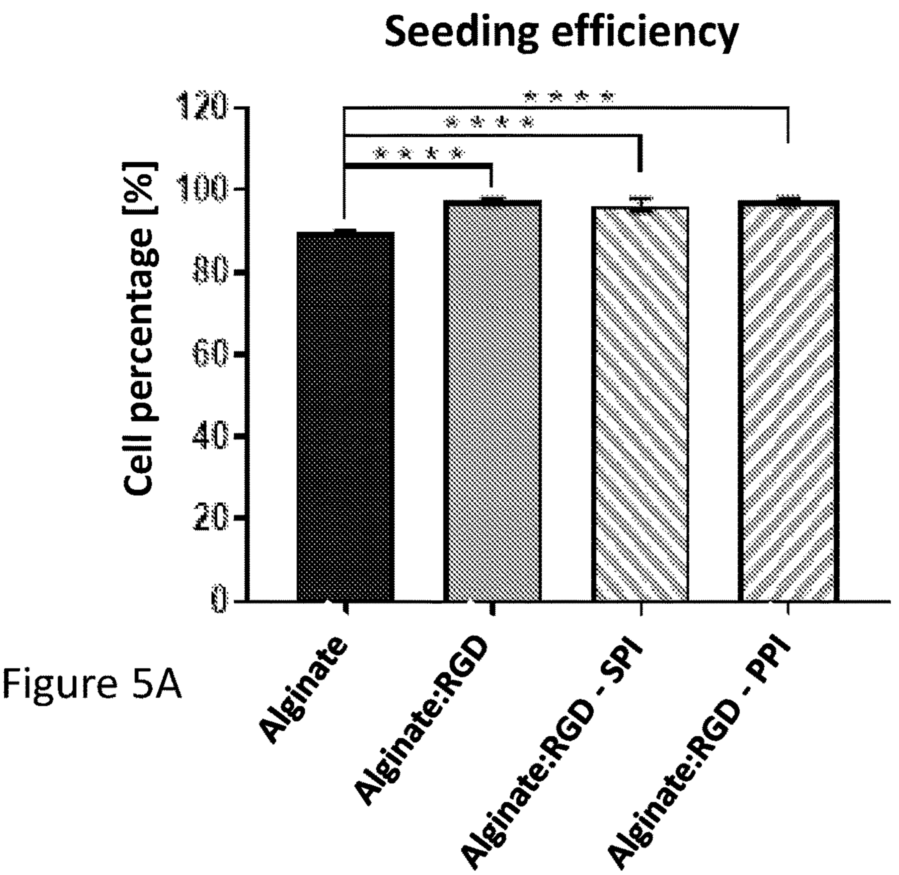
FIGS. 5A-B show results for initial cell-biomaterial interactions, 24 hrs. post seeding: the seeding efficiency (FIG. 5A), and viability (FIG. 5B) of BSCs passage 2 were assessed. Statistical analysis was done for both parameters using Prism's One-Way ANOVA (Seeding efficiency: N=3, **** represents p-value <0.0001. Viability: N=6).
Figure 5B:
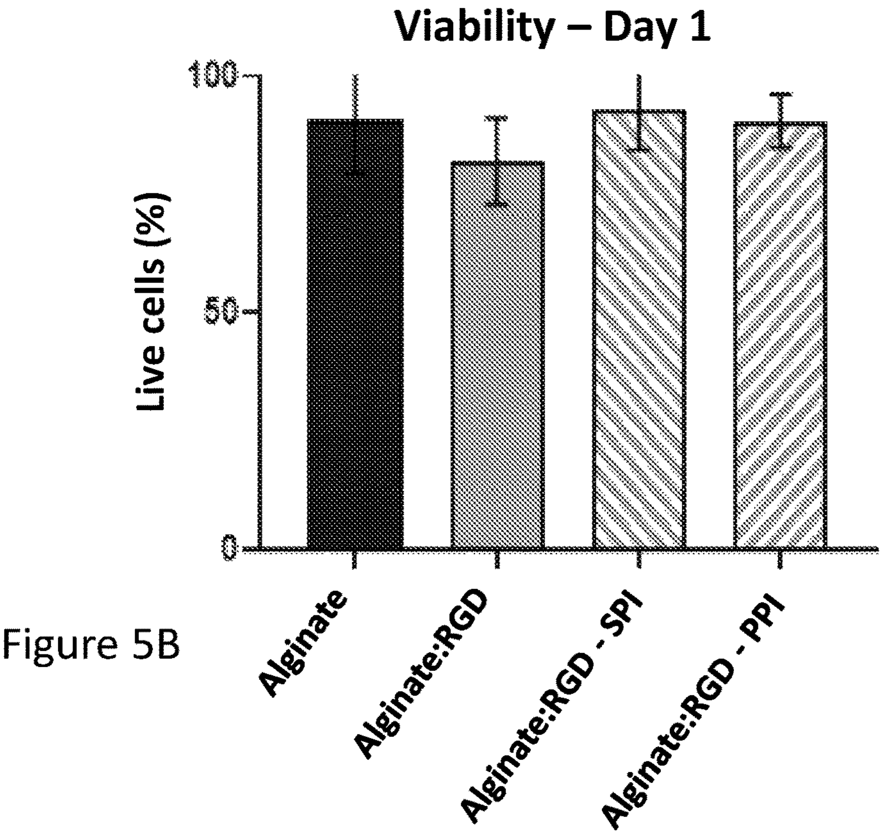

Seeding efficiency and BSCs viability were then assessed 24 hrs. post seeding (FIGS. 5A and 5B).

All combinations showed similar results regarding cell seeding efficiency (FIG. 5A), except for the non-modified Alginate (p-values <0.0001). Although all measured absolute values were high, there was a significant decrease in remained cells on the non-modified Alginate scaffolds. This composition may have contained insufficient attachment sites for the seeded cells, potentially causing the cells to maintain aggregated formations situated within the scaffold's pores.

Live/Dead images of Calcein stained BSCs seeded on non-modified Alginate was performed and indicated an aggregated cellular morphology. In terms of cell viability obtained from the Live/Dead assay, the cell coverage was quantified and the image analysis is shown in FIG. 5B, where it can be seen that all scaffold types exhibited similarly high values (p-value >0.05), indicating the non-cytotoxic nature of all used materials.

Overall, protein addition of either SPI or PPI to Alginate:RGD did not hinder initial cell-biomaterial interactions.

Example 9—DiI Staining and BSCs Coverage Analysis

For assessing cell coverage of the F.D mold-based scaffolds of example 1 or cell attachment to the 3D printed scaffolds of example 3, BSCs, passage 2 (P.2) were pre-stained with 5 μg/ml DiI (Thermo Scientific, D282), an efficient fluorescent lipophilic dye for cell labeling due to its incorporation into their membrane.

F.D mold-based scaffolds seeded with DiI stained BSCs were cultured for 1 week with proliferation medium and were later imaged for DiI fluorescence using confocal microscopy, with 5× magnification and 2×2 tile scan. Maximal intensity projection was performed, and all images were then processed using FIJI software. Thresholding was determined for all images by the Huang auto-thresholding algorithm, available in ImageJ. Then, the BSCs coverage was measured for each image according to the percentage of fluorescent area, of a chosen sampling area of 4.5 mm diameter circle.

Example 10—Scaffold Immunostaining for Myogenic Markers

Both F.D and 3D-printed scaffolds were taken for immunostaining and imaging after 1-week of proliferation phase and 1-week differentiation phase. Initially, samples were fixed in 4% paraformaldehyde (PFA; Electron Microscopy Sciences) diluted in PBS and subsequently washed 3 times with PBS. Cell membranes were later permeabilized with Triton X-100 (Deajung, 8566-4400) diluted in PBS. Subsequently, washings were performed 3 times with PBS. The scaffolds were then immersed in blocking serum for 1 hr. at room temperature or kept at 4° C. overnight. Scaffolds were then incubated with solution containing primary antibodies for Desmin and Myogenin detection (goat α-desmin, sc-52903 1:100, Santa Cruz Biotechnology and mouse α-myogenin, sc-52903, 1:50, Santa Cruz Biotechnology). All scaffolds were washed 3 times with PBS, then incubated with secondary antibodies and DAPI (1:1000) diluted in PBS. (1:100 Cy5 donkey α-goat, 705-175-147, Jackson and 1:400 Alexa Fluor 488 donkey α-mouse IgG H+L, Life Technologies). Scaffolds were then washed 3 times with PBS and stored at 4° C. Imaging was done using Zeiss LSM700 inverted confocal microscope (Carl Zeiss) and ZEN software (Carl Zeiss).

Example 11—RNA Extraction & qPCR

F.D mold-based scaffolds seeded with BSCs were taken for RNA extraction and gene expression analysis, at the end of the differentiation phase. RNA extraction was performed with RNeasy Mini Kit (QAIGEN), according to the manufacturer's instructions: Initially, scaffolds were washed with PBS and minced using scissors. Then they were homogenized in a tube containing buffer RLT+β-mercaptoethanol. They were later centrifuged for 3 min, 14,100 g before extracting the supernatants into new 2 ml tubes containing 70% ETOH, at 1:1 ratio. Samples were then transferred into columns and centrifuged for 15 sec, 8000 g. Flow through was removed and the rest of the samples were reloaded, and centrifuged for 15 sec, 8000 g. RW1 buffer was added into the columns, which was then centrifuged at 8000 g. RPE was added to the columns, which was then centrifuged for 15 sec, 8000 g. This was repeated and columns were centrifuged for 2 min, 8000 g and then for 1 min, at maximum speed. Finally, DNase-RNase-free DDW (400) were added into the columns, and centrifuged for 1 min, 8000×g. RNA concentration was then measured using NanoDrop (Thermo Fisher). cDNA was subsequently prepared using the High-Capacity cDNA Reverse Transcription Kit (ABI #4374966), according to the manufacturer's instructions. qPCR was performed using the RNA TaqMan™ Fast Universal PCR Master Mix (2×), no AmpErase™ UNG (ABI #4352042). The following primers were used: MyoG (Bt03258929; ThermoFisher), MyoD (Bt04282788; ThermoFisher) and 18S (Hs03003631; ThermoFisher). 5 ng of cDNA was used for each reaction, according to the manufacturer's instructions. The reaction was run in the 7300ABI system (according to ABI 7300 fast program). Data analysis was done with the 7500 Software v2.3. Results are presented as 2-Δct (after normalization according to the 18 s housekeeping gene).

Statistical analysis was performed using Prism (GraphPad), version 8.4.2. One-way or two-way ANOVA were performed, with post-hoc differences resolved by using Tukey's multiple comparison test. All values are expressed as mean±SD.

Example 12—Cell Cultivation of F.D Scaffolds

Figure 6A:
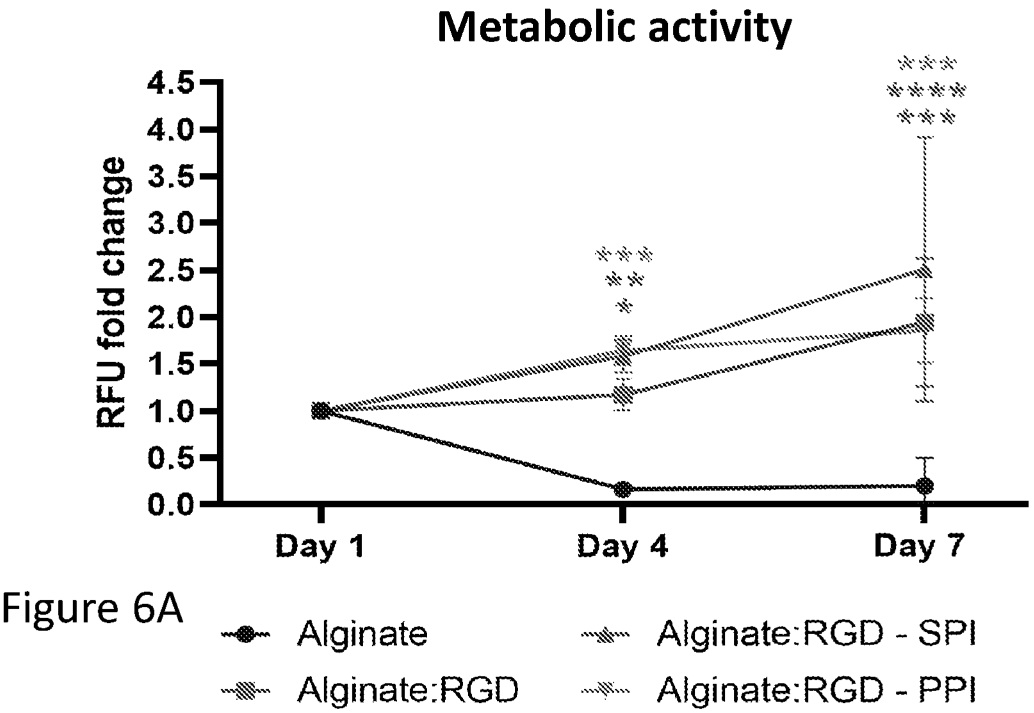
FIGS. 6A-B show results for BSCs growth on freeze-dried scaffolds during 1-week proliferation phase. Overall cellular metabolic activity changes (FIG. 6A), and scaffold final coverage by the BSCs (FIG. 6B) were assessed. Changes in fluorescence (RFU) were calculated by normalizing values to the value at day 1 of each sample. For scaffold coverage analysis, BSCs were dyed with DiI (red) before being seeded, enabling Confocal imaging with 5× magnification & image analysis by FIJI. Statistical analysis was done using a Two-Way ANOVA (for A, N=3-4) or One-Way ANOVA (for B, N=3).
Figure 6B:
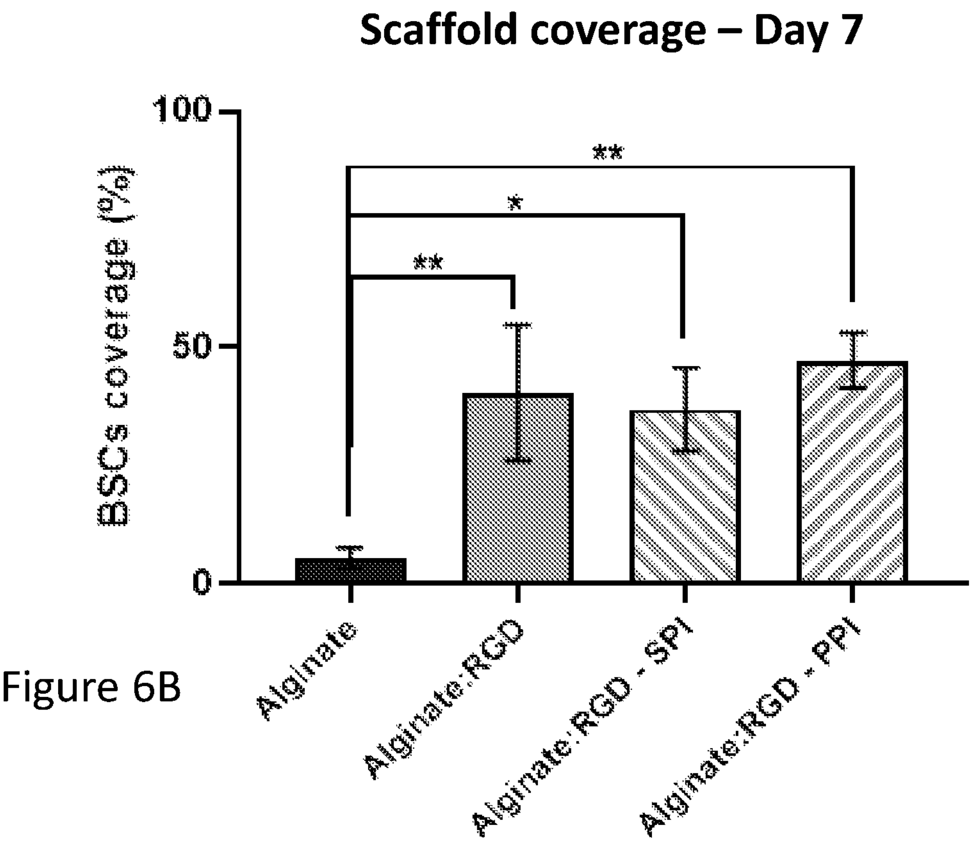

As all findings indicated the protein-enriched scaffolds were promising for further BSCs cultivation, BSCs were seeded on Alginate:RGD, Alginate:RGD-SPI, Alginate:RGD-PPI, and non-modified Alginate F.D mold-based scaffolds, and left to proliferate for 7 days with suitable medium. Overall cellular metabolism changes were investigated during the mentioned culturing period, and final scaffold coverage by DiI-stained cells was assessed at day 7 (FIGS. 6A-B).

Results from Alamar Blue assay (FIG. 6A) show an increased fluorescence overtime compared to measurements taken at day 1, for BSCs seeded on all Alginate:RGD containing scaffolds, indicating on increased metabolic activity via Resazurin reduction. However, the fluorescence measured for the BSCs seeded on non-modified Alginate decreased compared to day 1, reaching significantly lower values overtime compared to the other scaffold types. Additionally, there were no differences between results obtained for Alginate:RGD alone, or the two protein-enriched types (p-value >0.05).

Representative DiI stained BSCs images showed a clustered shape of few remained cells on the non-modified Alginate compared to all other types, which exhibited visual cell spreading. For determining mold-based scaffold coverage by the cells after 7 days of proliferation phase (FIG. 6B), analysis of the DiI stained BSCs images was performed using ImageJ software. The cell coverages were similar between all Alginate:RGD containing scaffolds (all around 40%), while a significantly lower value was obtained for the non-modified Alginate (~5%).

Overall, all trends indicate on enhanced cellular activity of the BSCs on Alginate:RGD containing scaffolds, unimpaired by protein addition.

To evaluate whether the protein-enriched F.D mold-based scaffolds could maintain BSCs maturation capabilities, BSCs were seeded on the three Alginate:RGD containing types and cultivated for two weeks with suitable proliferation (1 week) and subsequent differentiation (1 week) media. Samples were then taken for Immunostaining and q-RT-PCR gene expression assays that were performed against myogenesis markers (FIGS. 7A-C).

Figure 7A:
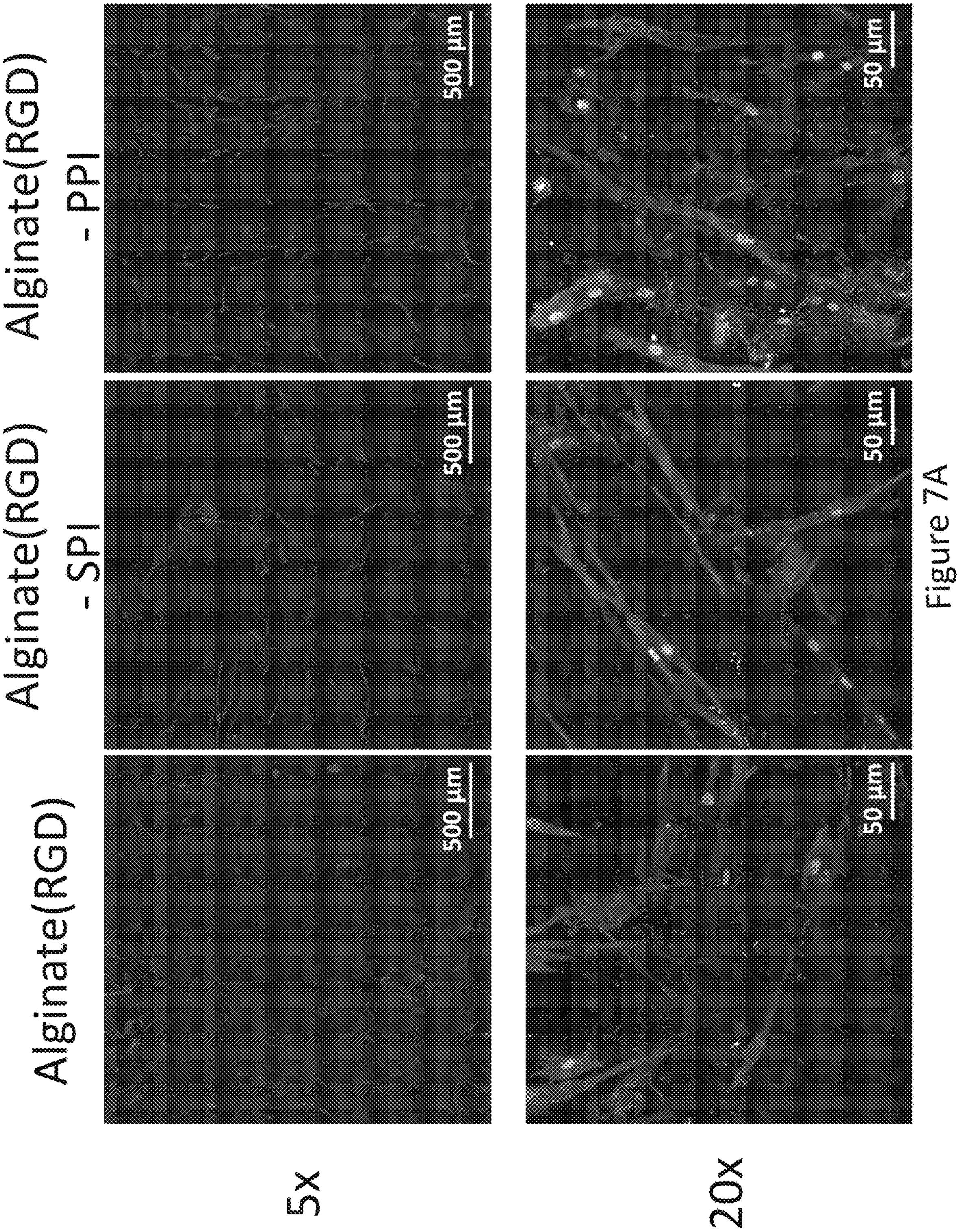
FIGS. 7A-C show results for BSCs differentiation & myogenic gene expression on freeze-dried scaffolds. BSCs were left to proliferate (1 week) and differentiate (1 week) on protein containing & non containing scaffolds.
Figure 7B:
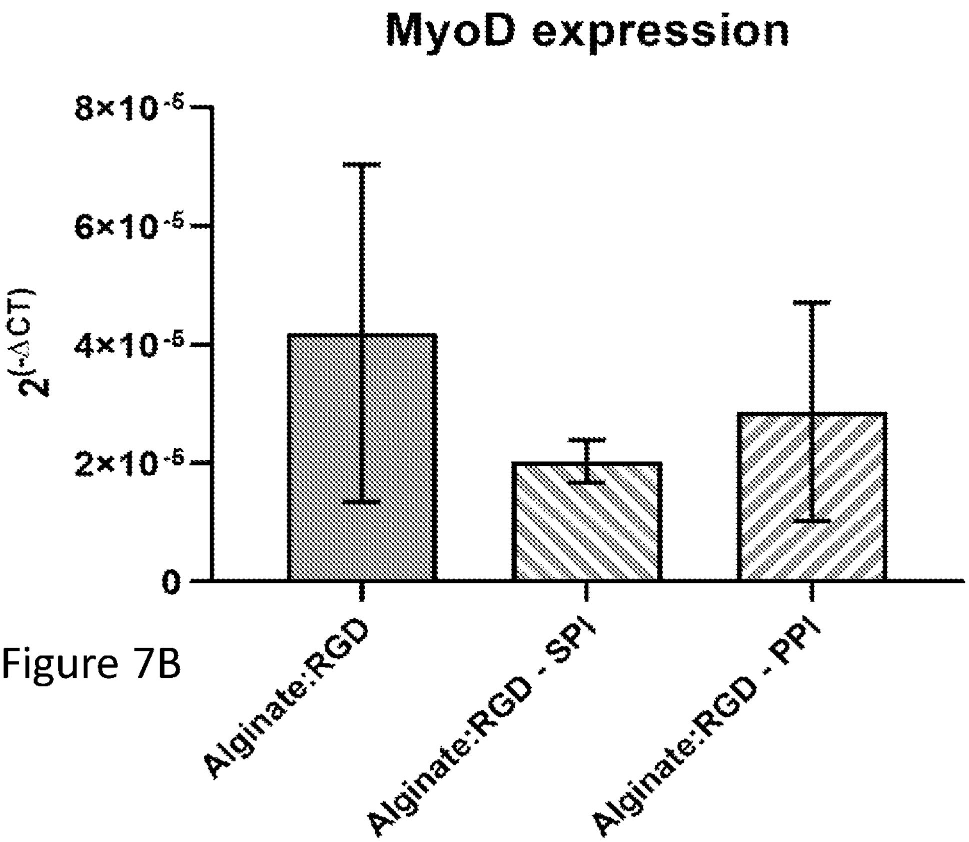
Figure 7C:
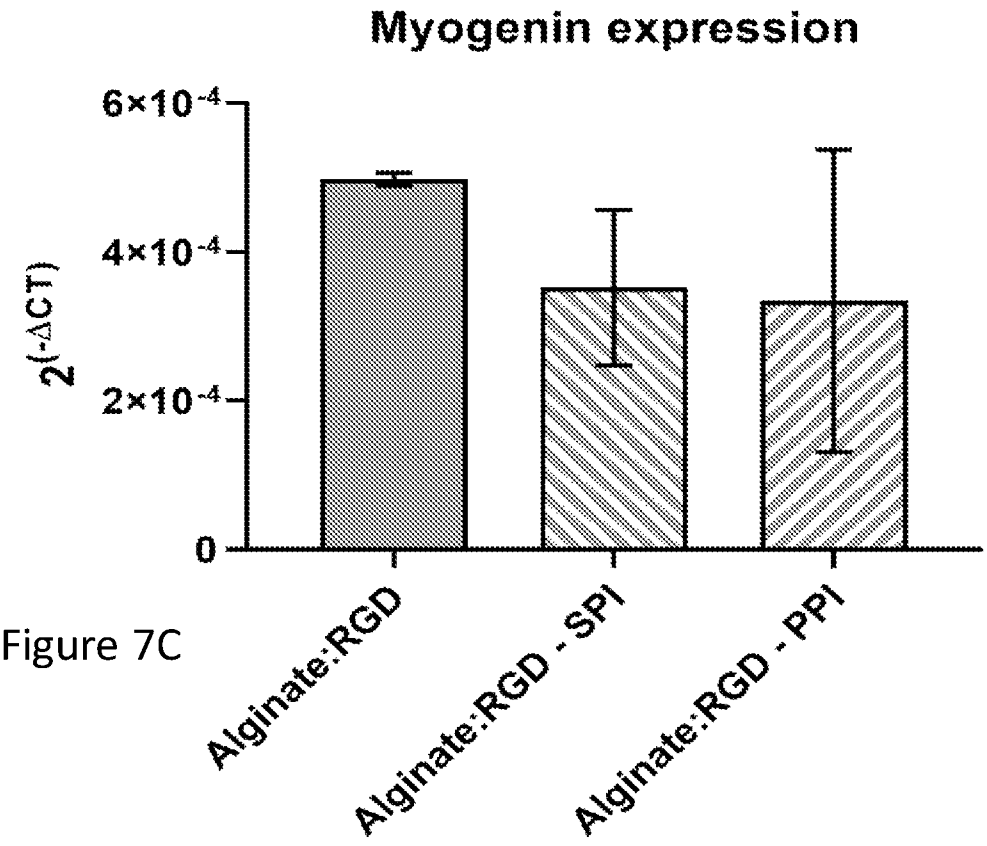

As observed by confocal imaging, differentiation of the BSCs on all scaffolds was achieved (FIG. 7A). The presence of Desmin was clearly confirmed—a subunit protein of intermediate filaments in muscle tissue, known to be at low concentration within replicating myoblasts and satellite cells, while high in differentiated myotubes. Moreover, Myogenin—a transcription factor essential for the transition of proliferating myoblasts into myotubes, was also detected in all three types.

In addition, gene expression examination was conducted for MyoD and Myogenin, as they play crucial roles as transcription factors during differentiation. The results for both examined genes (FIGS. 7B and 7C) further show no significant differences in BSCs differentiation and maturation between the three scaffold types (p-values >0.05), all exhibiting similar profiles.

All findings obtained from the mold-based F.D scaffolds indicates that protein-enriched compositions are promising candidates for further research, and therefore they were assessed as potential bio-inks for customizable 3D bioprinting of scaffolds, intended for BSC cultivation.

Example 13—3D Printed Results

The 3D-printed scaffolds, from example 3, were analyzed for BSCs attachment and differentiation. For initial cell-biomaterial interaction assessments, the following sterile 3D-printed grid scaffolds made of Alginate:RGD-PPI (1%-1% w/v) (as in FIG. 3E, comprising 3-layered scaffold) were seeded with DiI stained BSCs, according to the following protocol:

BSCs P.2 were initially dyed with DiI, and then seeded on the printed 3D scaffolds (post-printing seeding), which were kept post printing in 100 mM Calcium solution until usage (without freeze-drying). After medium washes of the scaffolds, they were seeded with a cell concentration similar to the one used for the F.D scaffolds: $10^5$ to $10^6$ cells/ml medium. All scaffolds were kept under 37° C. for 1 hr, for initial cell attachment. Proliferation medium addition was added afterwards.

Figure 8A:
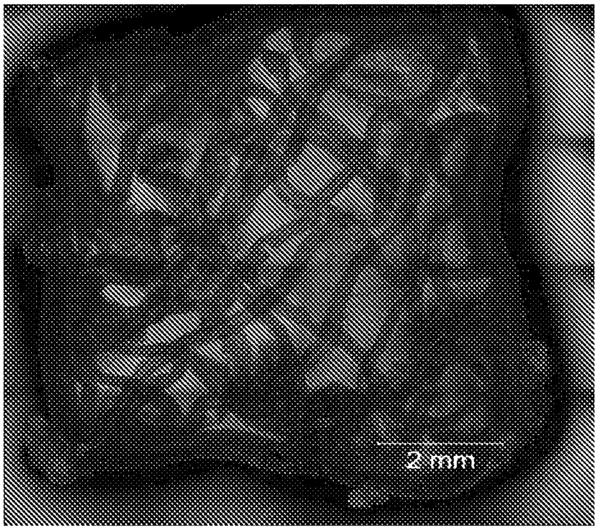
FIGS. 8A-G show results for attachment, spreading and differentiation assessments of BSCs seeded on 3D-printed Alginate:RGD-PPI scaffolds.
Figure 8B:
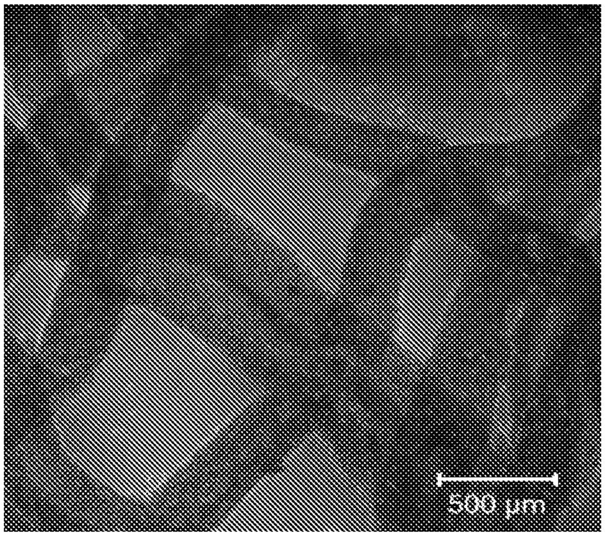
Figure 8C:
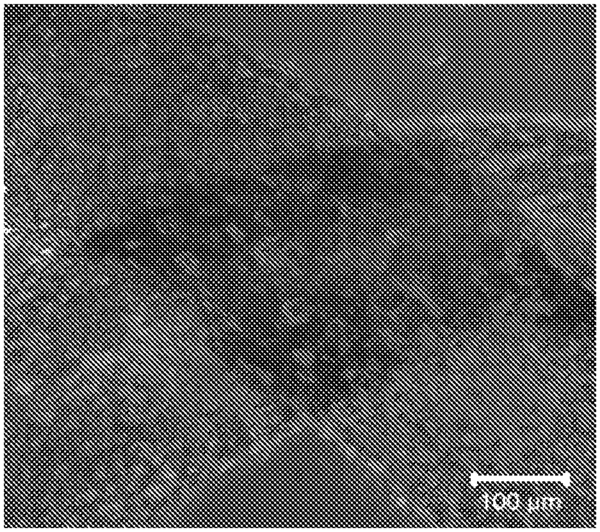

Confocal images were taken 7 days post seeding, with 5× &10× magnifications, (FIGS. 8A-C). It can be seen that successful cellular attachment and spreading was achieved on the 3D printed scaffolds.

As 'post-printing seeding' was enabled by the suggested fabrication process, BSCs differentiation was subsequently evaluated as well.

For BSCs maturation assessments, 3D printed scaffolds based on Alginate:RGD-SPI and Alginate:RGD-PPI (as in FIG. 3G, comprising 4 layers) with a dense pattern of parallel strands were fabricated (see example 3), freeze-dried, and sterilized.

After sterilization and re-hydration with a PBS solution, the 3D printed scaffolds were moved onto 1 cm×1 cm PDMS square surfaces and held by 4 needles (one in each corner). Then, all scaffolds were seeded with seeding concentration of 1.5M cells/100 μl media, to cover the scaffolds. All scaffolds were kept under 37° C. for 1 hr, for initial cell attachment. Expansion medium was added afterwards for overnight incubation, followed by 1-week differentiation phase with differentiation medium.

Figure 8D:
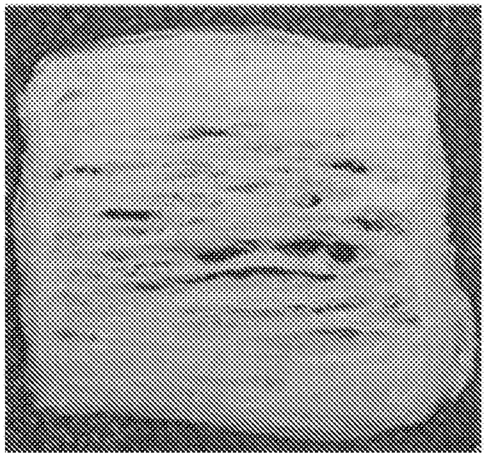
Figure 8E:
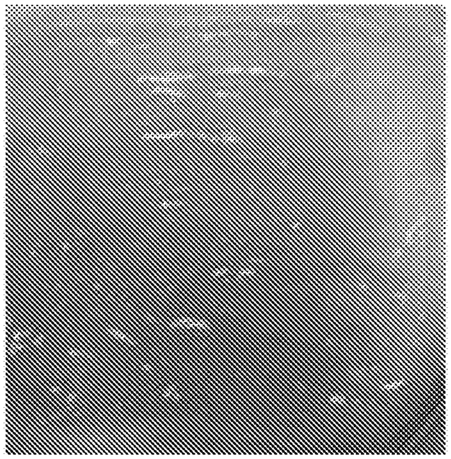

FIG. 8D shows regular images of freeze dried and sterilized scaffolds, and 8E shows image of the seeded 3D printed scaffolds taken by regular camera. Freeze-drying of the 3D-printed scaffolds was successful, showing intact fabricated scaffolds with the desired geometry.

Figure 8F:
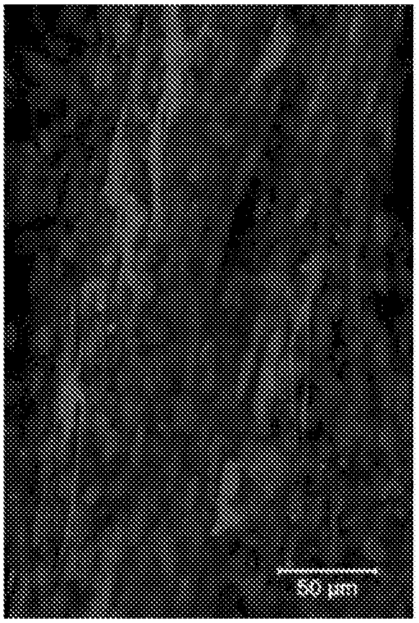
Figure 8G:
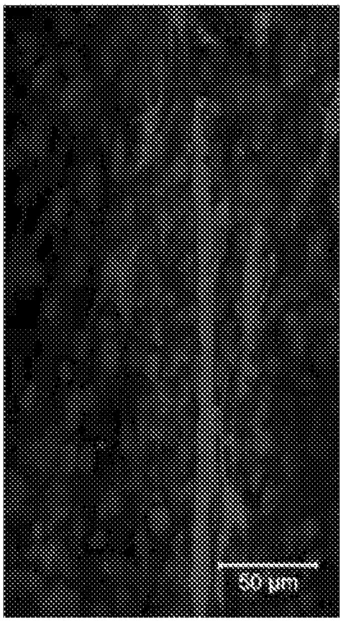

FIGS. 8F and 8G show confocal images of samples which were immunostained against Desmin, with the addition of DAPI for general nuclear staining. The two immunostaining images show the expression of Desmin (Red, myogenic marker, appears in the figure as light grey) in differentiating cells (blue represents the DAPI, cells nuclei, appears in the figure as dark grey). The images were taken using the confocal microscope, scale bars=50 μm). It was found that the BSCs both attached to the 3D scaffolds and differentiated, as confirmed by the presence of desmin (Myotubes were observed by visible Desmin signals).

Therefore, concluding all obtained results, the 3D scaffolds successfully supported muscle cell attachment and maturation thereon.

Example 14—3D Printed Rib-Eye Shaped Scaffold

A large multi-layered 3D printed scaffold was fabricated, having an external shape mimicking that of a rib-eye steak, and having external dimensions of 10 cm×5 cm×0.5 cm. The 3D printed scaffold was based on the printing of 2 types of Alginate-PPI hydrogels (1%-2% w/v final concentrations, with and without food colors) with cells, to eventually create a large-scale steak-like scaffold with white and red regions, having an inner, fibrous texture, configured to mimic muscle and fat tissues as in marbled steaks.

Initially, the alginate (and optionally food colors) was added as powders to a 2% PPI solution, followed by mixing overnight, to form an aqueous solution having an Alginate-PPI concentration of 1%-2% w/v. The resulting aqueous solution had a white color (due to the presence of the PPI) and was mixed with Adipocytes (matured BMSC) at a concentration of about $10^5$ to $10^6$ cells/ml. A red-colored ink was prepared by adding Brown Apple and Beet powders to the aqueous solution, and further mixing with BSCs at a concentration of about $10^5$ to $10^6$ cells/ml. Thus, a white colored and a red colored aqueous solutions were prepared, wherein both solutions contained cells therein, and used to 3D print a multi-layer scaffold.

The multi-layer scaffold was fabricated using a 3D printer similarly as disclosed herein above.

Figure 9A:
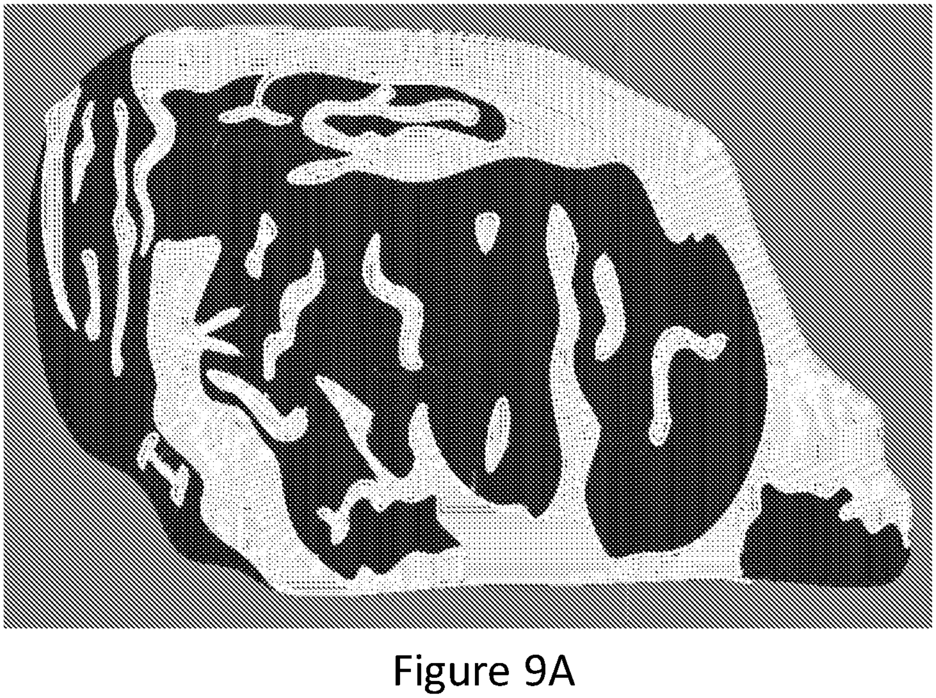
FIGS. 9A-B show images of a Rib-eye like scaffold model design intended for 3D-printing.
Figure 9B:
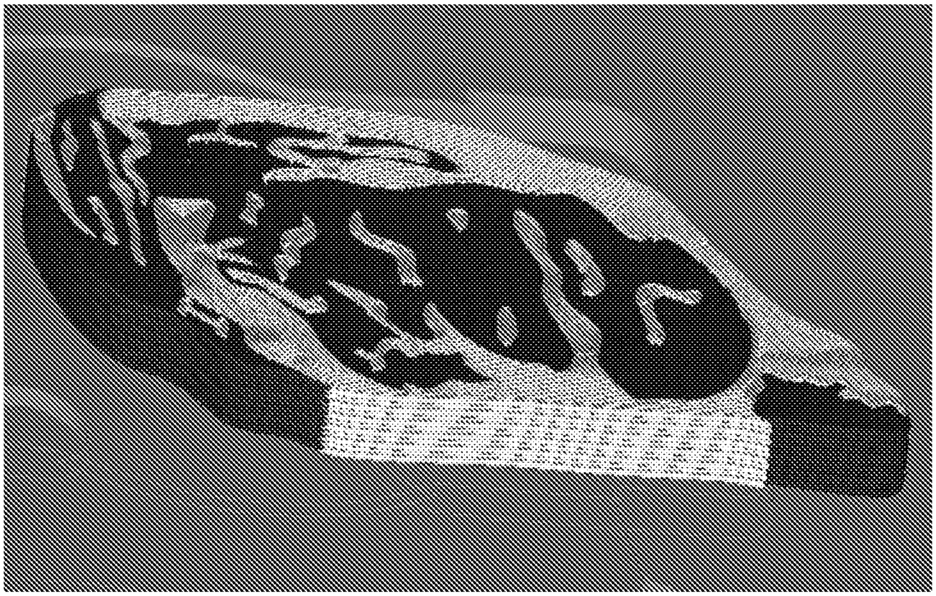
Figure 10A:
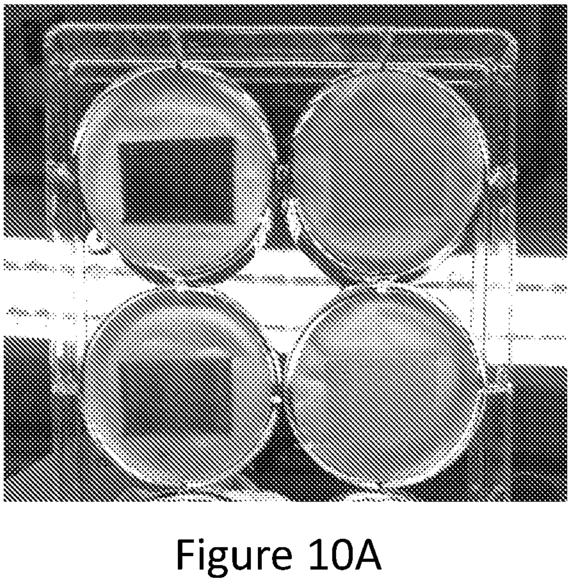
FIGS. 10A-E show images of square-shaped 3D printed scaffold with a fibrous inner pattern, made of 1% w/v-1% w/v PPI-Alginate: views in perspective (FIGS. 10A-D), and cross-sectional view (FIG. 10E).
Figure 10B:
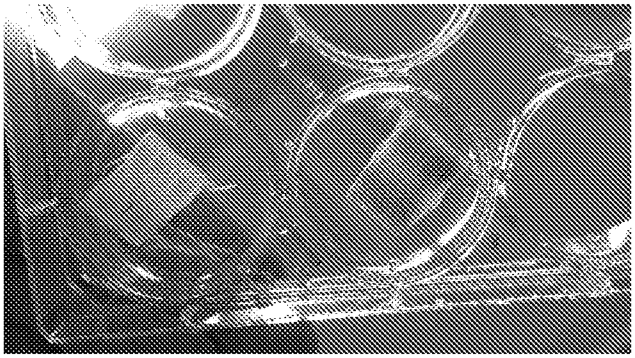
Figure 10C:
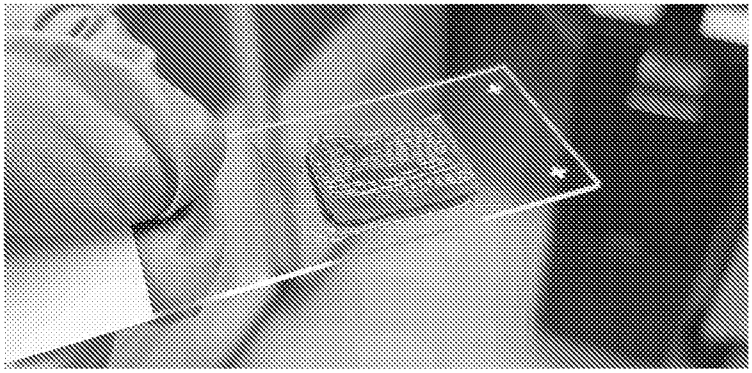
Figure 10D:
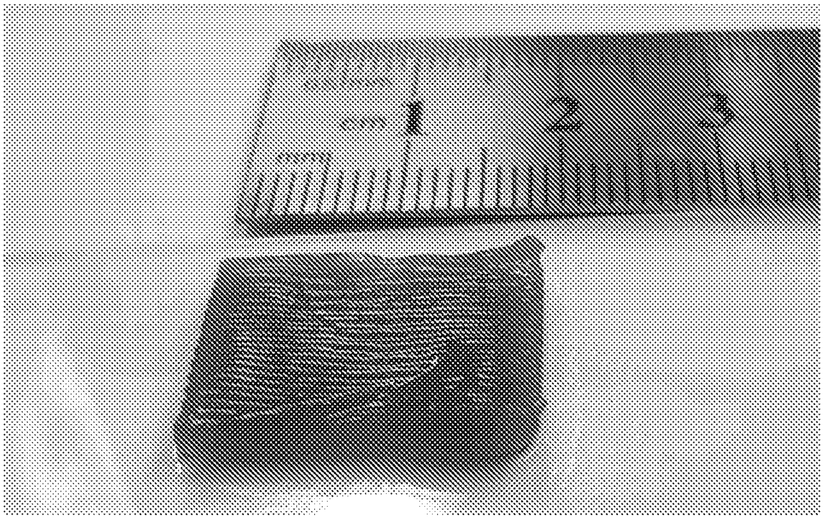
Figure 10E:
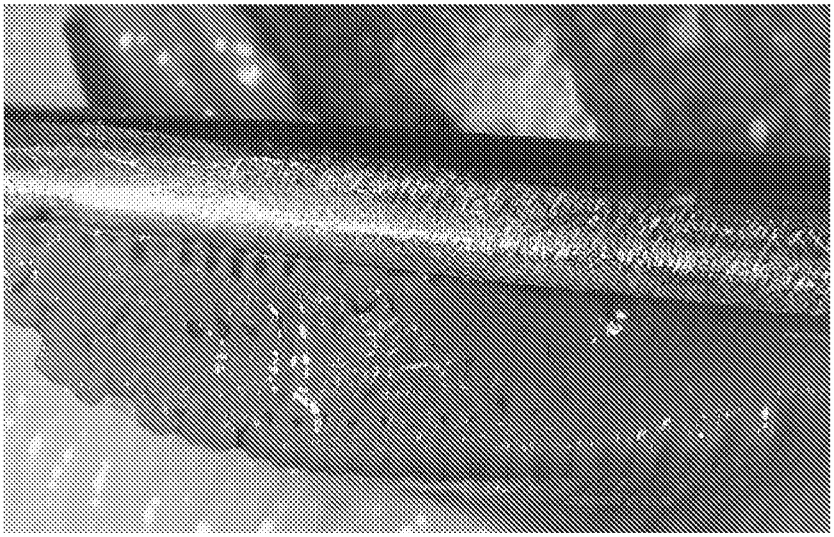

The desired 3D shape of the steak-like scaffold (made to resemble the generally familiar shape of a Rib-Eye) was hand-drawn within an imaging software, resulting in a structure consisting of parallel layers, each having parallel strands therein, as shown in FIGS. 9A and 9B. To achieve the final desired 3D printed scaffold, having a thickness of about 0.5 cm, a pattern of 10-11 parallel layers of the designed needle-paths (meaning edible members) were duplicated and 3D printed into a support bath, in a process which was similar to method 100, or specifically method 300, as disclosed herein above. The 3D printer used was BioAssemblyBot 400 by Advances solutions. The printing was done with a printing pressure of 4 psi and 20 mm/sec needle velocity.

Figure 11A:
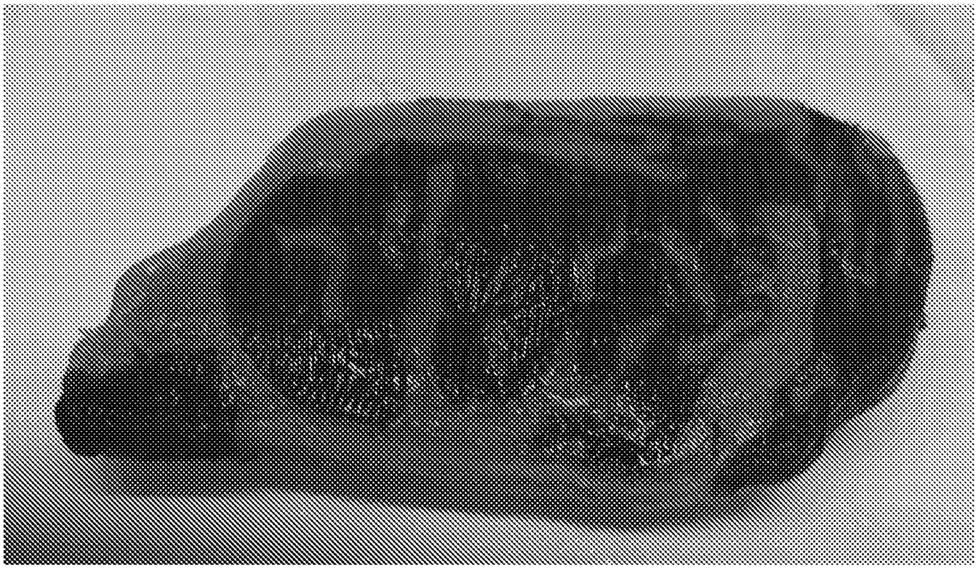
FIGS. 11A-D show images of the resultant 3D printed scaffolds which were fabricated according to the model in FIGS. 9A and 9B; following extraction (FIGS. 11A and 11B), and following frying (FIGS. 11C and 11D).
Figure 11B:
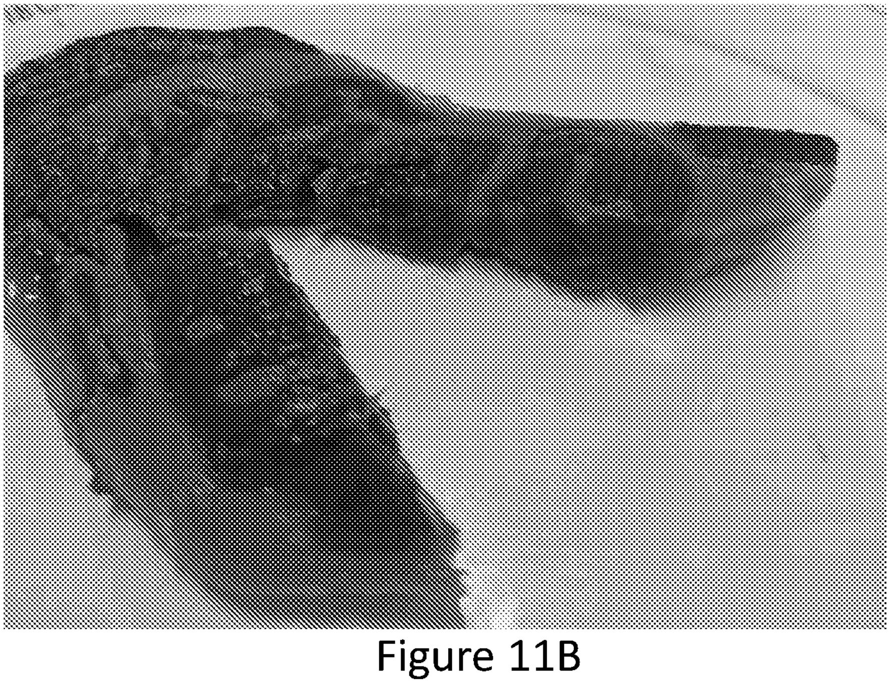

After the desired 3D printed Rib-Eye-like scaffold was fabricated, it was left to crosslink in a 100 mM calcium solution for several hours before performing extraction and frying trials. The desired 3D structure following extraction can be seen in FIGS. 11A and 11B. The desired fibrous structure appeared to be preserved, as seen in FIG. 11B showing a partially divided (i.e., cut) 3D scaffold.

Figure 11C:
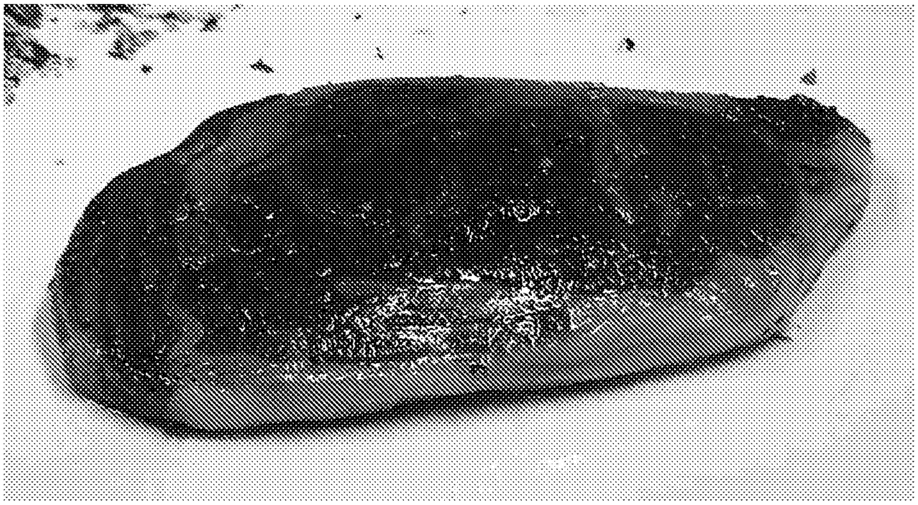
Figure 11D:

After frying the 3D printed steak-like scaffold, there appeared to have a browning effect, resulting in the transition of portions of the 3D printed scaffold to brown colors, thereby mimicking steak-like behavior (appears as dark grey in FIGS. 11C and 11D).

In order to create inner voids within a desired 3D printed scaffold, adapted to achieve an inner fibrous texture made of parallel strands, a slight location shift was made between each two subsequent layers (the length of the shift was half the distance between neighboring strands in the same layer), thus creating voids within the 3D printed scaffold. Similar voids and layer orientation can be seen in FIGS. 10A-E, taken from a smaller, square-shaped scaffold with a unidirectional fibrous inner pattern, made of 1% w/v-1% w/v PPI-Alginate.

Example 15—Cell Spreading in PPI-Alginate:RGD Hydrogel Supplemented with Microparticles As alginate possesses limited biodegradation by mammalian cells, gelatin-microparticles which are meltable at 37° C., were incorporated as pore-forming components ('porogens') within Alginate:RGD-PPI solution, to assess their effect on cell behavior. In order to examine the effect of high cell-density on cellular behavior, BSCs were added to this solution to obtain a final concentration of 50 Million cells/ml. Cell-laden plugs were fabricated, similarly to the scaffolds from example 1, using DiI-stained BSCs P.4 cells, by mixing the cells with the appropriate solution volume. Later, the mixture was casted into the Teflon molds and left to crosslink within 100 mM Calcium (10 mM HEPES) solution (to create 3D hydrogel plugs).

All plugs were supplemented with a complete medium for the initial 4 days, followed by differentiation medium for additional 14 days. Confocal images were taken after immuno-staining was performed at the endpoint of the experiment against Desmin, to identify cell differentiation, using the relevant staining protocol disclosed herein above.

Figure 12A:
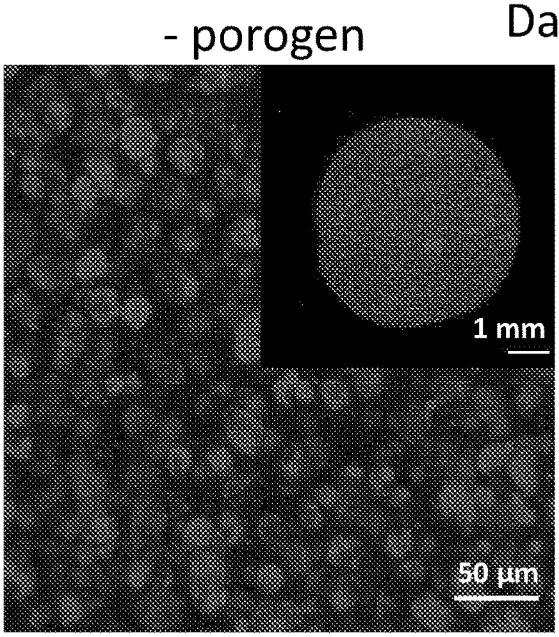
FIGS. 12A-D show confocal microscope images of DiI-stained BSCs spreading and differentiation in hydrogel plugs made of PPI-Alginate:RGD: at day 7, without porogen particles—small image on the top-right corner has a scale bar of 1 mm, and central image has a scale bar of 50 μm (FIG. 12A); with porogen particles—small image on the top-right corner has a scale bar of 1 mm, and central image has a scale bar of 50 μm (FIG. 12B); after 2 weeks cultivation with differentiation medium, with 5× magnification and scale bar 1 mm (FIG. 12C), and 20× magnification and scale bar is 50 μm (FIG. 12D).
Figure 12B:
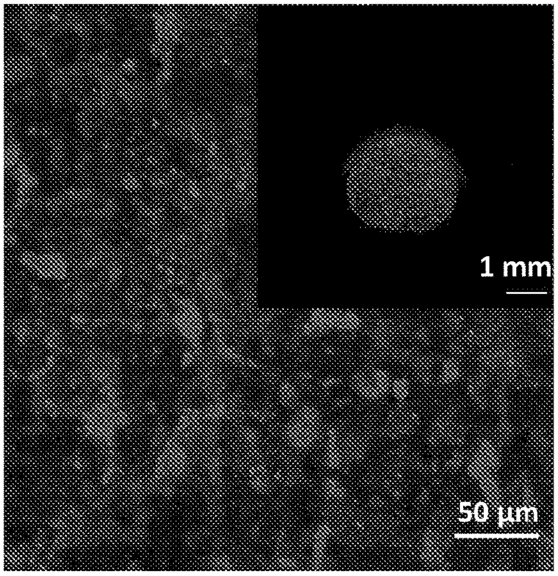
Figure 12C:
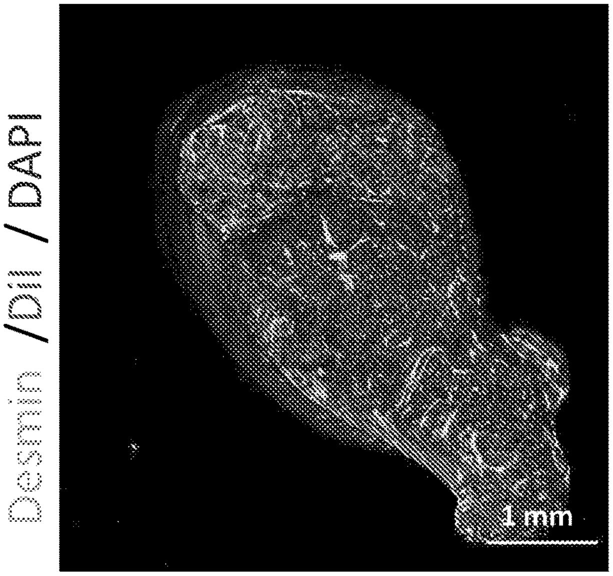
Figure 12D:
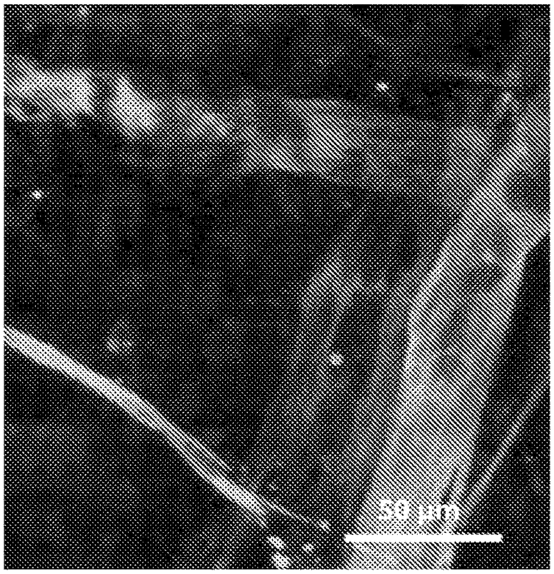

Samples were stained with anti-desmin antibody (staining shown in grey), with the addition of DAPI (staining shown in dark grey), and observed with a Confocal microscope. The plugs originally made with porogen particles shrank significantly after 1 week compared to ones without it (FIGS. 12A-B). Moreover, closer observations revealed spread cells within porogen-supplemented plugs, compared to a rounded BSC morphology within the non-porogen supplemented ones. BSC were also capable of differentiation within such composition—as the presence of desmin was noted by confocal imaging after 2 weeks within initially porogen-supplemented plugs (FIGS. 12C-D). Thus, this promising composition was used in additional steps.

Figure 12E:
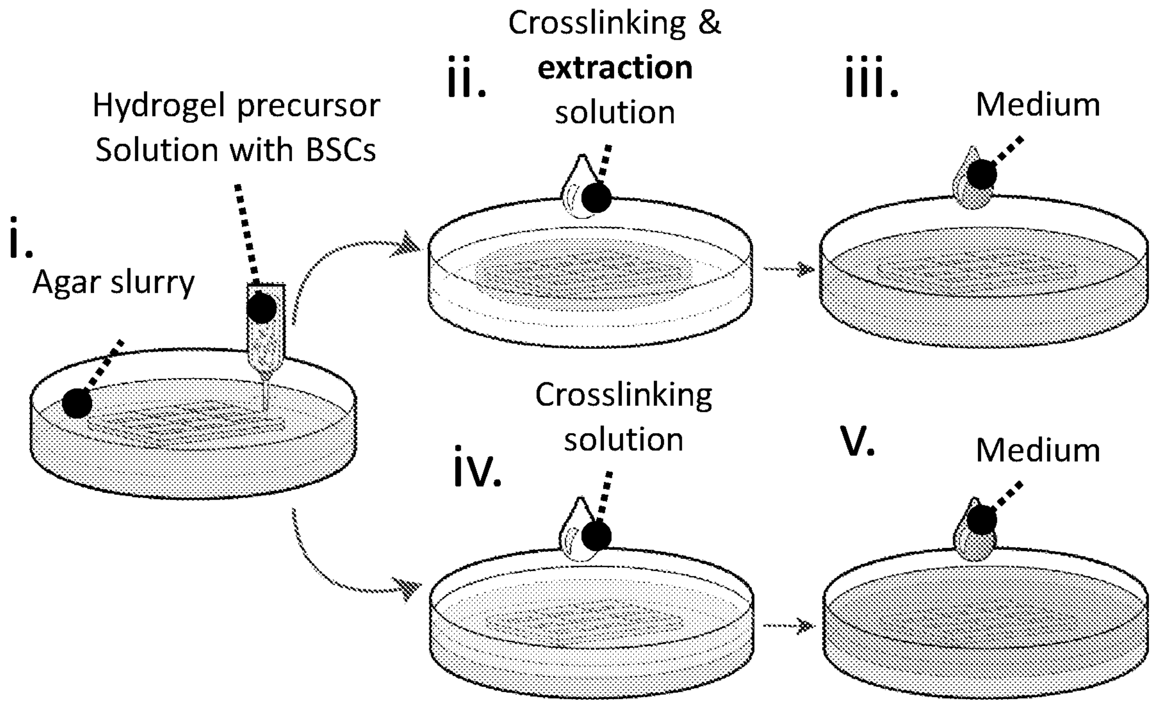
FIG. 12E schematically illustrates a preparation process for a 3D printed scaffold comprising cells based on agar support bath usage: i) BSCs within hydrogel precursor solution are extruded into a Calcium containing support bath, thus becoming encapsulated within the gelled materials during printing. Two cultivation configurations were then used: (ii&iii) Cultivation of extracted constructs: final chemical crosslinking and bath removal were done by gentile pipetting using a solution with higher Calcium concentration. Subsequently, the constructs were supplemented with suitable medium. (iv&v) Cultivation of constructs within the support bath: while the final crosslinking took place with high Calcium concentration solution added on-top of the bath, pipetting was avoided. The cellular constructs were then supplemented with medium on top of the Agar bath.

FIG. 12E schematically illustrates a production process of a 3D scaffold comprising cells encapsulated therewithin, as will be disclosed herein below, which was similar to method 600 as disclosed herein above.

To obtain elevated cell spreading and optionally a highly porous hydrogel, for 3D printing applications, 3D printed scaffolds based on Alginate:RGD-PPI hydrogels with a dense pattern of parallel strands (i.e., edible members) were fabricated. A solution of Alginate:RGD-PPI (1%-1%) was prepared as disclosed herein above, and mixed in a 1:1 weight ratio with a solution containing meltable microparticles (LifeSupport, FluidForm) used as pore-forming components ('porogen'). Then, BSCs were added to the solution (final concentration of $50\times10^6$ cells/ml) with or without the porogen, to form a cell-containing solution used for 3D printing, resulting in cell-containing 3D scaffolds (FIG. 12E, step i.). The production and printing method was similarly to that presented at example 3, and the resulting 3D scaffold resembled that of FIG. 3G, forming printed parallel-patterned scaffolds, however with cells being deposited within the composition at the time of printing. An important advantage of this technique is the cell-encapsulation within the extruded scaffolding material. Thus, unlike other methodologies, in which cells are commonly seeded after scaffold preparation, this technique provides an even cell distribution throughout fabricated 3D scaffolds. The printed cell-containing 3D scaffolds intended for viability assessments were incubated with complete medium for 2 weeks, and were maintained either within the bath or extracted from it for the entire cultivation period.

Figure 12F:
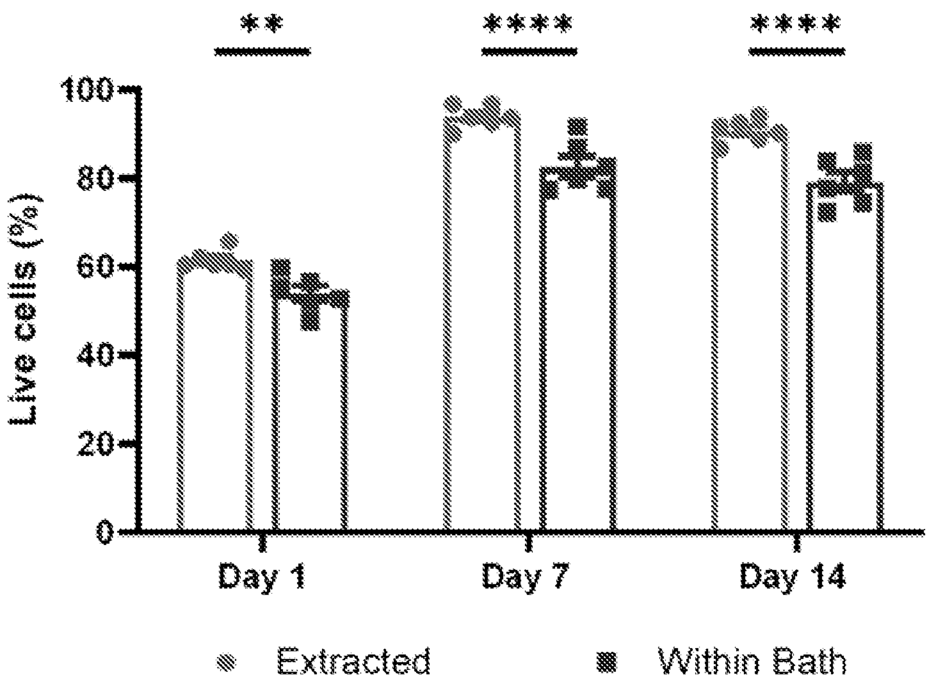
FIGS. 12F-J show BSCs viability, spreading and differentiation in hydrogel 3D scaffolds made of PPI-Alginate: RGD supplemented with porogen particles: statistical analysis was done using Prism's Two-Way ANOVA to assess viability of 3D-printed BSCs with/without the agar support bath for 14 days, N=6. , significant p-values below 0.01, 0.0001 respectively (FIG. 12F); representative images obtained for the Live/Dead cell viability assay at day 14 with 10× magnification and scale bar of 100 μm, within the agar support bath (FIG. 12G); or without the agar support bath (FIG. 12H); For morphology and differentiation assessments of constructs kept within the agar support bath, samples were stained with anti-desmin, phalloidin-TRITC and DAPI, and observed with a confocal microscope at 10× magnification and scale bar of 100 μm, (FIG. 12I), and at 20× magnification and scale bar of 50 μm (FIG. 12**J).
Figure 12G:
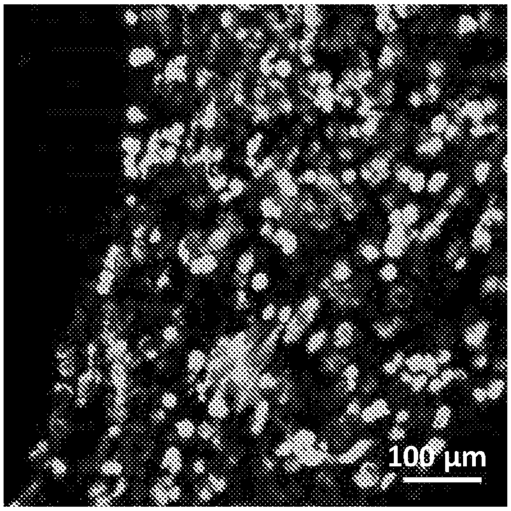
Figure 12H:
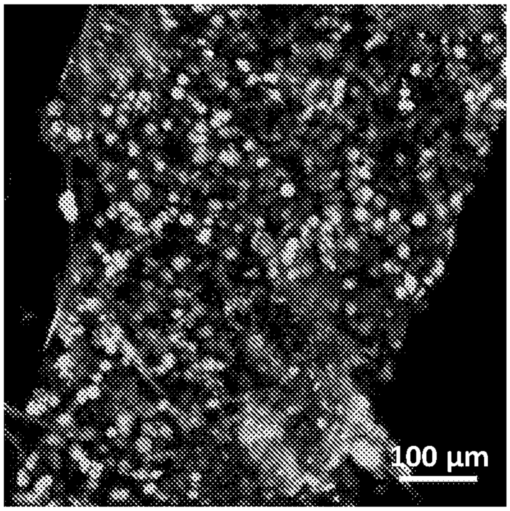

The 3D scaffolds were printed as disclosed above and either extracted from the agar support bath (FIG. 12E, steps ii-iii.), or maintained within it (FIG. 12E, steps iv-v.), during a 2-week cultivation period. According to a standard cell Live/Dead essay, despite non-optimal cell viability at day 1, viability has significantly increased over time (FIGS. 12F-H) in both cultivation configurations (i.e., with/without the agar support bath), with extracted constructs associated with higher cell viability at all tested time points (p-values: 0.0096, <0.0001 and <0.0001 on days 1, 7, and 14, respectively). Thus, the recovery of the cells in scaffolds maintained within the agar bath was possible, albeit, to a somewhat lower degree. As the cultivation of cellular 3D-printed constructs within the support bath could be beneficial for preserving the designed geometry and preventing construct shrinkage, differentiation of BSC was then examined in this configuration.

Figure 12I:
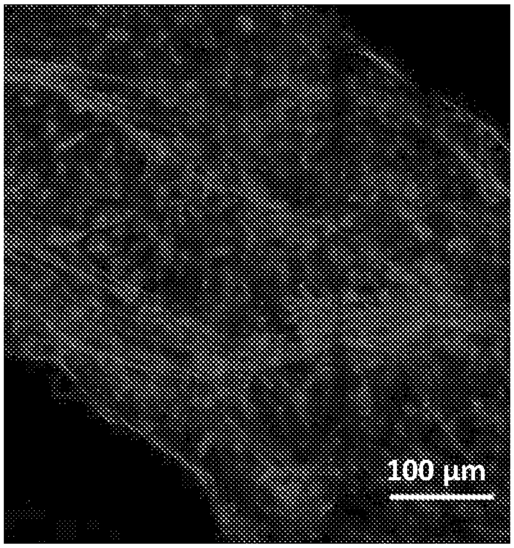
Figure 12J:
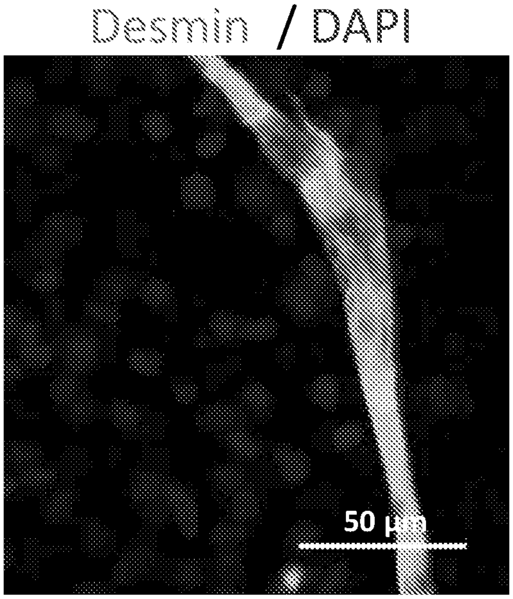

Cellular 3D-printed scaffolds were fabricated and maintained within the agar support bath as previously described, while supplemented with differentiation medium for 2 weeks. After the cultivation period, samples were stained with anti-desmin antibody (light grey), with the addition of phalloidin-TRITC (grey) and DAPI (dark grey), and observed with a Confocal microscope. Some of the BSCs appeared spread and differentiated, as confirmed by the presence of desmin, when cultivating printed scaffolds within the support bath (FIG. 12I-J). Therefore, the proposed fabrication and cultivation configuration of 3D-printed cellular scaffolds allowed cell recovery post printing, and showed potential to allow their maturation, while the overall pre-designed geometry was preserved.

Example 16—3D Printed Scaffold Having Different Hydrogels

Using the compositions and methods of the present invention as disclosed herein above, multiple inks with different characteristics can be printed simultaneously, to create a heterogeneous scaffold made of members with different material concentrations and different material types.

In order to create the 3D printed scaffolds containing parallel strands based on two different cellular compositions, hydrogel compositions having different multiple cell types can be used within a 3D printer having a "multi-material" head that can hold two different syringes, containing two different inks or within 3D printer having at least two different movable printer heads/nozzles.

A first hydrogel composition (also termed "bioink") is comprised of 1% w/v-1% w/v Alginate:RGD-PPI, which is then combined with a 1:1 v/v (volume to volume ratio) Gelatin-microparticles containing solution. Prior to 3D printing, this mixture is combined with a cell pellet (of satellite cells from bovine origin=BSCs) to create $10^5$ to $10^6$ cells/ml cellular concentration. Therefore, this hydrogel composition (or bioink) contains muscle progenitors, which can also be supplemented with meltable particles (acting as porogens) configured to create a highly porous hydrogel, following printing.

An alternative for the first hydrogel composition is a similar composition, except that the Alginate:RGD-PPI is replaced with collagen, and then combined with BSCs.

A second hydrogel composition (or bioink) is comprised of 2% w/v-1% w/v PPI-Alginate. This bioink is combined with mature bovine adipocyte cells, which were previously grown and matured within 1% Alginate plugs and extracted therefrom as described hereinabove, prior to mixing them with the second solution intended for 3D-printing.

The first and second hydrogel compositions (bioinks) are extruded by two different movable printer heads within a 3D printer, in order to simultaneously fabricate neighboring parallel strands within a multiple-layers structure. After 3D printing and extraction, the 3D printed structure is incubated under a Satellite-cells' differentiation and adipose maintenance medium, in order to obtain satellite cells differentiation into mature myotubes, yet preserve the adipocytes' mature state.

Figure 13:
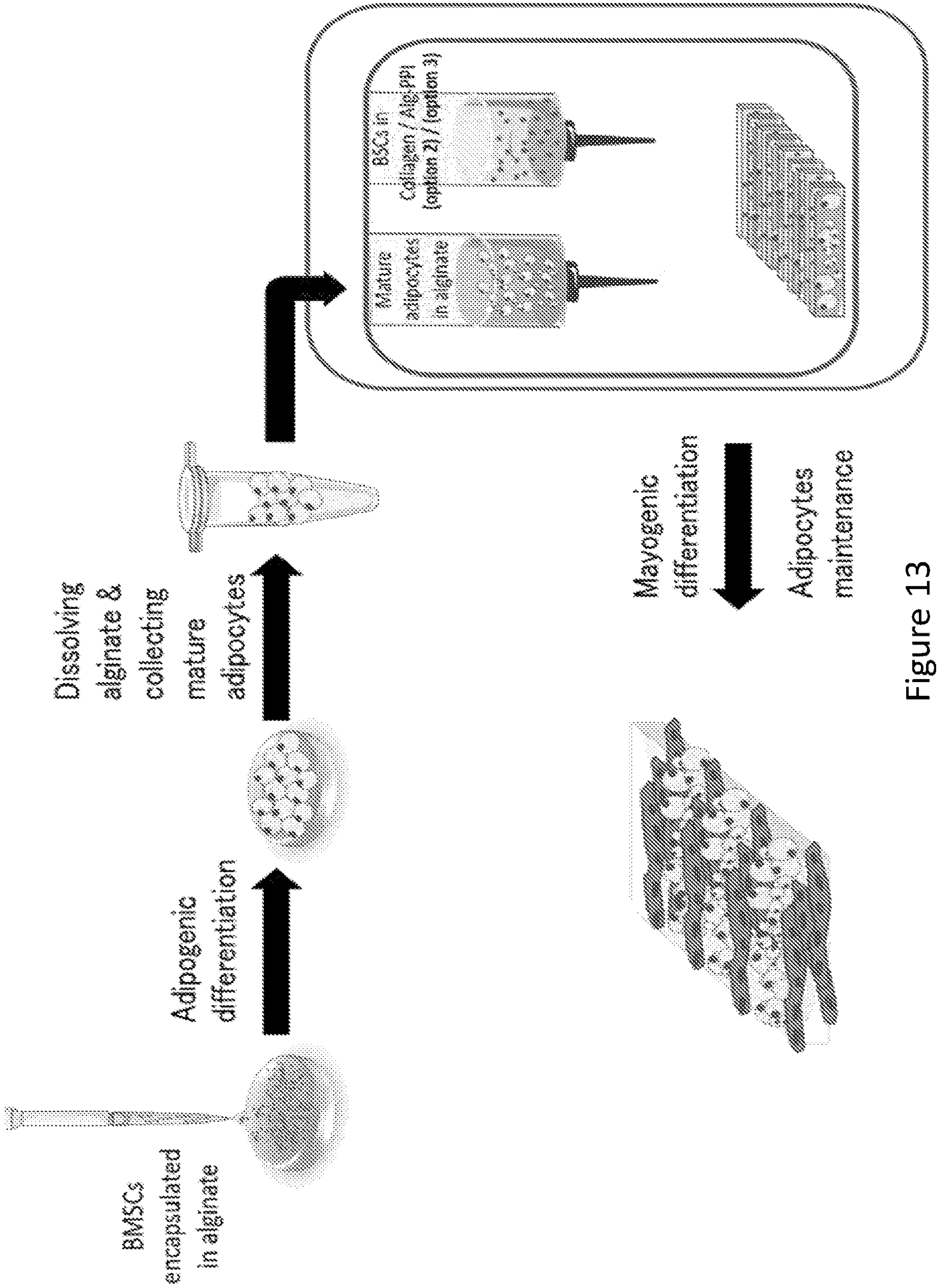
FIG. 13 schematically illustrates a preparation process for 3D printed structures containing two different types of hydrogels, each containing a different cell-type.

FIG. 13 schematically illustrates the production process of the 3D scaffold described herein, which was similar to method 500 as disclosed herein above.

Example 17—3D Printed Scaffold Having Mature Adipocytes 3D printed scaffolds based on Alginate:RGD-PPI hydrogel were 3D printed according the protocol presented in example 3 and then freeze-dried. BSCs were seeded on rehydrated 3D printed—freeze-dried Alginate:RGD-PPI scaffolds, differentiated into myotubes, and then, differentiated Bovine mesenchymal stem cells (BMSCs, aka Adipocytes) suspended in alginate mixture were casted onto the scaffold, and later crosslinked to create a hybrid scaffold containing two cell-types.

BMSCs were suspended in BMSC medium and mixed at a 1:1 ratio with 1% alginate in PBS, forming a solution of 0.5% alginate and 40-100 $10^6$ cells/ml. 3D alginate scaffolds were fabricated on a paper soaked with $CaCl_2$) solution. Teflon molds (6 mm inner diameter, 1 mm thick) were placed on the paper and cell-alginate mixture was pipetted into each mold. Next, $CaCl_2$) solution was added to cover the whole plugs and incubated for 15 min at room temperature. At the end of incubation hydrogels were separated from the molds using tweezers and washed in PBS. Then the plugs were gently transferred into 24-well plate with BMSC medium and placed in the incubator at 37° C. under 5% $CO_2$. This was followed by another 48 hrs. incubation period, after which the medium was changed. Three days post seeding, the seeded BMSCs encapsulated within the alginate hydrogel were transferred to differentiation medium. Then, the alginate hydrogel was dissolved by 55 mM sodium citrate solution. Upon dissolution, the adipocytes were collected and re-encapsulated in the alginate-based composition (also termed "bioink").

Alternately, a denatured PPI-containing solution may replace the alginate for the initial BMSCs maturation stage.

Separately, a scaffold composed of alginate and pea protein (Alginate-PPI) was 3D printed according to a 3D desired structure, underwent freeze-drying and then bovine satellite cells (BSCs) were seeded on the rehydrated-3D printed scaffold and underwent myogenic differentiation.

Figure 14A:
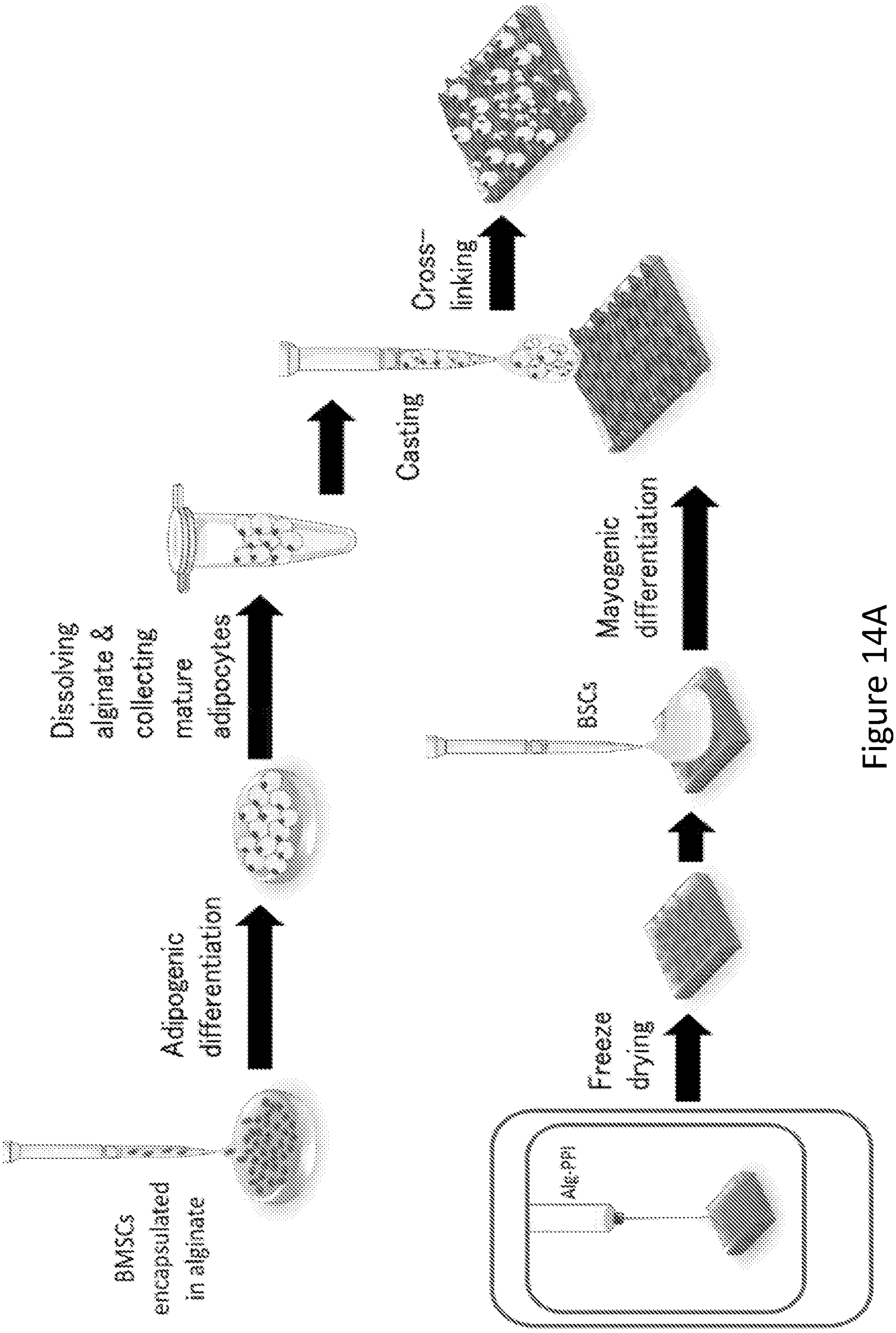
FIG. 14A schematically illustrates a preparation process for 3D printed lyophilized-Alginate-PPI hydrogel, on which BSCs are seeded and differentiated into myotubes, and then mature Adipocytes (differentiated BMSCs) suspended in alginate mixture are casted onto it and crosslinked, to create the final, hybrid scaffold.
Figure 14B:
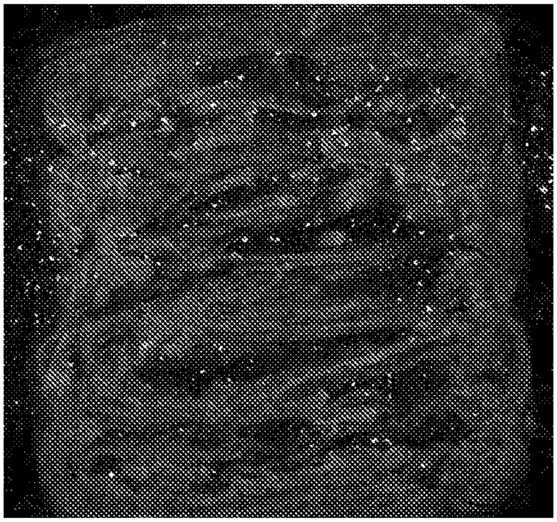
FIGS. 14B-D show confocal images of muscle-adipose combined—3D printed scaffold that was produced as described in FIG. 14A. Grey, Desmin (marker for myotubes); light grey, LipidTox (marker for lipid droplets in the adipocytes); dark grey, DAPI (marker for the cell nucleus).
Figure 14C:
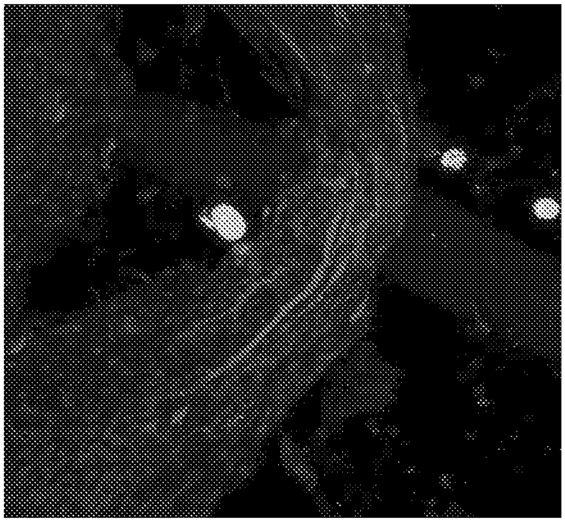
Figure 14D:
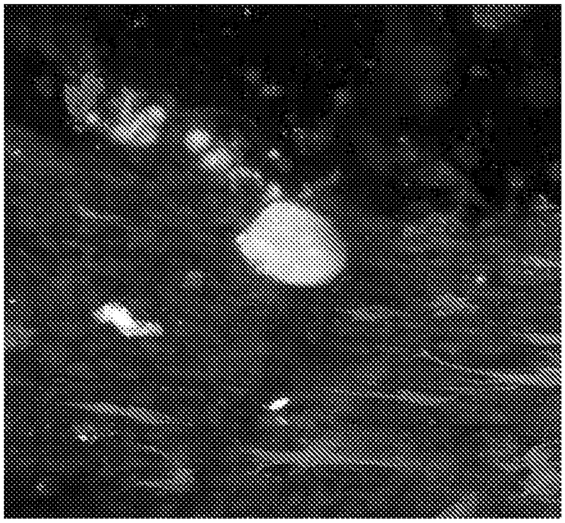

Next, the adipocytes in the alginate-based composition were casted on the 3D printed scaffold that becomes covered with differentiated myotubes, and crosslinked with a calcium solution. FIG. 14A schematically illustrates the production process of the 3D scaffold described herein, which was similar to method 400 as disclosed herein above. Images of muscle-adipose combined-3D printed scaffold that was produced according to the protocol described herein is shown in FIGS. 14B-D.

Example 18—Bovine Satellite Cells on PVA-Alginate-Pea Protein Scaffold

Figure 15A:
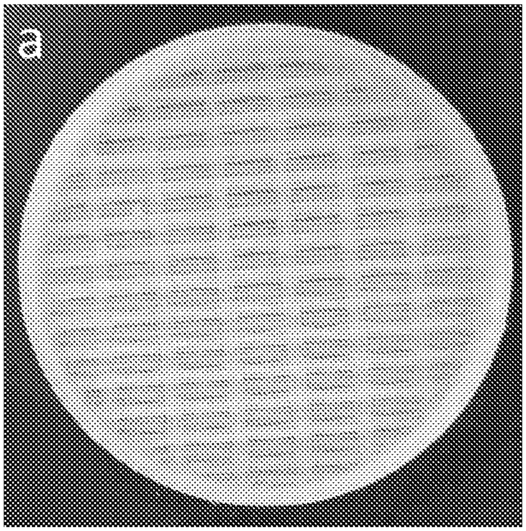
FIGS. 15A-D show: a PVA 3D printed mold (FIG. 15A); confocal images of Live dead assay for Bovine satellite cells spreading on alginate:pea protein isolate (2%:2%) scaffold, scale bar of 500 μm and 2.5× magnification (FIG. 15B); scale bar of 100 μm and 10× magnification (FIG. 15C), and seeding efficiency of bovine satellite cells in PVA-alginate: pea protein isolate scaffolds (FIG. 15D).
Figure 15B:
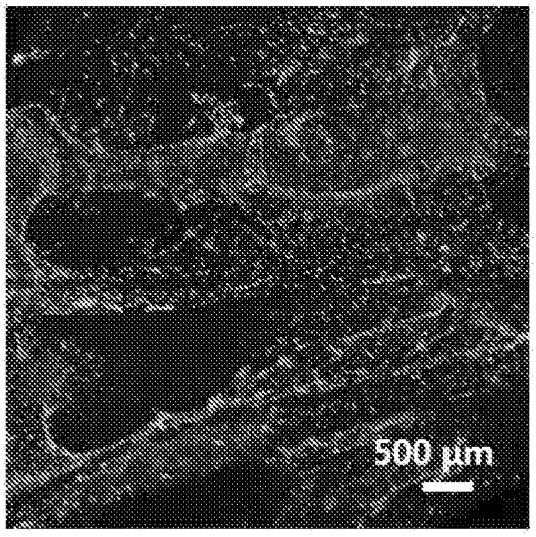

Polyvinyl alcohol (PVA) mold was created by 3D printing (FIG. 15A). Alginate (Alg) and pea protein isolate (PPI) were mixed at different concentrations (final concentrations are 1:1, 2:2 or 4:2% w/v Alg:PPI). Scaffold mixture was casted into the mold, crosslinked with $CaCl_2$) and frozen at −80° C. for 3 hours. Then the scaffold was lyophilized overnight. After lyophilization the mold was removed by its suspension in 100 mM $CaCl_2$) solution. The scaffold was then cut to a desired size, and freeze dried again.

In order to allow cell attachment, the scaffold was treated with vitronectin (VTN). Immediately before seeding, VTN was removed from the scaffold and $10^5$ to $10^6$ bovine satellite cells were seeded onto the scaffold (6 mm diameter). Within an hour after seeding, proliferation medium was added to the plate.

Figure 15C:
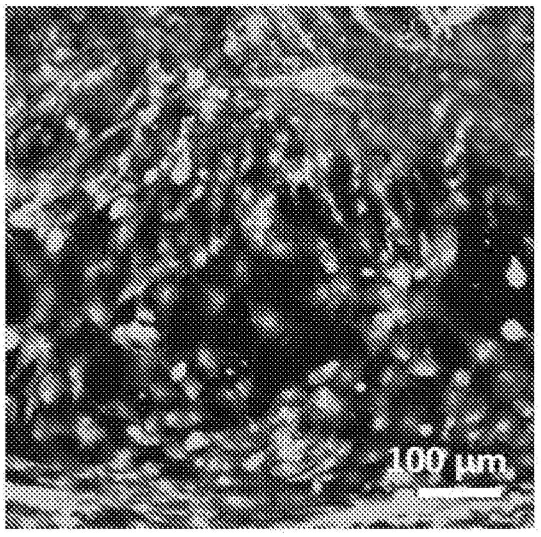
Figure 15D:
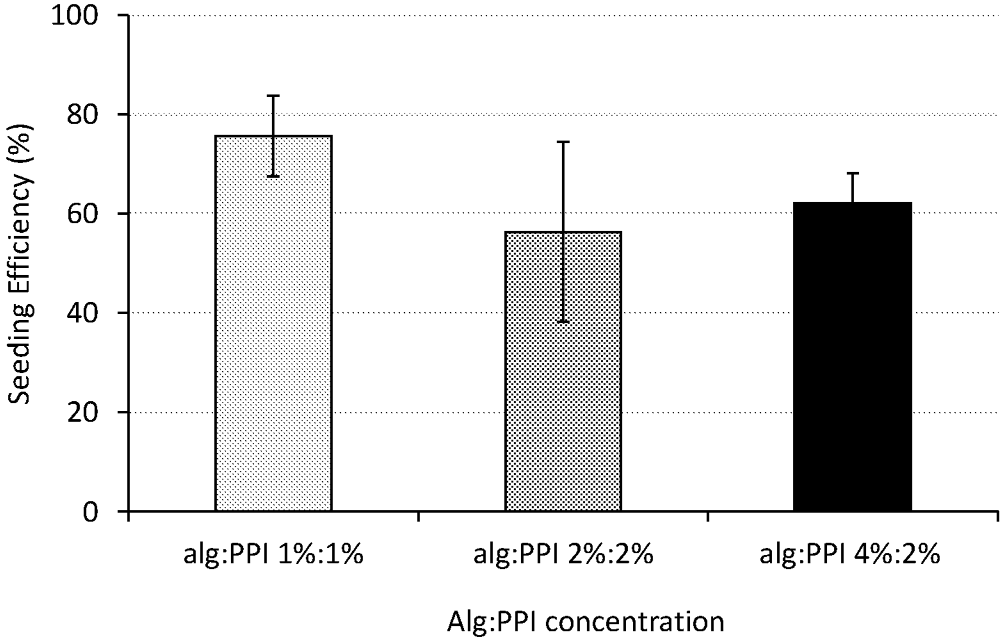

5 days after seeding the cell viability was examined by a live/dead cell assay. FIG. 15 shows that Bovine satellite cells are alive (grey) and spread nicely on the alginate:pea protein scaffold (FIG. 15B, 2.5× magnification) and have an elongated morphology (FIG. 15C, 10× magnification). No dead cells (anticipated to be dyed red) were observed.

Cell seeding efficiency on the alginate-high pea protein concentration scaffolds was calculated 24 hrs. post seeding. Using trypsin (0.25% trypsin-EDTA) all cells which were attached to each wells' bottom were lifted and mixed with cells which might be present in the media. Cell counting was used to calculate the number of cells unattached/not entrapped within the scaffolds. Seeding efficiency was then calculated by equation 3 as presented herein above. The results can be observed at FIG. 15D.

Example 19—Pattern Effect on Viability

To obtain elevated cell viability in a thick scaffold (about 0.5 cm thick) made of 1%-1% w/v Alginate-PPI, a printing pattern which contains voids was designed, to enhance inner material transfer. It is contemplated that controlling the scaffold's geometry via the designed printing pattern can improve the number of viable cells in thick scaffolds.

Figure 16A:
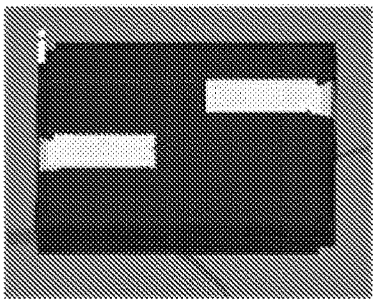
FIGS. 16A-C show images of a scaffold model design intended for 3D-printing: a pattern with longitudinal voids between 2 consecutive layers (FIGS. 16A-B), and a full bulk cube with no voids (FIG. 16C).
Figure 16B:
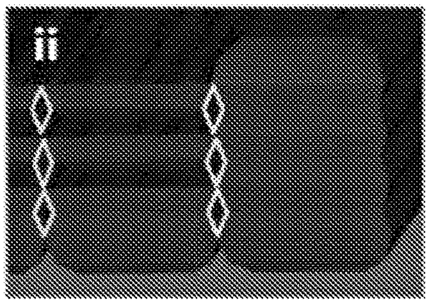
Figure 16C:
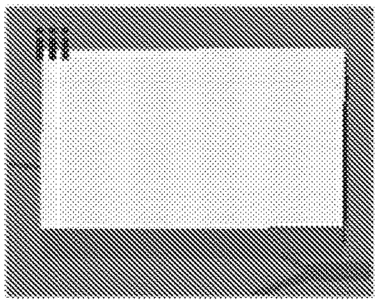

Two patterns were designed to assess the contribution of voids within 0.5 cm-thick 10×15 mm scaffolds:

A pattern with longitudinal voids between 2 consecutive layers (FIGS. 16A-B), sectioned to 2 areas to demonstrate the ability of multi-material printing; and A bulk cube of similar dimensions, with no voids ('full' pattern), used as control (FIG. 16C).

Figure 17A:
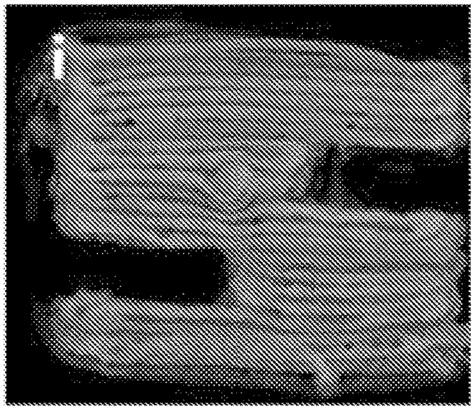
FIGS. 17A-B show confocal microscope images at 10× magnification of 3D printed 1%-1% Alginate-PPI scaffolds: a pattern with longitudinal voids based on FIGS. 16A-B (FIG. 17A), and a full bulk cube with no voids based on FIG. 16C (FIG. 17B). Visualization is enabled by fluorescent beads incorporated within the ink.
Figure 17B:
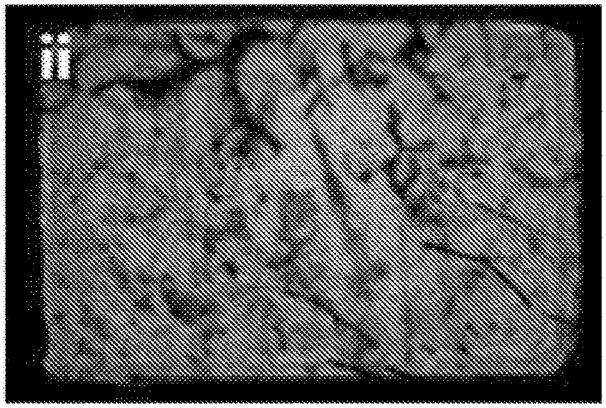

First, printing was performed without cells (one of the inks was supplemented with fluorescent beads for visualization), to evaluate the resultant printed scaffolds. As can be seen, successful multi-layered constructs with a fibrous texture could be fabricated with the void-containing pattern, where consecutive layers attach while the fibers in the same layer remain separate (FIG. 17A). Moreover, the 'full' pattern resulted in bulk-like scaffolds, with no apparent voids (FIG. 17B).

To fabricate cell-containing scaffolds, two 1%-1% Alginate-PPI inks were mixed with BSCs P.5 (final cell concentration: $5\times10^6$ cells/ml). Later, the mixtures were printed into the support Agar bath, which was followed by bath removal, as previously disclosed herein above for example at Example 3. All of the scaffolds were then supplemented with cell-cultivation medium (BioAmf-2) for 8 days.

Figure 18A:
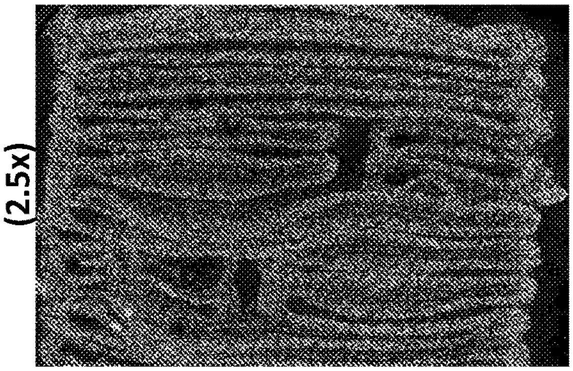
FIGS. 18A-G show results for 3D printed 1%-1% Alginate-PPI mixed with BSCs scaffolds: representative confocal microscope images obtained for the Live/Dead cell assay at day 8: top view of void pattern with 2.5× magnification (FIG. 18A); top view of full pattern with 2.5× magnification (FIG. 18B); cross-section of void pattern with 2.5× magnification (FIG. 18C); cross-section of full pattern with 2.5× magnification (FIG. 18D); cross-section of void pattern with 10× magnification (FIG. 18E); cross-section of full pattern with 10× magnification (FIG. 18F); and statistical analysis done using Prism's Two-Way ANOVA to assess viability of 3D-printed BSCs (FIG. 18G).
Figure 18B:
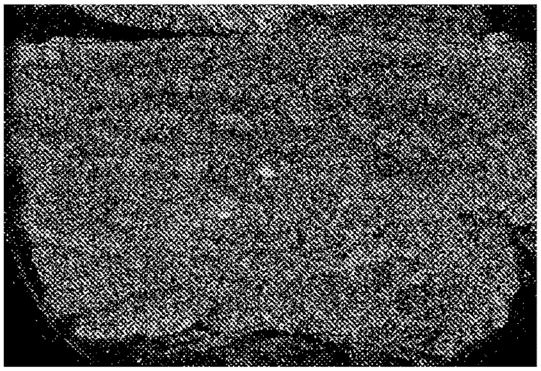
Figure 18C:
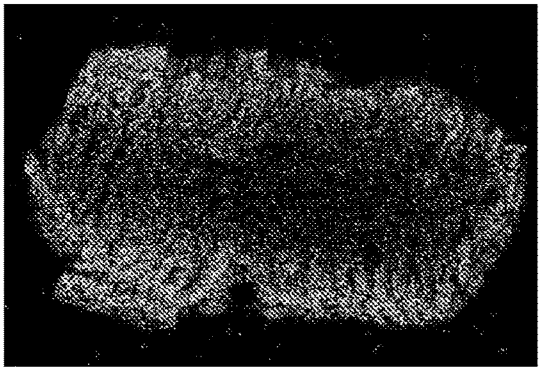
Figure 18D:
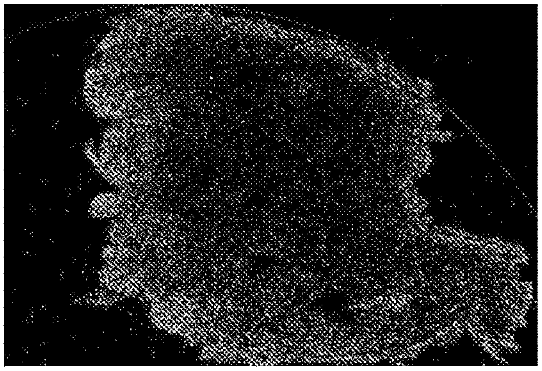
Figure 18E:
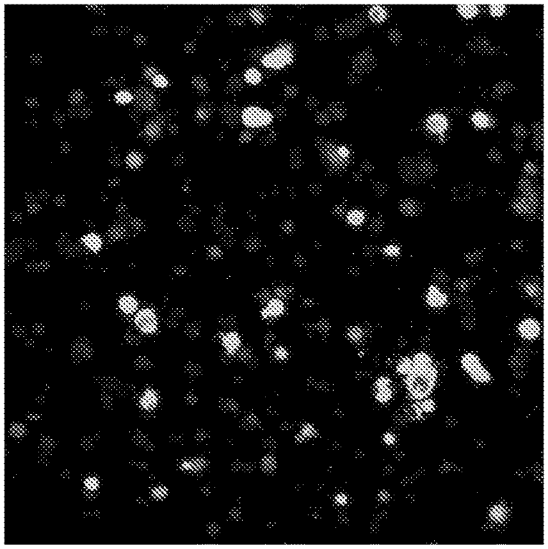
Figure 18F:
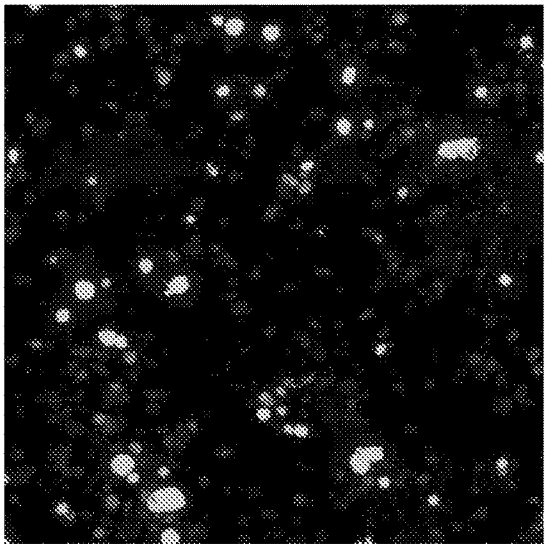
Figure 18G:
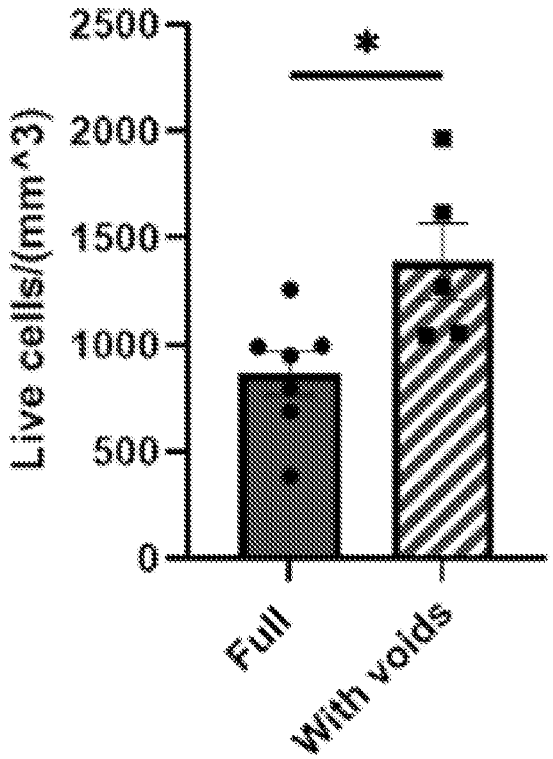
Figure 19A:
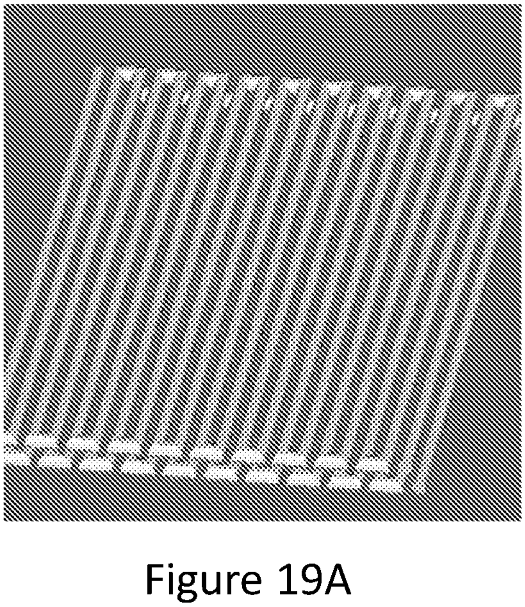
FIGS. 19A-F show 3D printed BMSCs in 2% PPI— 1% alginate bio-ink scaffolds: elongated fibers design intended for 3D-printing (FIG. 19A); Bright field image of the scaffold of FIG. 19A (FIG. 19B); live/dead cell assay that was performed 5 days—post printing for the scaffold of FIG. 19B (FIG. 19C); grid pattern design intended for 3D-printing (FIG. 19D); Bright field image of the scaffold of FIG. 19D (FIG. 19E), and live/dead cell assay that was performed 5 days—post printing for the scaffold of FIG. 19E (FIG. 19F).
Figure 19B:
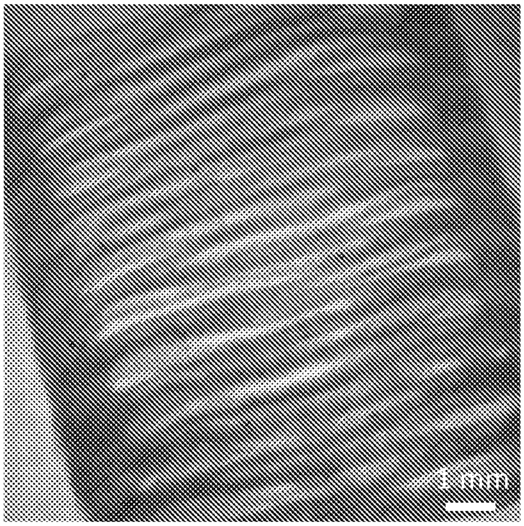
Figure 19C:
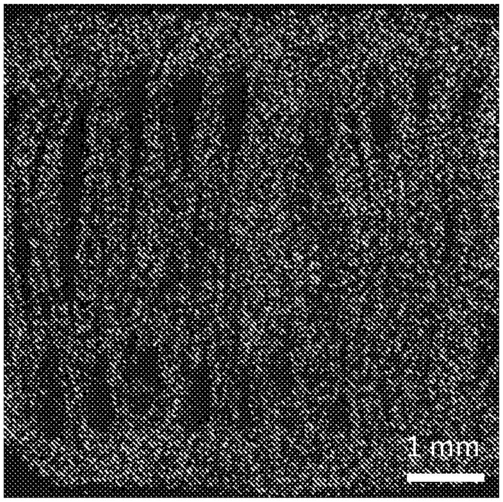
Figure 19D:
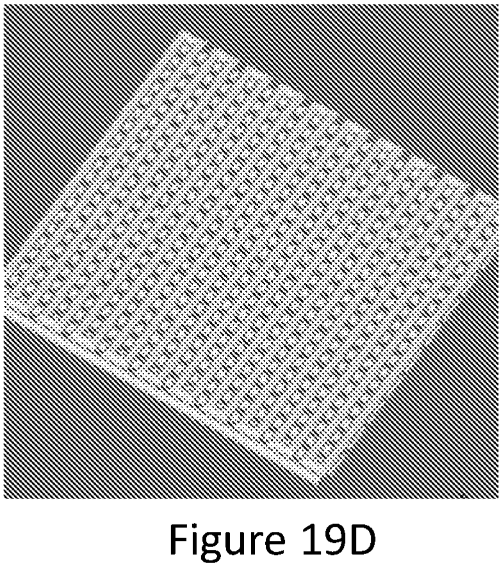
Figure 19E:
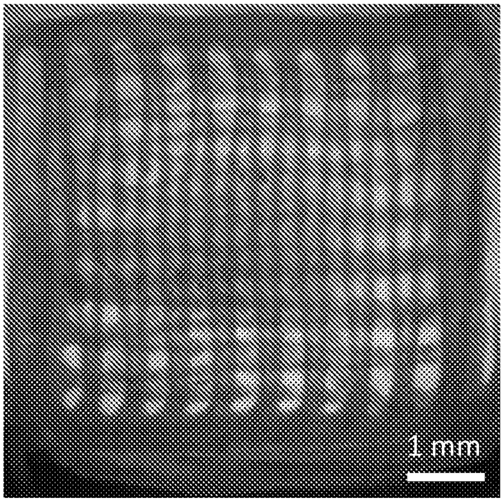
Figure 19F:
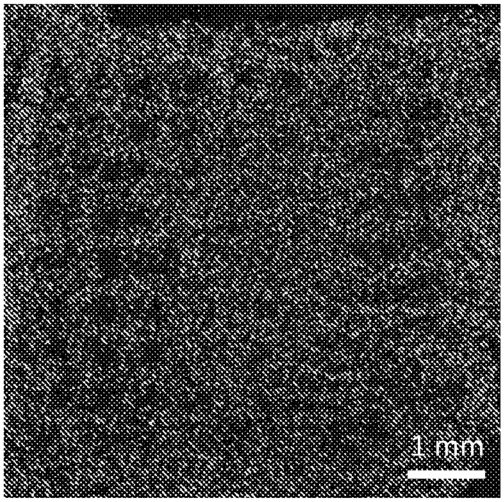
Figure 20A:
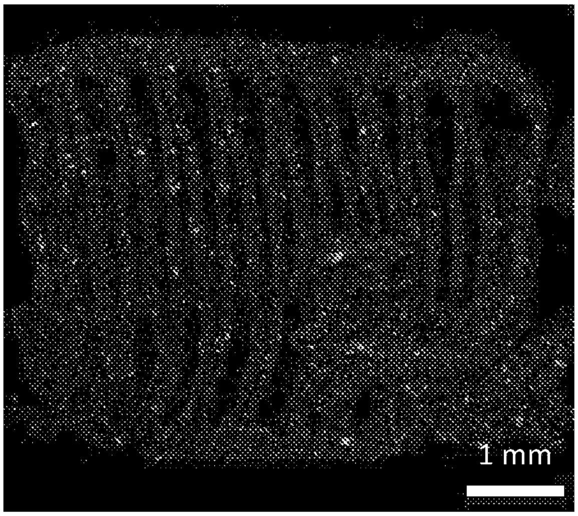
FIGS. 20A-D show 3D printed BMSCs in 2% PPI— 1% alginate bio-ink scaffolds post adipogenic differentiation and maturation. Confocal microscope images stained with LipidTox (light grey), a marker for lipid droplets, and Draq5 (grey), a nucleic marker, in different magnifications: Scale bar 1 mm (FIG. 20A); 200 μm (FIG. 20B); and 50 μm (FIGS. 20C-D).
Figure 20B:
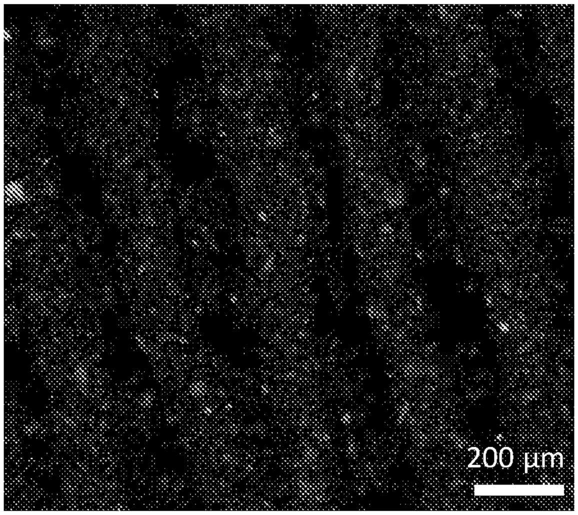
Figure 20C:
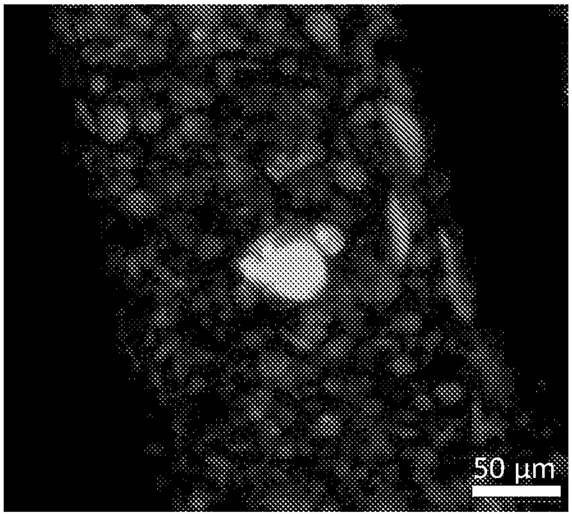
Figure 20D:
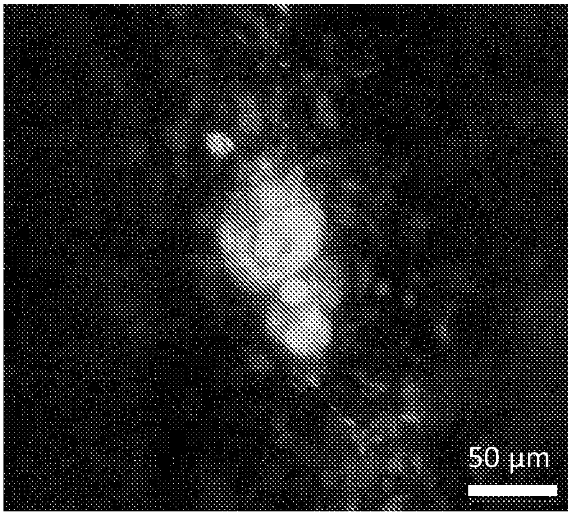

At day 8, a Live/Dead essay was performed, with confocal images taken with 2.5× & 10× magnifications, to visualize the scaffolds (FIGS. 18A-D) and also analyze the number of viable cells (FIGS. 18E-F). The 10× magnifications were taken from the center area of the scaffolds. As can be seen, the number of viable cells per $mm^3$ increased in the void-containing scaffolds, compared to the bulk-like control (FIG. 18G).

Example 20—3D Printing of Bovine MSCs and Differentiation into Adipocytes

Bovine mesenchymal stem cells (BMSCs) were suspended in 2% PPI— 1% alginate ink (final cell concentration: $15\times10^6$ cells/ml). Next, the cell-containing bio-ink was 3D printed into the support agar bath which was followed by bath removal, similarly to the protocol presented in example 3 herein above. Then, the 3D printed scaffolds were cultured in BMSC medium for 1 day and transferred to adipogenic differentiation medium for 2 weeks followed by maturation medium for another 2 weeks, to obtain BMSCs differentiation into mature adipocytes.

Five days—post printing, a Live/Dead essay was performed, with confocal images taken, showing high viability of the cells and homogenous spreading (FIGS. 19A-F).

Confocal microscope images of BMSCs printed in 2% PPI— 1% alginate ink, after 2-week adipogenic differentiation and 2-week maturation phase are displayed in FIGS. 20A-D. Samples were stained with LipidTox (light grey), an adipogenic marker, and Draq5 (grey), a nucleic stain. A successful adipogenic differentiation of the BMSCs in the PPI-alginate bio-ink can be seen.

Example 21—Co-Axial Deposition to Create Cellular Fibers/Channels in 3D Printed Scaffolds Coaxial printing is a printing configuration where two materials are deposited simultaneously, in a 'core-shell' geometry. Coaxial bioprinting was previously disclosed, to generate cellular fibers or hollow perfusable channels (Kjar A. et al., "Engineering of tissue constructs using coaxial bioprinting." Bioactive Materials 6.2 (2021): 460-471). It is suggested that coaxial bioprinting can be used to create thick, perfusable muscle scaffolds as cultured meat, by performing coaxial deposition of the pea-protein enriched compositions as disclosed herein above at the previous examples with additional materials, all the while using the cell-friendly bath-based 3D printing technique disclosed herein above.

PPI-Alginate:RGD was used in coaxial printing, to create unidirectional cellular strands. The PPI-Alginate:RGD (1%-1% w/v) composition served as the 'shell' material, eventually forming the tubes' walls, while a non-gelling hyaluronic-acid (0.5%) solution mixed with BSCs served as an inner, liquid, bio-degradable, cell-carrier 'core' material.

Figure 21A:
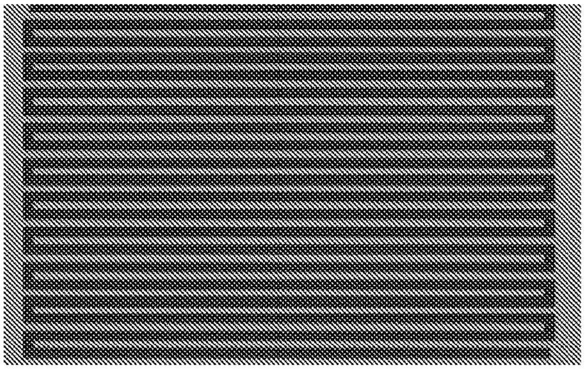
FIGS. 21A-D show coaxial printing of a scaffold containing core-shell continuous parallel strands, the shell contained PPI-Alginate:RGD while the core contained hyaluronic-acid with cells: core-shell continuous parallel strands design (FIG. 21A); imaging of the printed scaffold with 2.5× magnification (FIG. 21B), and imaging of the printed scaffold with 10× magnification (FIGS. 21C-D).

GFP-expressing HNDF cells (appears as light grey), were mixed with the 0.5% HA (in PBS) in a concentration of 5 Million cells/ml, while fluorescent beads (appears as dark grey) were mixed with PPI-Alginate:RGD, for visualization. For the simultaneous deposition, a 2218 Rame-Hart coaxial needle was used. The two solutions were co-printed into an agar support bath containing 10 mM $CaCl_2$, to create a scaffold made of core-shell continuous parallel strands, as can be seen in the pattern design in FIG. 21A.

After printing, suitable medium was added on-top of the agar support bath, for further cultivation. The principle of this cultivation configuration, without removal of the bath, was previously disclosed herein above in example 15, FIGS. 12E-I ('within bath').

Figure 21B:
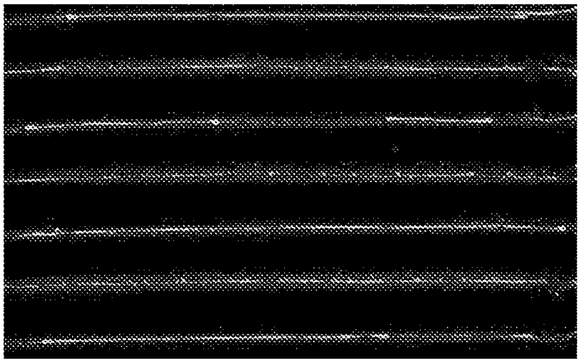
Figure 21C:
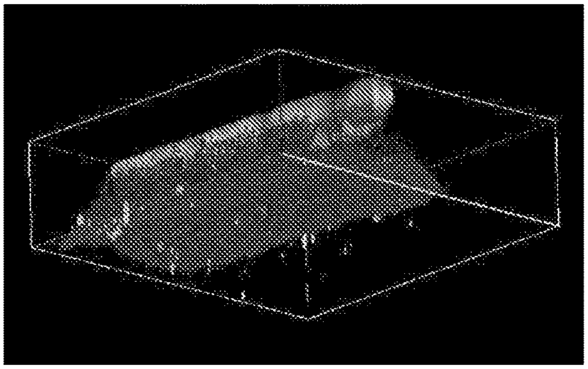
Figure 21D:
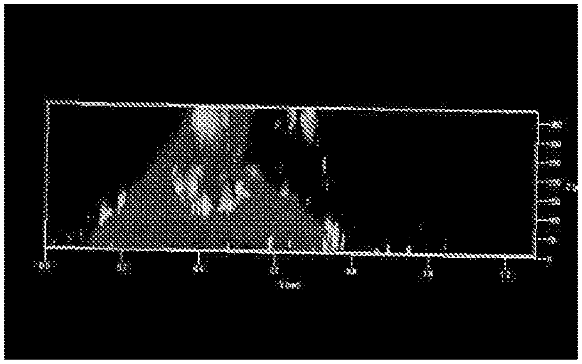

The printed scaffold was then imaged using Confocal imaging with 2.5× (FIG. 21B) & 10× (FIGS. 21C-D) magnifications, while kept in the bath, 7 days after printing, to evaluate cell behavior.

As can be seen, the printing resulted in well-formed cellular fibers, showing the envelopment of cells within the PPI-Alginate:RGD shell. It should be noted that although the cells here were not from bovine origin, the same scaffolds can be implemented with bovine derived cells, especially BSCs, to create unidirectional muscle fibers.

Many beneficial variations could be considered for the fabrication of core-shell scaffolds for cultured meat purposes:

1. Different cell-containing core materials: while the outer shell is stiff PPI-Alginate for mechanical support, other soft cell-laden cores could be considered (such as recombinant collagen, recombinant gelatin, Hyaluronic acid, chitosan, pectin, carrageenan, guar gum, xanthan gum, and the like).
2. Different cell types—such as the MSCs—could be combined, either in the outer shell, or in separate strands with MSC-containing cores, enabling more complex multi-cellular scaffolds. As the PPI-Alginate composition can be deposited in a cell-friendly manner, cells could be mixed with it, with a different ink co-deposited with it, or even both.
3. Hollow channel fabrication: In this co-axial technique, temporary removable/dissolvable/non-gelling core materials could be used to create hollow tubes, such as hyaluronic acid, pectin, carrageenan, guar gum, xanthan gum, recombinant gelatin, Pluronic F-127, PVA, Butenediol vinyl alcohol (BVOH), etc. This could be beneficial in the final scaffold, for medium flow and material distribution throughout the growing tissue.

Example 22— Bovine Satellite Cells on Alginate-High-Pea-Protein-Concentration Scaffolds Pea protein isolate was dissolved in 0.3M NaCl solution (pH 7 or 2) to a final protein concentration of 15% in a glass vial. The sample was stirred for 5 minutes, then heated in an oven at 80° C. for 20 minutes (while stirring lightly with a shaker). Immediately after heating the sample was kept on ice for 30-45 minutes. 2 gr of 15% protein mixture (300 mg protein) was mixed with 600 μl alginate (alginate concentrations before mixing are 0.5%, 1% or 2% to reach final Alg:PPI ratios of 1:100, 1:50 and 1:25).

Several mixtures were prepared and casted into PDMS molds (similarly to example 1) and the alginate was cross-linked with $CaCl_2$. The mixtures had the following alginate: PPI final concentrations of: 0.54%:13.4%, 0.27%:13.4% and 0.13%:13.4% w/v.

After the extraction of the scaffolds from the molds they were frozen at −20° C. to −800° C. Then the scaffolds were lyophilized overnight, and kept in desiccator until seeding.

Bovine satellite cells were stained with DiI (appears as grey), then $10^5$ to $10^6$ cells were seeded by tapping on each scaffold (6 mm diameter). 45 minutes after seeding, proliferation medium was added to the plate. 7 days after seeding differentiation was begun. Differentiation duration was 7 days.

The cells were imaged 6 days after seeding and after 7 days of differentiation using confocal microscope with 2.5× and 10× magnifications. FIG. 22 demonstrates that Bovine satellite cells proliferate and spread nicely on the alginate: high-pea-protein-concentration scaffold when supplemented with proliferation medium (FIGS. 22A-B), and thereafter differentiation (FIG. 22C) mediums. Without wishing to be bound with specific theory or mechanism of action, the elevated protein concentration in the bioink composition enable the cell attachment and growth without the need of coupling RGD to alginate.

Figure 22A:
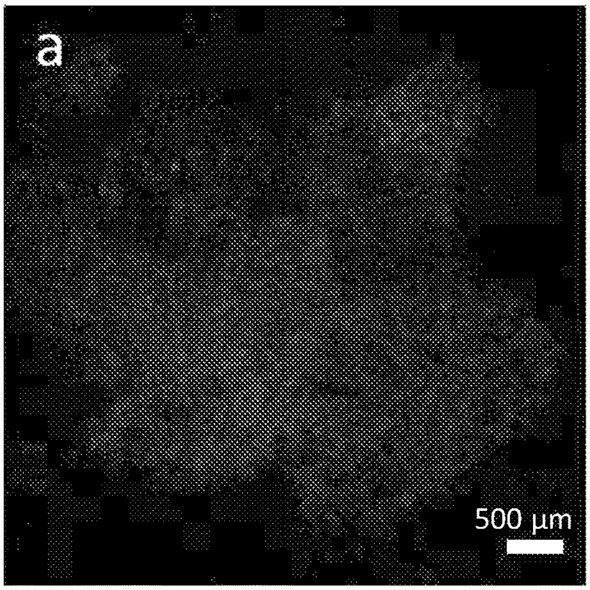
FIGS. 22A-C show confocal images of Bovine satellite cells stained with DiI seeded on alginate with high pea protein concentration (0.54%:13.4% alginate: pea protein) scaffold: 6 days after seeding using 2.5× magnification (FIG. 22A); enlargement of FIG. 22A, 10× magnification (FIG. 22B), and after 7 days of differentiation, 10× magnification (FIG. 22C).
Figure 22B:
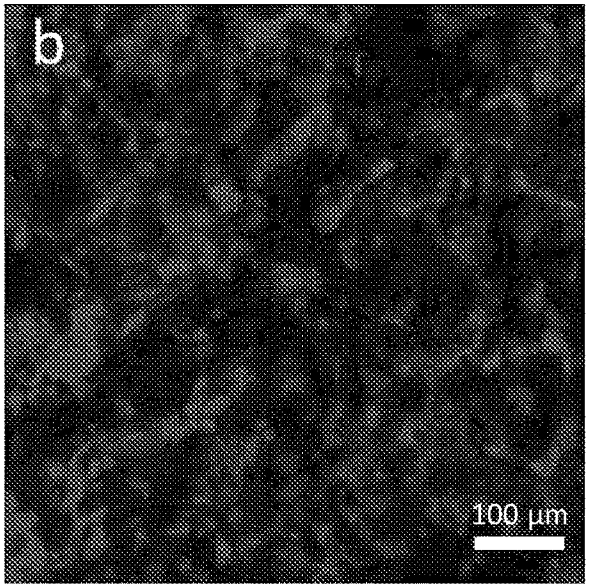
Figure 22C:
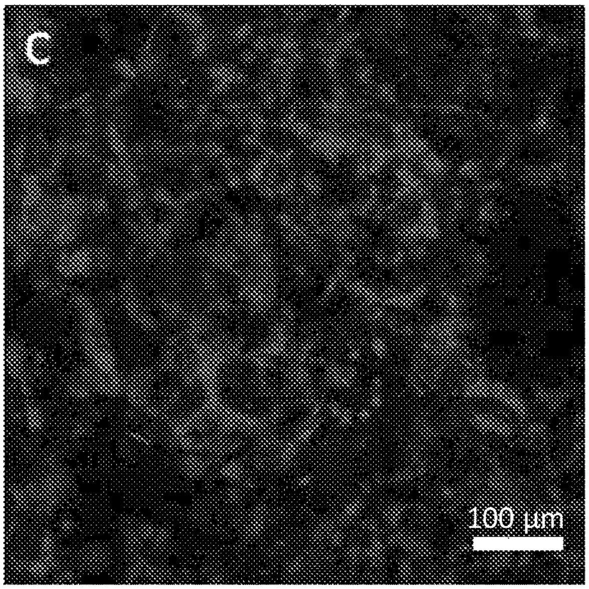
Figure 22D:
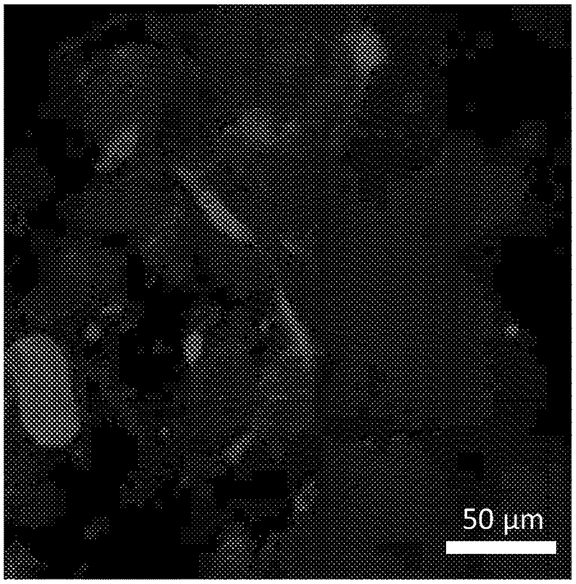
FIG. 22D show confocal images with 40× magnification of myoblast differentiation to myotubes (after 3 days of differentiation) on alginate:high PPI concentration (0.54%: 13.4%) scaffold. The cells were seeded without any scaffold's treatment.
Figure 23C:
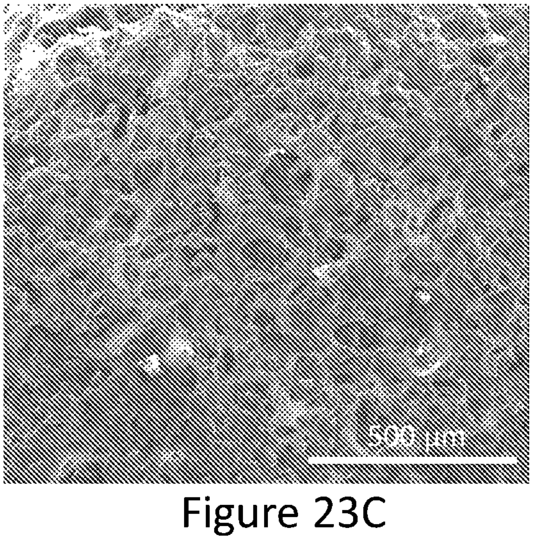
Figure 23D:
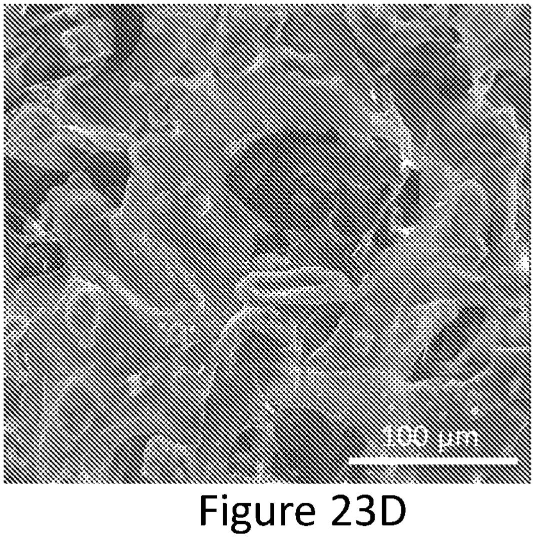
Figure 23E:
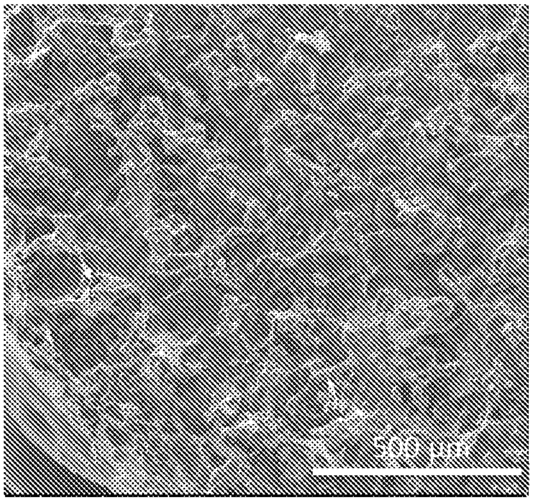
Figure 23F:
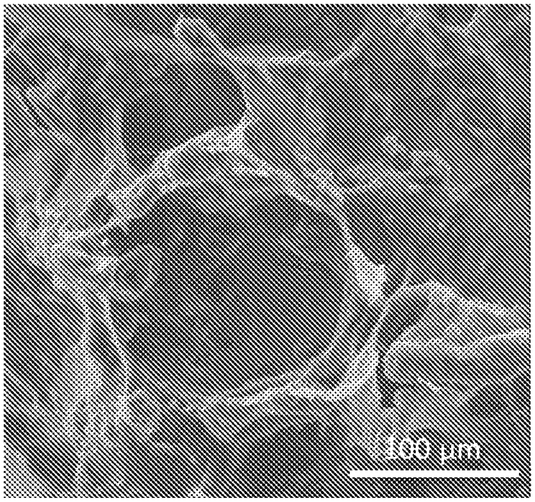

FIG. 22D show confocal image of myoblast differentiation on the alginate:PPI 0.54%:13.4% w/v scaffold, with ×40 magnification. The cells were seeded without any scaffold's treatment. As can be seen in FIG. 22D, after 3 days of differentiation myotubes were observed.

Cell seeding efficiency on the alginate-high pea protein concentration scaffolds was calculated 24 hrs. post seeding. Using trypsin (0.25% trypsin-EDTA) all cells which were attached to each wells' bottom were lifted and mixed with cells which might be present in the media. Cell counting was used to calculate the number of cells unattached/not entrapped within the scaffolds. Seeding efficiency was then calculated by equation 3 as disclosed herein above. Overall, the results show (FIG. 22E) high seeding efficiency in all scaffold composition examined.

Dry scaffolds were imaged using Quanta 200 scanning electron microscope (FEI) at 20 kV and spot size 4.5, before imaging the scaffolds were coated with Au/Pd mixture under vacuum conditions. FIGS. 23A-F show a porous structure of the scaffolds. Overall, as can be seen, the size of the pores varies depending on the alginate concentration, when larger pores were observed in a lower alginate concentration scaffold.

Example 23—Bovine Satellite Cells within Alginate-High-Pea-Protein-Concentration Scaffolds Pea protein isolate was dissolved in 0.3M NaCl solution (pH 7) to a final protein concentration of 15% in a glass vial. The sample was stirred, then heated in an oven at 80° C. for 20 minutes. Immediately after heating the sample was kept on ice for 30-45 minutes. 2 gr of 15% protein mixture (300 mg protein) was mixed with 600 μl alginate (alginate concentrations before mixing are 0.5%, 1% or 2%) to reach final ratios of 1:50 and 1:25 (final concentrations were: 0.27%:13.4% and 0.54%:13.4% w/v of alginate:pea protein). Bovine satellite cells were mixed gently with the alginate:pea protein mixtures, and then casted into PDMS molds.

After alginate crosslinking with $CaCl_2$ the scaffolds comprising cells encapsulated therein were extracted from the mold and moved to proliferation medium. Similarly, as blank, scaffolds without cells were prepared.

The metabolic activity of the cells was examined a day, two and seven days after seeding (days 1, 2 and 7, respectively) using Alamar blue reagent. The samples were incubated in proliferation medium containing 10% Alamar blue at 37° C. for 5 hours. Following incubation solutions were transferred to a 96 flat-bottom well plate and fluorescence was measured using a Varioskan LUX plate reader (Thermo-Fisher). Excitation and emission wave lengths were 555 nm & 585 nm, respectively. To calculate the metabolic activity fold of change, measured values of days 2 or 7 were normalized to the value obtained at the first day after seeding (day 1). 3 replicates were done for each scaffold type (N=3).

Figure 24A:
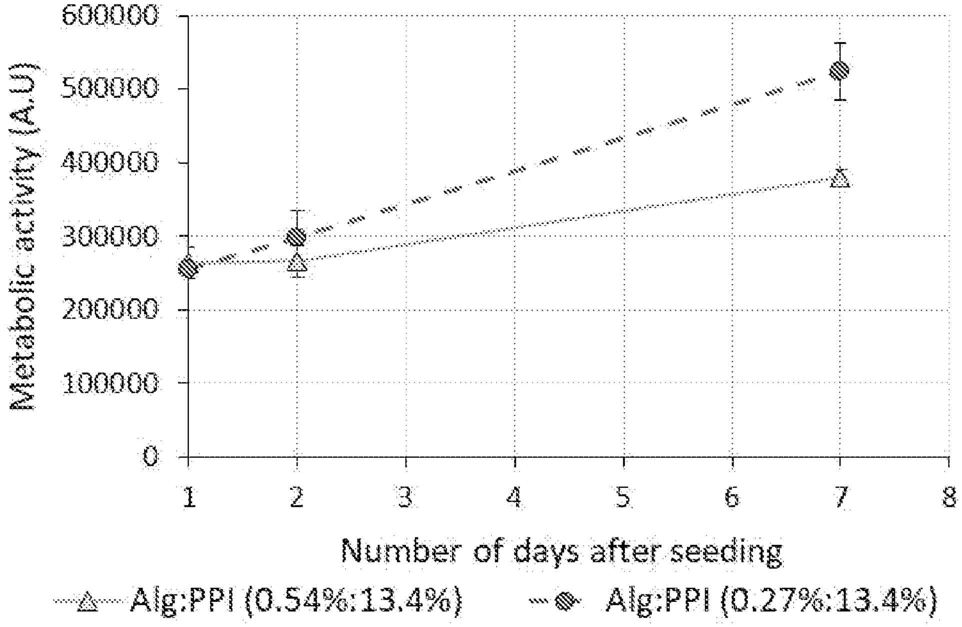
FIGS. 24A-B: show viability of bovine satellite cells in alginate:high pea protein concentration (0.54%:13.4% and 0.27%:13.4%) scaffolds: metabolic activity during proliferation duration (FIG. 24A), and fold of change in metabolic activity during proliferation duration relative to the metabolic activity in the first day after seeding (FIG. 24B). Statistical analysis was done using Two-Way ANOVA, B, N=3. * and *** signify a p-value below 0.05 and 0.001, respectively.
Figure 24B:
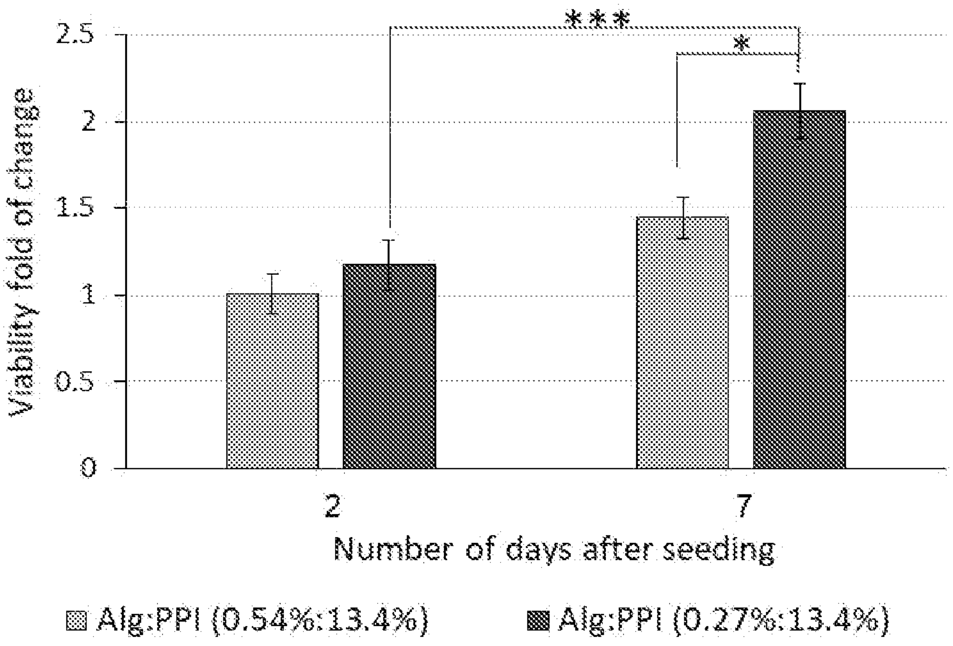

Alamar blue assay shows that in both scaffolds concentrations there is an increase in fluorescence intensity overtime, compared to the intensity at day 1 (FIGS. 24A-B). This could indicate that there was an increase in the metabolic activity during the proliferation duration, which show high viability of bovine satellite cells in the alginate: high-pea-protein-concentration scaffolds. Moreover, comparison between both scaffold compositions show that the metabolic activity at day 7 is significantly higher ($p<0.05$) in scaffold containing 0.54%:13.4% alginate:pea protein than in 0.27%: 13.4% alginate:pea protein scaffold.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for producing an edible three-dimensional (3D) scaffold, the method comprising the steps of:

a. providing at least one aqueous composition comprising at least one type of edible protein at a concentration range of about 0.1-15% w/v of the composition, and at least one type of edible polysaccharide;

b. providing a support medium compatible to scaffold fabrication, wherein the support medium comprises an edible, non-animal derived material;

c. depositing the at least one aqueous composition of step (a) into the support medium of step (b) in a predetermined pattern, thereby forming at least one edible member therein, wherein the deposition is performed under conditions comprising exposing said at least one edible member to at least one crosslinking mechanism, thus enabling the transition of the at least one edible member to a solid or semisolid state, thereby forming a 3D scaffold having a predetermined structure comprising at least one layer comprising the at least one edible member; and optionally, d. separating the support medium from the 3D scaffold of step (c) in order to release it therefrom.

2. The method of claim 1, wherein (i) the at least one type of protein is derived from at least one of a plant, a fungus, an alga, a single cell microorganism, a non-human animal and any combination thereof; (ii) the edible, non-animal derived material of step (b) comprises a hydrogel; or (iii) both (i) and (ii).

3. The method of claim 1, wherein the at least one type of polysaccharide is selected from the group consisting of alginate, starch, bean, gum, gellan-gum, hyaluronic acid, cellulose, chitin, chitosan, xanthan gum, agar, agarose, pectin, dextran, carrageenan, modifications and/or variations thereof, and combinations thereof.

4. The method of claim 1, wherein the composition of step (a) is in a form of an aqueous solution comprising the at least one type of edible protein at a concentration range of about 0.1-15% w/v of the composition and the at least one type of edible polysaccharide at a concentration range of about 0.1-5% w/v of the composition.

5. The method of claim 1, wherein the composition of step (a) comprises at least one type of protein selected from the group consisting of pea protein isolate (PPI), soybean protein isolate (SPI), and a combination thereof, and at least one type of polysaccharide selected from the group consisting of alginate and RGD-modified alginate.

6. The method of claim 1, wherein the composition of step (a) is characterized by having a viscosity in the range of from about 30 mPa to about $6\times10^7$ mPa.

7. The method of claim 1, wherein the support medium is in the form of a removable support bath comprising said edible, non-animal material, wherein said material is a hydrogel comprising agar microparticles and at least one divalent ion or the salt thereof disposed therein, and wherein during step (c) relative movement is initiated between the support bath and an apparatus configured to deposit the at least one composition of step (a) into the support bath, wherein said hydrogel is configured to provide support during deposition and crosslinking of the at least one edible member therein, thereby forming the 3D scaffold having a predetermined structure.

8. The method of claim 1, wherein the deposition at step (c) of the at least one composition of step (a) into the support medium, is performed using a 3D printer comprising an extruder, wherein step (c) comprises at least partially inserting the extruder into the support medium and extruding the at least one edible member at least partially within the support material.

9. The method of claim 1, wherein said method comprises providing at least two compositions at step (a) comprising a first composition and a second composition, wherein each of the first and the second composition comprises at least one type of protein at a concentration range of about 0.1-15% w/v of the composition, and at least one type of polysaccharide.

10. The method of claim 1, wherein the composition of step (a) further comprises a plurality of at least one type of non-human-animal cells.

11. The method of claim 10, wherein the composition of step (a) comprises at least one type of protein selected from PPI and SPI at a concentration range of about 0.1-15% w/v of the composition; at least one type of polysaccharide comprising alginate or RGD-modified alginate at a concentration range of about 0.1-5% w/v of the composition, and at least one type of non-human-animal cells at a concentration range of about $5\times10^3$-$500\times10^6$ cell/ml of the composition.

12. The method of claim 10, wherein following step (d) the method further comprises placing the 3D edible scaffold comprising a plurality of at least one type of non-human-animal cells under growth conditions enabling differentiation and/or growth of the plurality of at least one type of non-human-animal cells to form at least one type of tissue, thereby producing cultured meat product.

13. A 3D scaffold comprising a plurality of at least one type of non-human-animal cells fabricated by the method of claim 10, for use in growing a 3D nutritious engineered edible tissue, intended for cultured meat.

14. A cultured meat product produced by the method of claim 10.

15. A 3D edible scaffold comprising at least one layer comprising at least one edible member, wherein the at least one edible member comprises at least one hydrogel composition comprising: at least one edible protein selected from PPI and SPI at a concentration range of about 0.1-15% w/v of the composition and at least one edible polysaccharide at a concentration range of about 0.1-5% w/v of the composition.

16. The 3D edible scaffold of claim 15, wherein said scaffold is characterized by at least one of: (a) the scaffold further comprises a plurality of at least one type of non-human-animal cells, and (b) the edible polysaccharide is selected from alginate or RGD-modified alginate.

17. A cultured meat product comprising the 3D scaffold of claim 16.

18. An edible ink comprising a hydrogel composition comprising at least one type of edible protein selected from PPI and SPI at a concentration range of about 0.1-15% w/v of the composition, and at least one type of edible polysaccharide at a concentration range of about 0.1-5% w/v of the composition, wherein the ink is suitable for 3D printing.

19. The edible ink of claim 18, wherein said ink is characterized by at least one of: (a) the ink further comprises a plurality of at least one type of non-human-animal cells at a concentration range of about $5\times10^3$-$500\times10^6$ cell/ml of the ink; and (b) the edible polysaccharide is selected from alginate or RGD-modified alginate.

20. The method of claim 8, wherein the conditions of step (c) further comprise a printing pressure within a range of about 0.1 to about 20 psi.

21. The method of claim 1, wherein the method comprises the steps of:

a. providing at least one aqueous composition comprising: at least one type of edible protein at a concentration range of about 0.1-15% w/v of the composition, at least one type of edible polysaccharide at a concentration range of about 0.1-5% w/v of the composition, and optionally a plurality of at least one type of non-human-animal cells;

b. providing a support medium compatible to scaffold fabrication, wherein the support medium is in the form of a removable support bath comprising an edible, non-animal derived hydrogel comprising microparticles and at least one divalent ion, or the salt thereof, disposed therein, wherein said hydrogel is configured to provide support during printing and crosslinking of at least one edible member therein;

c. depositing the at least one aqueous composition of step (a) into the support medium of step (b) in a predetermined pattern by 3D printing, comprising at least partially inserting an extruder into the support medium and extruding at least one edible member at least partially within the support medium, thereby forming at least one edible member therein, wherein the deposition is performed under conditions enabling the transition of the at least one edible member to a solid or semisolid state, thereby forming a 3D scaffold having a predetermined structure comprising at least one layer comprising the at least one edible member, wherein said conditions comprise: a printing pressure within a range of about 0.1 to about 20 psi, and exposing said at least one edible member to at least one crosslinking mechanism; and optionally, d. separating the support medium from the 3D scaffold of step (c) in order to release it therefrom.

* * * * *